(12) United States Patent
Sheikhzadeh-Nadjar et al.

(10) Patent No.: US 8,137,269 B2
(45) Date of Patent: Mar. 20, 2012

(54) METHOD AND SYSTEM FOR MANAGING PHYSIOLOGICAL SYSTEM

(75) Inventors: Hamid Sheikhzadeh-Nadjar, Waterloo (CA); Robert L. Brennan, Kitchener (CA); Michael Rice, Woodinville, WA (US)

(73) Assignee: On Semiconductor Trading Ltd., Hamilton (BM)

( * ) Notice: Subject to any disclaimer, the term of this patent is extended or adjusted under 35 U.S.C. 154(b) by 664 days.

(21) Appl. No.: 11/724,642

(22) Filed: Mar. 15, 2007

(65) Prior Publication Data

US 2007/0265508 A1 Nov. 15, 2007

Related U.S. Application Data

(63) Continuation of application No. PCT/CA2005/001412, filed on Sep. 15, 2005.

(30) Foreign Application Priority Data

Sep. 15, 2004 (CA) ..................................... 2481631

(51) Int. Cl.
*A61B 5/00* (2006.01)

(52) U.S. Cl. ....................................... 600/300; 600/301
(58) Field of Classification Search .................... None
See application file for complete search history.

(56) References Cited

U.S. PATENT DOCUMENTS

| | | | |
|---|---|---|---|
| 2003/0013974 A1* | 1/2003 | Natarajan et al. | 600/481 |
| 2004/0071284 A1* | 4/2004 | Abutalebi et al. | 379/406.08 |
| 2006/0056641 A1* | 3/2006 | Nadjar et al. | 381/67 |

* cited by examiner

*Primary Examiner* — Sam Yao
*Assistant Examiner* — Bobby Soriano
(74) *Attorney, Agent, or Firm* — Brinks Hofer Gilson & Lione

(57) ABSTRACT

A method and system for managing physiological systems is provided. The physiological system management (PSM) system includes one or more signal acquisition blocks to collect physiological information. The PSM system includes oversampled filterbanks for transferring one or more input signal related to the physiological information into subband signals, and a subband processing scheme for processing the outputs from the oversampled filterbanks for event detection in one or more physiological systems. The PSM system includes an adaptive controller which decides on the proper control measure and delivers the measure to the one or more physiological systems.

28 Claims, 42 Drawing Sheets

Figure 6: HRAb signal (top), and subband energies (7 bottom rows) for a normal SR.

Figure 7: HRAb signal (top), and subband energies (7 bottom rows) for a normal SR, complicated time-domain pattern.

Figure 8: Maximum (dashed line), average (solid-thin line), the instantaneous (solid-thick line) and the detected peak (dotted line) signals for subband energies (7 bottom rows) of Figure 6.

Figure 9: Peak detection for EGM signal (top row) of Figure 7, EGM peak signals (7 bottom rows): 1: 1-Con ,2: 1-Agg, 3:2&3-Agg, 4: 4&5-Agg, 5: 5&6-Agg, 6:Det-Agg, 7:Det-Con.

Figure 10: Peak detection for EGM signal (top row) of a VT segment, EGM peak signals (7 bottom rows): 1: 1-Con ,2: 1-Agg, 3:2&3-Agg, 4: 4&5-Agg, 5: 5&6-Agg, 6:Det-Agg, 7:Det-Con.

Figure 11: Peak detection for EGM signal (top row) of a VFt segment, EGM peak signals (7 bottom rows): 1: 1-Con ,2: 1-Agg, 3:2&3-Agg, 4: 4&5-Agg, 5: 5&6-Agg, 6:Det-Agg, 7:Det-Con.

Figure 12: Peak detection for EGM signal (top row) of a VF segment, EGM peak signals (7 bottom rows): 1: 1-Con ,2: 1-Agg, 3:2&3-Agg, 4: 4&5-Agg, 5: 5&6-Agg, 6:Det-Agg, 7:Det-Con.

Figure 13: Peak detection for EGM signal (top row) of a VF segment, EGM peak signals (7 bottom rows): 1: 1-Con ,2: 1-Agg, 3:2&3-Agg, 4: 4&5-Agg, 5: 5&6-Agg, 6:Det-Agg, 7:Det-Con.

Figure 14: Peak detection for EGM signal (top row) of a VF segment, EGM peak signals (6 bottom rows): 1: 1-Agg, 2: 2&3-Agg, 3: 4&5-Agg, , 4: 5&6 Agg, 5:Det-Agg, 6:Det-Con.

Figure 15: Peak detection for EGM signal (top row) of an AF segment, EGM peak signals (6 bottom rows): 1: 1-Agg, 2:2&3-Agg, 3: 4&5-Agg, , 4: 5&6 Agg, 5:Det-Agg, 6:Det-Con.

Figure 16: Peak detection for EGM signal (top row) of an AF segment, EGM peak signals (6 bottom rows): 1: 1-Agg, 2:2&3-Agg, 3: 4&5-Agg, , 4: 5&6 Agg, 5:Det-Agg, 6:Det-Con.

Figure 17: Peak detection for EGM signal (top row) of normal rhythm, EGM peak signals (6 bottom rows): 1: 1-Agg, 2:2&3-Agg, 3: 4&5-Agg, 4: 5&6 Agg, 5:Det-Agg, 6:Det-Con.

Figure 18: Peak detection for EGM signal (top row) of normal rhythm, EGM peak signals (6 bottom rows): 1: 1-Agg, 2: 2&3-Agg, 3: 4&5-Agg, 4: 5&6 Agg, 5:Det-Agg, 6:Det-Con.

Figure 19: Peak detection for EGM signal (top row) of normal rhythm, EGM peak signals (6 bottom rows): 1: 1-Agg, 2:2&3-Agg, 3: 4&5-Agg, 4: 5&6 Agg, 5:Det-Agg, 6:Det-Con.

Figure 20: Peak detection for EGM signal (top row) of normal rhythm, EGM peak signals (6 bottom rows): 1: 1-Agg, 2:2&3-Agg, 3: 4&5-Agg, 4: 5&6-Agg, 5:Det-Agg, 6:Det-Con.

Figure 21: Peak detection for EGM signal (top row) of normal rhythm, EGM peak signals (6 bottom rows): 1: 1-Agg, 2: 2&3-Agg, 3: 4&5-Agg, 4: 5&6 Agg, 5:Det-Agg, 6:Det-Con.

FIGURE 31  Subband WOLA-based FX-LMS with reference microphone, with analog ANC

Figure 32: Stethoscope

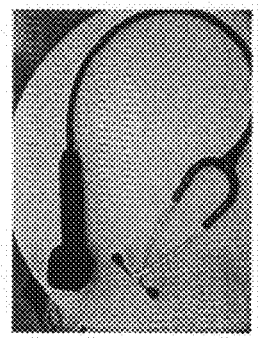
Figure 36: Top view of stethoscope prototype
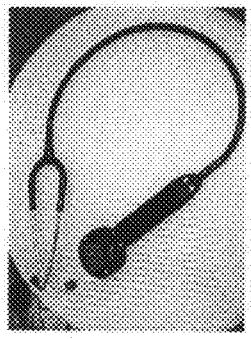
Figure 37: Bottom view of stethoscope prototype
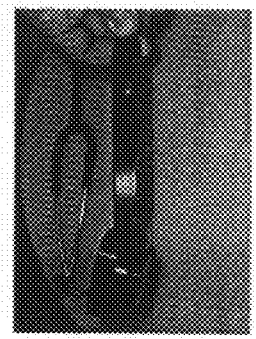
Figure 38: Side view of stethoscope prototype

METHOD AND SYSTEM FOR MANAGING PHYSIOLOGICAL SYSTEM

CROSS-REFERENCE TO RELATED APPLICATIONS

This application is a continuation of PCT Application No. PCT/CA2005/001412 filed on Sep. 15, 2005, which claims the benefit of Canadian Patent Application No. 2,481,631, filed Sep. 15, 2004, and the benefit of U.S. patent application Ser. No. 11/174,366, filed Jul. 1, 2005. The disclosures of the above applications are incorporated herein by reference.

FIELD

The present disclosure relates to signal processing, more specifically to a method and system for processing physiological data and managing a physiological system associated with the physiological data.

BACKGROUND

The statements in this section merely provide background information related to the present disclosure and may not constitute prior art.

In the last few decades, various electrical or electro-mechanical systems have been invented that assist the human physiological system. Some artificial systems like electrocardiogram (ECG), electroencephalograph (EEG), electromyogram (EMG), and stethoscope only collect physiologically relevant information for further analysis by human experts. Others like hearing aids and cochlear implants assist our physiological system by pre-processing input signals to compensate for a defect in the physiological system. In both mentioned artificial systems the processes involved are not controlled by the physiological system, nor do they control the physiological system. The third class of artificial systems are systems that control a physiological system by providing inputs to it and measuring its output to achieve a desired performance by the physiological system, which are referred to as "physiological system management" (PSM). The PSM systems can also collect, store and process physiological information. Examples of these systems are Cardiac Rhythm Management (CRM) systems, Epilepsy and Seizure prediction and control, and Automatic Drug Delivery (ADD) systems. The CRM systems, such as pacemakers and Implantable Cardioverter Defibrillators (ICDs), control the heart cardiac activity by monitoring and analyzing heart activity and providing device therapy in form of electrical stimulus when needed. The ADD systems also monitor one or more physiological parameter (such as blood glucose levels) and deliver proper drug therapy when necessary.

The process in the PSM generally starts with physiological information collection (sensing). The information might be directly processed to tune a set of physiological stimuli if needed. In some situations, the information might be transformed to some other form (such as frequency-domain, time-frequency domain, wavelet features) in order to simplify the decision-making and control process. As a result, certain features might also be extracted from the physiological information. The ultimate goal of the signal transformation and feature extraction is to achieve an optimal representation of the underlying physiological phenomena that is distinctively representative of each phenomenon as much as possible, and is also minimal in terms of computations and storage. Once proper features are obtained that efficiently discriminate various physiological phenomena (for example various causes of heart arrhythmia), a control mechanism can operate to generate proper therapy to the physiological system (like a pace-making stimulus to the heart) and further continue the control process until the physiological system achieves the desired response.

Evidently, the processing in the PSM has to be on-line and in synchrony with the physiological system. Also, many types of PSM systems are implanted inside the human body, or are carried by wearer. As a result, power consumption and/or physical size pose serious constraints on most PSM systems. For example ICDs and pacemakers have to operate reliably inside the body with a minimum power for many years. This by itself severely limits the choice of signal processing, control strategy, and device therapy in the PSM systems. While complicated methods exist for off-line physiological signal processing, they might not be applicable to the PSM systems due to their demand on battery power, and physical size. In the meantime, it is crucial to adapt an optimal domain transformation and feature extraction methodology since the whole control strategy and system performance depends on proper signal representation. It is a major challenge in PSM design to come up with optimal signal representation given power and size constraints.

Various time-domain, frequency-domain, and time-frequency transformation methods have been proposed for PSM systems and for physiological signal processing in general.

Signal processing applied to ECG signal has been an active field of research for more than 30 years. Specially, QRS detection has been the main focus of the research. A through review of the research in this field is provided in [Ref. 5]. Afonso et al. [Refs. 6, 7, 8] discloses methods which are based on offline subband processing of the ECG signal after decomposition of the signal into subbands by a perfect reconstruction (PR) QMF filterbank.

In CRM systems, the input signals include ECG, heartbeat (in form of sound or pressure), and electrogram (EGM) obtained via intracardiac sensors. Often signals are converted to an electrical time-domain waveform. Human experts are able to analyze and interpret the waveforms to achieve a diagnosis. However, for an artificial system, direct interpretation is not often possible. Rather the signal has to be further analyzed to extract certain features that are understandable by the signal processing and control mechanism. This is termed signal transformation and feature extraction. For example, the ECG signal may be analyzed to extract the periodicity information, and detect patterns of P, QRS, and T waves from time-domain data. Alternatively, a frequency transformation followed by spectral analysis or a type of time-frequency analysis such as wavelet transform maybe employed to detect P, QRS, and T-waves and to analyze the periodicity information.

A normal cardiac rhythm sensed by EGM is composed of P-waves (due to atrial depolarization), R-wave (due to ventricular depolarization) and T-wave (due to ventricular repolarization). While various arrythmias might occur alone or together in the heart, it is essential to be able to (at least) distinguish between three classes: 1) arrythmias that are ventricular-based (such as ventricular tachycardia (VT) and ventricular fibrillation (VF)), and 2) arrythmias that are supraventricularly initiated such as atrial-based arrythmias (atrial tachycardia (AT) and atrial fibrillation (AF)) and generally supra-ventricular tachycardia (SVT), 3) Sinus Rhythm (SR) that could be high due to physical activity or stress. While VT and VF are potentially deadly and may be treated with defibrillation (powerful shock delivery), SVT is less dangerous and could be treated with cardioversion. Inaccurate detection of serious ventricular events will lead to improper device therapy (IDT). IDTs are mostly caused by sinus tachycardia, atrial flutter, and atrial fibrillation. Other causes include myopotentials (contraction of the upper thorax muscles and diaphragm) and T-wave oversensing [Refs. 1, 2, 3]. False detection of VT and VF leads to IDT that is painful to the patient and depletes the ICD battery power more quickly. IDT is also potentially harmful to the patient as it puts the patient at risk of device-induced VT (proarrhythmia) that might be dangerous and hard to detect by the ICD [Refs. 1, 2]. As a result, reduction of IDT is a serious issue facing the ICDs. On the other hand, improper classification of VT/VF as SVT could have deadly consequences due to lack of proper device therapy.

Also, recently device therapy for atrial-based arrythmias has become more common. Due to all of these, dual-chamber ICDs have been proposed that sense from both ventricular and atrial chambers and deliver simultaneous therapies to one or both of the two [Refs. 2, 3]. Moreover, four chamber ICDs have been used to treat the four chambers of the heart. It has been discussed on whether or not the dual chamber ICDs have led to improved performance in terms of sensitivity (whether an event such as VT/VF is detected all the time) and specificity (whether all the events detected as one such VT/VF were indeed the correct one). For example, US patent application 2004/0172067 A1, by Saba discloses a dual-chamber ICD for reduction of IDT as well as for improving the detection performance. On the other hand, T. Kurita et al. confirms the results of three other previous studies that compared to single-chamber ICDs, dual-chamber ICDs fail to reduce the IDTs [Ref. 4]. According to them, the rate of IDTs in modern devices remains at a range of 13%-15%. This is comparable to the 11%-25% rate of IDT reported in [Ref. 1] and their references.

Dual-chamber ICDs can achieve almost 100% correct VTNF detection (VT sensitivity). However, they face other problems such as atria double-counting due to far-field sensing (of R-waves by atrial sensor), atrial undersensing of AF, and ventriculoatria (VA) conduction (retrograde conduction from ventricle to atrium) in VT periods [Ref. 1]. Their sensitivity for supraventricular arrhythmias has been reported to be around 61% as compared to 79% for signal-chamber ICDs. Reference [Ref. 1] concludes that dual-chamber ICDs provide limited but not dramatic reduction in IDTs. As the technology is very complex and the number of available signals is increasing, more capable signal processing is needed. With current methods, correct programming of the dual-chamber ICDs is both difficult and time consuming [Ref. 1]. D. Pfeiffer et al. [Ref. 2] suggests that "over-defibrillation" might grow into a major problem for dual-chamber ICDs in the next few years.

To conclude, it is desirable to improve both the specificity and the sensitivity of event detection (specially VT/SVT/SR discrimination) in ICDs and to reduce IDT.

Many researches have done to detect various events related to the heart performance. Once one or more events such as various arrhythmia are detected, proper action is decided upon. Actions include device therapy such as cardioversion and shock delivery, drug delivery, recording heart activity, or sending warning signals to the patient or a device out of ones body. Early inventions disclosed methods that analyzed the time-domain EGM signals obtained from the intracardiac sensors. Processing methods for implantable anti-arrythmia devices is presented in the U.S. Pat. No. 5,545,186 by Olson et al. Usually time-domain periodicity and waveform morphology analysis is the method of choice for detection of arrhythmia. Various rules and algorithms are presented to event detection and decision making after detection. Morphologic analysis of the QRS complex (also called R-wave in EGM signal) is also suggested as in U.S. Pat. No. 5,447,519 by Peterson. There is evidence that the shape and width of the QRS complex are associated with distinct arrhythmia. Thus, many inventors have tried to exploit this for more accurate event detection. Peterson suggests methods based on discriminating between polymorphic and monomorphic QRS complexes. Time-domain methods that analyze the details of the EGM signal are disclosed in U.S. Pat. No. 5,957,857 by Hartley. Similar time-domain methods are present in U.S. Pat. No. 5,411,529 by Hudrlik.

US Patent application 2003/0204215 A1 by Gunderson et al. discloses remedies to an important issue facing the ICDs, i.e. the oversensing problem. Oversensing means detection of events other than the P-wave, R-wave, or T-wave that occur during the cardiac rhythm. Oversensing could be the result of cardiac or non-cardiac signals. In cardiac oversensing, R-waves or T-waves might be sensed twice (double counted as termed by Gunderson). In non-cardiac oversensing, signals of non-cardiac origin (noise due to myopotentials from muscles tissues, lead fracture and insulation failure, electromagnetic interferences (EMI), etc.) contaminate the cardiac signal and cause a false cardiac detection. In dual-chamber ICDs, far-field signals are potential problems. For example strong R-wave sensed at the right ventricular EGM (VEGM) might interfere with weaker P-waves sensed at the atrial EGM (AEGM) causing far-field R-wave oversensing. Gunderson et al. describe in detail the oversensing problem, and disclose methods of dealing with it, including morphology analysis through template-matching of the EGM signal to verify specific types of oversensing. It is desirable to develop methods of signal processing that are capable of reducing oversensing.

While time-domain and morphological processing of cardiac signals (both ECG and EGM) together with template-matching techniques have had limited success, researchers have been investigating alternative methods for performance improvement. Due to the complex time-varying nature of the cardiac signals, more complicated signal processing techniques have been applied to the signals. However, computation and memory demands of more advanced techniques have prohibited them from being implemented on implantable devices that have very limited computation and processing power available. As a result, most inventions have been limited to off-line processing of ECG or recorded EGM signals.

U.S. Pat. No. 5,109,862 by Kelen et al., discloses methods of employing short-time Fourier Transform (STFT) and Spectrograms to analyze ECG signals to be able to detect abnormalities in the heart and other physiological systems. U.S. Pat. No. 5,425,373 by Causey, discloses methods of off-line signal processing applied to EGM signals. Various signal processing strategies including spectral analysis have been disclosed.

U.S. Pat. No. 5,957,866, by Shapiro et al., discloses the use of short-term fast Fourier transform (FFT), wavelet transform, or any other time-frequency analysis applied to body sounds including the heart beat. Noticing the time-varying behavior of heart and the possibility of time-overlap of multiple cardiac events, U.S. Pat. No. 5,778,881, by Sun et al., discloses the use of Wavelet transform for feature extraction combined with hidden Markov models (HMM's) for modeling various heart events represented in the EGM signal. The methods of course are too complicated for low-resource implementation.

Complicated signal processing techniques have been applied in external defibrillators as disclosed in U.S. Pat. Nos. 6,263,238 B1 and 6,064,906. Methods include spectral analysis, coherence analysis, cepstral processing, FFT, Wavelet transform, and auto/cross-correlation analysis.

US patent application 2002/0058968 A1 by Sun et al., discloses methods that can use frequency domain analysis or correlation methods in an implantable device. They maintain an adaptive table of therapy results to be able to choose the most appropriate therapy from a library of various applied or designed therapies.

Due to the complexity and variability of EGM (and any cardiac) signal, cardiac event detection is a complicated task. Experts have realized that it makes sense to employ more complicated signal processing techniques including better feature extraction and improved modeling techniques for the task. As a result, more advanced signal processing methods have been proposed for cardiac event detection. The methods can be combined with traditional time-domain and morphology analysis techniques.

As explained, feature extraction, modeling, and event detection are complicated methods that have been applied to other signal processing applications such as audio, radar, sonar, and image processing. US patent application 2003/0013974 A1, by Natarajan et al., discloses methods of EGM signal processing to detect myocardial ischemia and/or infraction (MI/I). Various signal processing techniques such as spectral analysis, wavelet transform, and time-frequency analysis are proposed to detect MI/I conditions in the heart. US patent application 2004/0127945 A1, by Collins et al., discloses methods of signal processing for dual-chamber ICDs. The methods include wavelet transform for feature extraction, and cross-correlation for template matching. Finally, U.S. Pat. No. 6,434,417 B1, by Lovett, discloses methods of decomposing cardiac signals into subband components by orthogonal filters. Statistical features are extracted from subband signals and are used for event detection. The employ real-valued subband filters and process real-valued subband signals.

Parallel to development of signal processing for cardiac event detection and cardiac control, inventors have considered event detection and control of autonomic nervous system. The idea is based on the fact that the autonomic nervous system partially controls the heart activity (both rhythm and conduction). As a result, monitoring the heart rate variability (HRV) reveals the balance or imbalance of the autonomic system. Inversely, controlling (electrically or chemically) the autonomic nervous system affects the heart operation and might help prevent or stop cardiac arrhythmia. US patent application 2003/0181951 A1 by Cates, discloses methods that electrically stimulate the autonomic nervous system when an autonomic imbalance is predicted based on heart rate or HRV. While low frequency content of HRV is known to be due to both parasympathetic (or vagal) and sympathetic activity, high frequency content is mostly related to only parasympathetic activity. The ratio of the two frequency contents (LF/HF) thus can be used as a measure of autonomic balance. Cates discloses employment of interval analysis (between the R-waves) to measure the ratio.

US patent application 2004/0098061, by Armoundas et al., discloses methods that combine automatic drug delivery (ADD) with common ICD functions based on beat-to-beat variability in the morphology of the EGM signal.

As reviewed above, there are major problems in current CRM systems and specifically in ICDs and pacemakers that need to be addressed.

Accurate event detection in single-chamber and dual chamber ICDs is desirable. Methods should increase both sensitivity and specificity of detection, to be able to provide safe and reliable device therapy, while reducing IDT, oversensing, and under-sensing as much as possible.

At the same time, it is desirable that methods of feature extraction, event detection, and decision making be simple enough to be implemented on ultra-low resource platforms such as implantable devices.

Processing delay of such methods should be maintained within acceptable ranges for CRM systems.

Feature extraction and event detection methods should provide robustness to various noises and interferences from internal (to human body) and external sources.

It is also desirable that feature extraction of cardiac signal be compatible with signal compression for signal recording and telemetry.

It is well known that epilepsy affects about 1% of the population in the industrialized countries [Refs. 9, 10, 11]. As such, major resources have been dedicated in detection and more importantly prediction of seizures. Upon positive prediction, various therapies such as device therapy, automatic drug delivery (ADD), or human intervention could be applied. Currently, epilepsy is analyzed based on electroencephalogram in various forms such as noninvasive scalp EEG, and invasive Intracranial EEG (IEEG) also known as electrocorticogram (ECoG).

A review of major methods of seizure detection is provided in references [Refs. 9, 10, 11]. To summarize, methods applied depend on how seizure is theorized to be generated and how the EEG signal is classified. The classic theory has been to present the EEG signal (obtained by multiple electrodes) as a multivariate random process. Accepting this view, linear signal processing methods such as autocorrelation-based (or equivalently Fourier-based and spectral methods) are applied to the EEG signal. The newer and more modern view has been to regard the EEG signal as a manifestation of a deterministic chaotic process, with a lower dimensionality during and around seizure periods. Based on this view, nonlinear signal processing and particularly those based on chaos theory are employed. However, most recently researchers [Refs. 9, 10, 11] increasingly avoid simple classification of seizure and its representation in the EEG domain as one of the mentioned two classes (random or deterministic chaotic). They believe while there is considerable nonlinearity in the EEG process, there are also random components in the signal. Also, there is no conclusive evidence to characterize the nonlinearity in the EEG signal as low-dimensional chaotic process. Still the nonlinear approaches seem to yield useful results provided that their limitations are taken into account [Ref. 12]. A thorough review of seizure prediction and control is provided in [Ref. 13]. As noted in [Ref. 13], effective prediction and control of epileptic seizures is an open research topic.

U.S. Pat. No. 5,743,860 by Hively et al. discloses methods of seizure detection based on nonlinear chaotic-based time series analysis such as correlation dimension and minimum mutual information. U.S. Pat. No. 6,549,804 by Osorio et al, discloses a combination on nonlinear filtering methods to perform real-time analysis of the EEG signal for seizure prediction. U.S. Pat. No. 6,735,467 B2 by Wilson, discloses methods of seizure detection based on neural networks and clustering algorithms. U.S. Pat. No. 6,061,593 by Fischell et al. discloses methods seizure prediction based on d-c shift detection in the EEG signal. The method is geared towards an implantable device for epilepsy control. They further elaborate on their implantable device in U.S. Pat. No. 6,473,639 B1.

It is therefore desirable to provide a system and method which is applicable to a wide range of physiological systems to efficiently and appropriately manage the physiological systems.

REFERENCES

[Ref. 1] B. Schaer et al., "Methods of Minimizing Inappropriate Implantable Cardioverter-Defibrrilator Shocks", Current Cardiology Reports 2000, 2:346-352.

[Ref. 2] D. Pfeiffer et al. "Implantable Dual-Chamber Cardioverter-Defibrillator-Pacemaker", Current Cardiology Reports 2000, 2:335-340.

[Ref. 3] R. Schimpf et al., "Algorithms for Better Arrhythmia Discrimination in Implantable Cardioverter Defibrrilators", Current Cardiology Reports 2000, 3:467-472.

[Ref. 4] T. Kurita et al. "Inappropriate Defibrillator Therapies: Do Dual-Chamber Devices Really Provide a Remedy", in Cardiac Arrythmias 2003, edited by A. Raviele, Springer Pub., 2004.

[Ref. 5] B-U Kohler et al., "The principles of software QRS detection", IEEE Eng. In Medicine and Biology, pp. 42-57, January/February 2002 issue.

[Ref. 6] V X Afonso et al. "Multirate processing of the ECG using filter banks", Proc. of IEEE in Computers in Cardiology, pp. 245-248, 1996.

[Ref. 7] V X Afonso et al., "Filter bank-based processing of the stress ECG", trans. of IEEE-EMBC and CMBEC, pp. 887-888, 1997.

[Ref. 8] V X Afonso et al. "ECG beat detection using filter banks", IEEE Trans. Biomed. Eng., vol. 46, pp. 192-202, 1999.

[Ref. 9] Maidwald, Th. et al, "Comparison of three nonlinear seizure prediction methods by means of the seizure prediction characteristic", Physica D, 194 (15 Jul. 2004) 357-368.

[Ref. 10] McSharry, P. E., et al., "Comparison of predictability of elliptic seizures by a linear and a nonlinear method", IEEE Trans. on Biomed. Eng., vol. 50, no. 5, May 2003, pp. 628-633.

[Ref. 11] Lai, Y-C et al, "Correlation-dimension and autocorrelation fluctuations in epileptic seizure dynamics", Physical Review, vol. 65, pp. 031921: 1-5, Mar. 2002.

[Ref. 12] Lehneritz, K. et al., "Seizure prediction by nonlinear EEG analysis", IEEE Eng. In Medicine And Biology magazine, January/February 2003, pp. 57-63.

[Ref. 13] Iasemidis, L. D., "Epileptic seizure prediction and control", IEEE trans. on Biomedical Eng., vol. 50, no. 5, May 2003.

SUMMARY

It is an object of the invention to provide a system and method that obviates or mitigates at least one of the disadvantages of existing systems.

According to an aspect of the present invention, there is provided a system for implementing physiological system management (PSM) including: one or more signal acquisition modules for collecting physiological information from one or more physiological systems to provide one or more input signals; a plurality of Weighted Overlap-Add (WOLA) analysis filterbanks for decomposing the one or more input signals, each converted into K (possibly complex-valued) subband signals; a subband processing module for processing the subband signals in subband domain, including: a detection module for detecting one or more events occurring in the one or more physiological systems based on the subband signals, and a decision making module for make a decision on a control measure based on the subband signals, and a controller for applying the control measure to the one or more physiological systems.

According to a further aspect of the present invention, there is provided a method of implementing physiological system management (PSM), including the steps of: collecting physiological information from one or more physiological systems to provide one or more input signals; decomposing the one or more input signals, each converted into K (possibly complex-valued) subband signals; detecting one or more events occurring in the one or more physiological systems based on the subband signals; making a decision on a control measure based on the subband signals; and applying the control measure to the one or more physiological systems.

According to a further aspect of the present invention, there is provided a computer readable medium having recorded thereof statements and instructions for executing by a computer to carry out the method of implementing PSM. According to a further aspect of the present invention, there is provided a carrier wave embodying a computer data signal representing sequences of statements and instructions for executing the method of implementing PSM.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 36 illustrates a top view of the prototype of the stethoscope of FIG. 32;

FIG. 37 illustrates a bottom view of the prototype of the stethoscope of FIG. 32;

FIG. 38 illustrates a side view of the prototype of the stethoscope of FIG. 32.

DETAILED DESCRIPTION

Figure 1:
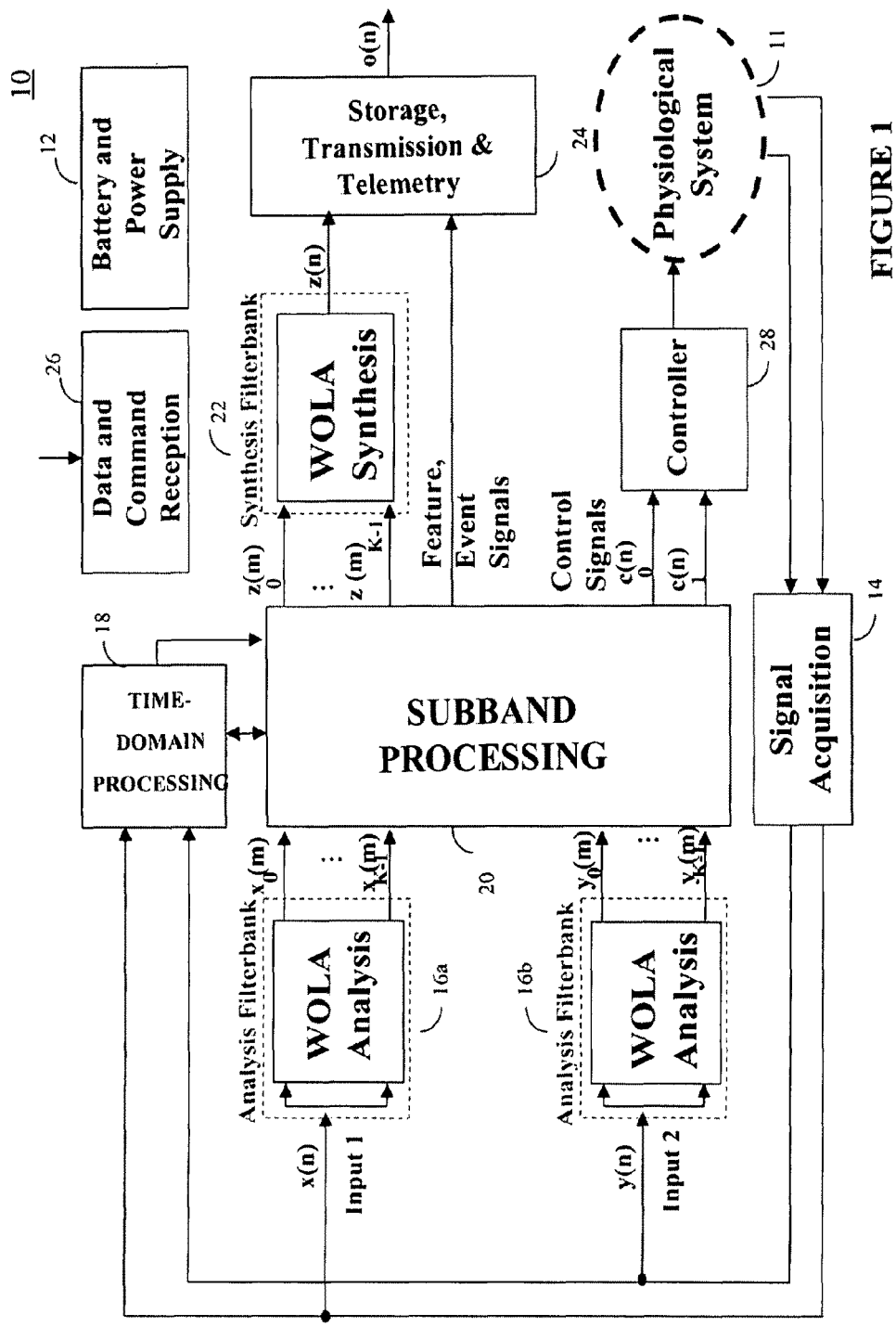
FIG. 1 illustrates a system for physiological system management PSM in accordance with an embodiment of the present invention.

The following description is merely exemplary in nature and is not intended to limit the present disclosure, application, or uses. It should be understood that throughout the drawings, corresponding reference numerals indicate like or corresponding parts and features.

FIG. 1 illustrates a system 10 for physiological system management (PSM) in accordance with an embodiment of the present invention. In the PSM system 10, a multiplicity of input signals is decomposed in subband domain by a multiplicity of Weighted-Overlap Add (WOLA) analysis filterbanks (AFBs) 16a, 16b. Subband processing 20 is implemented to the outputs from the WOLA analysis filterbanks 16a, 16b. The subband processing includes, for example, signal enhancement and feature extraction that may be different in various subbands, as well as subband-based event detection and possibly decision making. The results of the subband processing 20 may also possibly be combined with a time-domain processing 18, and the decision making being done based on the results of both subband and time-domain event detection. As a result of the decision making process, various actions may take place, including device therapy, drug delivery, signal compression and/or storage, event recording, activating a warning system out of the body, or no action. The WOLA filterbanks are disclosed in U.S. Pat. Nos. 6,236,731 and 6,240,192, which are incorporated herein by reference.

In the description, "input signal" and "information signal" may be used interchangeably, and each may includes a possible physiological signal. In the description, "physiological signal" and "physiological information" may be used interchangeably.

In FIG. 1, a physiological system 11 is to be monitored and controlled by the PSM system 10. The physiological signals obtained from the physiological system 11 may be, but not limited to, cardiac signals including, ECG/EKG signals, EGM signals, heart beats (including fetal heart beats), lung sounds, bowel/gastrointestinal sounds, electroencephalogram (EEG), electromyogram (EMG), or any other signals relevant to physiological activities. The physiological system 11 may be any system or part of a living body that can be observed, analyzed and possibly controlled.

Without loss of generality, some examples of the physiological system 11 are the heart, lungs, brain, muscles, the nervous system, the neuromuscular system of muscle control, and the autonomous system.

In FIG. 1, one physiological system 11 is shown as example. However, the PSM system 10 may be applied to more than one physiological system. The PSM system 10 may manage one or more than one physiological system based on physiological information collected from the one or more than one physiological system.

The physiological signal processing and management implemented by the PSM system 10 are applicable in a wide range of technology areas including heartbeat and lung signal analysis/synthesis provided by stethoscopes or ECG devices, processing electrogram (EGM) signals, analyzing physiological activities such as neurological activities, or any other time-domain input signals.

A signal acquisition block 14 is provided to acquire proper signals from the physiological system 11. The signal acquisition block 14 includes a plurality of sensors for obtaining signals from the physiological system 11, signal conditioning and amplification circuitry, filtering, sampling and analog-to-digital conversion (A/D) to obtain time-domain input signals x(n) and y(n). For example, the signal acquisition block 14 may include intracardiac sensors for the CRM application. In the description, the terms "block" and "module" may be used interchangeably.

In FIG. 1, two time-domain input signals x(n) and y(n) are shown as example. However, it is apparent to a person skilled in the art that the number of time-domain input signals is changeable.

The digital input signals x(n) and y(n) are processed by the WOLA analysis filterbanks 16a and 16b to obtain a set of K (possibly complex-valued) subband signals per input signal. In FIG. 1, these subband signals are labeled as $x_k(m)$ and $y_k(m)$, k=0, 1, ..., K−1. In FIG. 1, two WOLA analysis filterbank 16a and 16b are shown. However, the number of WOLA analysis filterbanks is changeable.

The subband signal sets (one per input signal) are processed by the subband processing block 20. At the same time, the input signals x(n) and y(n) are processed by the time-domain processing block 18.

Figure 2:
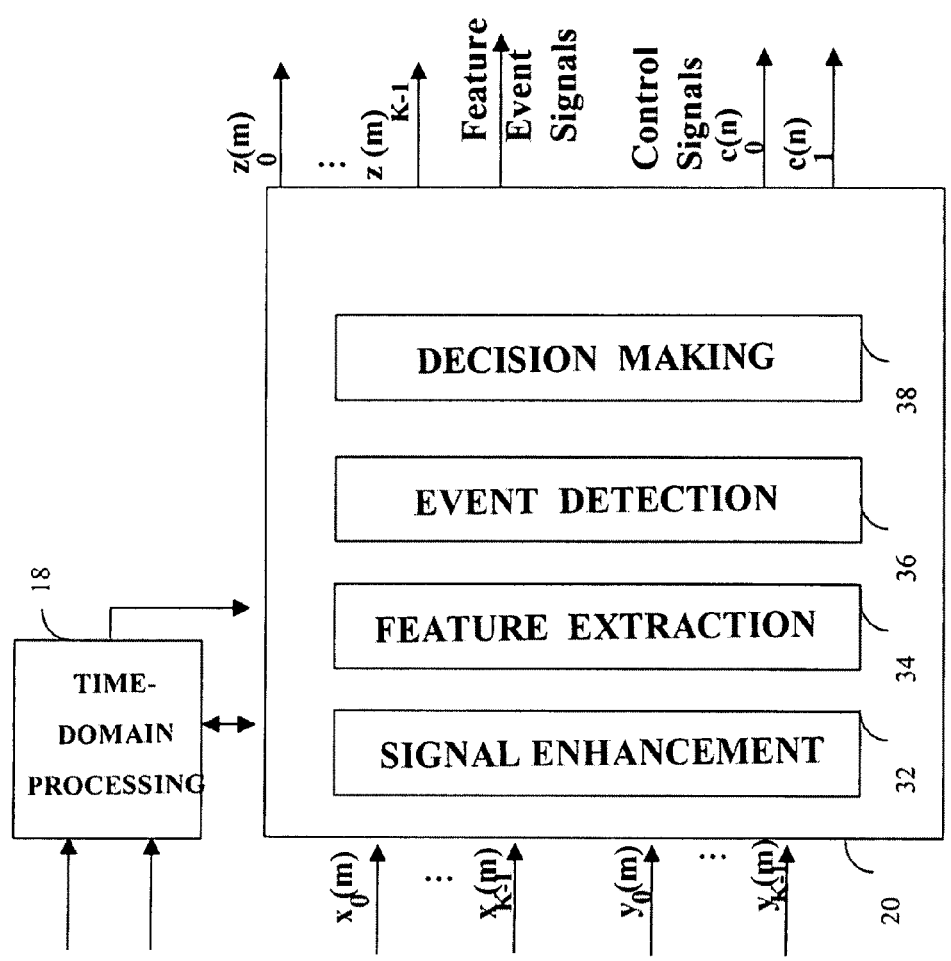
FIG. 2 illustrates one example of a subband processing and a time-domain processing blocks of FIG. 1.

FIG. 2 shows one example of the processing stages in the subband processing block 20 of FIG. 1. The subband processing block 20 of FIG. 2 includes a signal enhancement block 32, a feature extraction block 34, a event detection block 36 and a decision making block 38.

The signal enhancement block 32 of FIG. 2 processes the subband signals in the subband domain to remove unwanted noise or interference and to enhance desired signal features. Then, subband-based feature extraction is applied by the feature extraction block 34. Any type of appropriate subband feature extraction is applicable. For example, the subband feature extraction may include subband energy tracking, subband autocorrelation and cross-correlation, extraction of spectral features, extraction of features such as correlation-dimension for nonlinear signal processing, or combinations thereof. Based on the extracted features, event detection is accomplished by the event detection block 36. For example, in the CRM application, the event detection block 36 may detect the probability of certain arrhythmias, such as VT/VF, AT, or AF happening. Based on the event detection results, and the results of the time-domain processing 18, the decision making block 38 implements decision-making process. For example, in the CRM application, the decision making block 38 decides whether shock therapy (defibrillation), cardioversion, drug delivery, or no action is to be done.

As a result of the decision-making, a set of control signals $c_0(n)$ and $c_1(n)$ are generated. In FIGS. 1-2, two control signals $c_0(n)$ and $c_1(n)$ are shown as example. However, the number of the control signals is changeable.

Referring to FIG. 1, the set of control signals $c_0(n)$ and $c_1(n)$ are applied to an adaptive controller 28 that controls the physiological system 11 in various ways. In the CRM application, the controller 28 may do tasks such as cardioversion and defibrillation by applying electric signals to the heart through electrodes, or other tasks as needed.

The controller 28 operates in closed-loop or in open-loop. In closed-loop operation, by monitoring the input signals from the physiological system 11, the controller 28 adjusts control measures and adapts the control strategy based on evaluation of the applied control measures. The evaluation/adapting process may be implemented by the decision making block 38.

The time-domain processing block 18 and subband processing block 20 may interact with each other to adapt each other's processing strategies if needed. Also, the results of the time-domain processing in the time-domain processing block 18 are sent to the subband processing block 20 for joint decision-making in the subband processing block 20 as described above.

The subband processing block 20 also generates signals that include extracted features, and events detected. The signals may include warnings to be transmitted to out of body by a block 24 of FIG. 1.

The subband processing block 20 also generates one or more processed subband signal sets. In FIGS. 1-2, the processed subband signal sets are labeled as $z_k(m)$, k=0, 1, ..., K−1. WOLA synthesis filterbank 22 processes the one or more processed subband signal sets to re-synthesize them and generates the time domain signal z(n).

In FIG. 1, one WOLA synthesis filterbank 22 is shown. However, more than one WOLA synthesis filterbank may be used. In FIG. 1, one time-domain signal z(n) is shown as example. However, more than one time-domain signal may be generated as a result of the synthesizing process.

Advantageously, the re-synthesized signal can be processed in subband domain to obtain a signal less contaminated by noise and interference.

The feature and event signals together with the synthesized time-domain signal z(n) are further processed by the block 24 in FIG. 1. The block 24 implements signal processing which may include signal coding and compression, and may include a storage for future use by the PSM system 10 or a storage and/or transmission to out of the PSM system 10 (e.g. out of body) for on-line or off-line processing and telemetry for monitoring the PSM system 10.

A battery and power supply circuitry 12 provides battery and regulated power supply to the whole system 10. The status of various parts of the overall implantable system including the PSM system 10, the battery and power supply circuitry 12, and other components is also monitored in the block 24 for telemetry and transmission to outside.

The PSM system 10 can be programmed and controlled (on-line or off-line) from outside by sending data and/or commands to a data and command reception block 26. The data and/or commands may be received in form of electrical transmission, magnetic, or other forms. Based on the data/commands inputs, the data and command reception block 26 changes the system setup, processing or a combination thereof. For example, a command may be sent to the data and command reception block 26 by placing a magnet externally on the PSM system 10 to close or open certain switches that control the processing. Other means of controlling the PSM system 10 through the data and command reception block 26, such a radio-frequency (RF) transmission, is also applicable.

The WOLA-based subband processing efficiently decomposes signals into almost orthogonal subbands. As a result, various processing strategies could be independently applied to individual subbands. This is distinct from block-wise frequency-domain methods since the WOLA filterbank can be designed to offer desirable subband isolation, aliasing and distortion, without the need to resort to long block sizes as is the case in block-wise frequency-domain processing.

The WOLA-based subband processing offers lower delay and processing latency compared to frequency-domain methods. The WOLA-based PSM 10 can ensure event detection and potential therapy in due time.

Due to near-orthogonal subband decomposition, various events might be easier to detect in individual or groups of subband. For example, noise and interference might contaminate only a few subbands leaving other subbands signals free of noise for processing. Periodic cardiac signals appear in a number of subbands providing better opportunities for signal processing. Various cardiac events such as VT, VF, AT, and AF are easier to detect in subband domain as their underlying generation mechanism and propagation patterns are different.

Subband processing 20 provides for parallelism in signal processing. This will eventually lead to more robust and faster processing and decision-making. At the same time, flexibility is provided by the ability to employ different strategies/parameters in individual or groups of subbands.

Signal enhancement and compression can be done more efficiently in WOLA subband domain.

The WOLA-based PSM 10 can be efficiently implemented on an ultra-low resource hardware platform as disclosed in U.S. Pat. Nos. 6,236,731 and 6,240,192; WO 98/47313; R. Brennan and T. Schneider, "A Flexible Filterbank Structure for Extensive Signal Manipulations in Digital Hearing Aids", Proc. IEEE Int. Symp. Circuits and Systems, pp. 569-572, 1998; US patent application Publication Nos. 20030063759 and 20030110033. Although the advantages of subband processing have been known for years, algorithmic complexity that leads to high computation cost and formidable power consumption has prevented their usage in most implantable devices. The WOLA filterbank hardware platform provides the opportunity to employ sophisticated subband-based signal processing techniques.

The WOLA filterbank offers flexible configuration that could be optimized based on the application at hand for the processing delay, frequency resolution, and computation cost.

Various complicated signal processing tasks such as speech and audio signal enhancement, single and multiple-input noise reduction, speech pattern recognition, audio and music compression, directional signal processing, and subband adaptive filters (SAFs) have already been efficiently implemented on the WOLA filterbank. The PSM system 10 can benefit from the existing methods or can be combined in series or in parallel to one or more of those methods. For example, WOLA-based noise reduction can be applied as a preprocessing stage for PSM. Alternatively, WOLA-based subband coding could be employed for cardiac signal compression.

Figure 3:
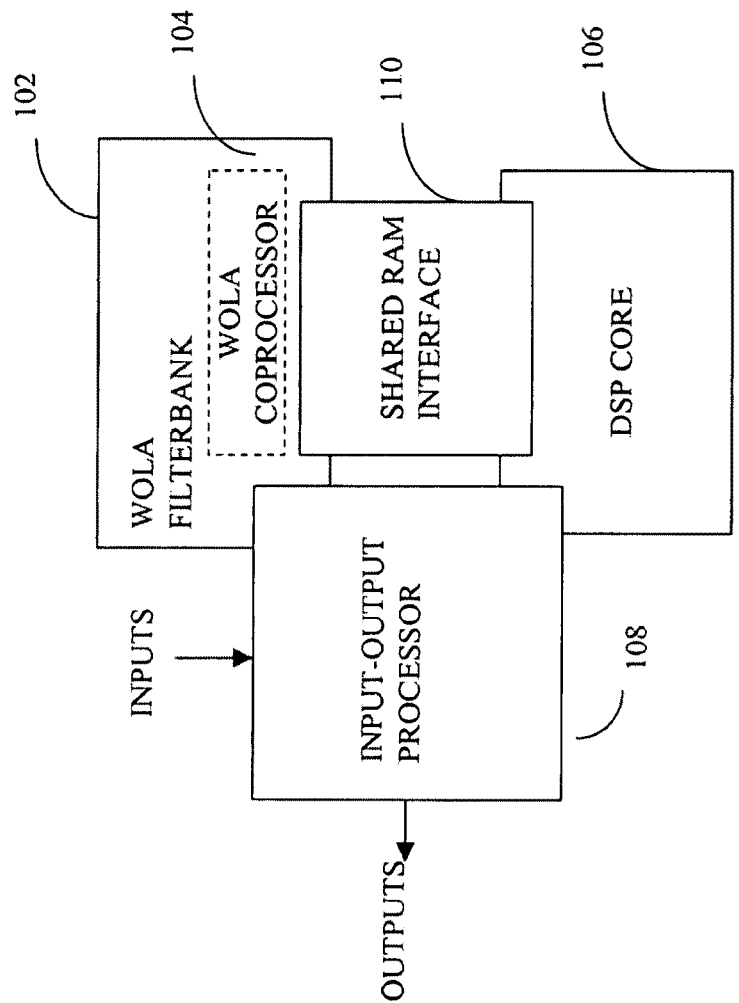
FIG. 3 illustrates an example of a platform of an WOLA filterbank.

FIG. 3 illustrates a platform 100 on which the whole or a part of the system 10 of FIG. 1 can be implemented. Major parts of the system 10 can be efficiently implemented on the ultra-low resource hardware platform 100 (referred to as DSP system 100). Particularly, blocks 16a, 16b, 18, 20, and 22 of FIG. 1 may be implemented on the DSP system 100. Parts of the block 24 (compression and storage) and the block 14 (pre-filtering and A/D) of FIG. 1 may also be implemented on DSP system 100. Details of the DSP system 100 are described in U.S. Pat. Nos. 6,606,391 and 6,236,731. It is noted that any other implementation of WOLA-based PSM is also possible.

The DSP system 100 includes a WOLA filterbank system 102 having a WOLA coprocessor 104, a DSP core 106, and an input-output processor (IOP) 108. The WOLA filterbank system 102, the DSP core 106, and the IOP 108 are capable of operating in parallel. The parallel operation of these components enables the implementation of complex signal processing algorithms with low system clock rates and low resource usage and is adept at subband signal processing. It may be adapted to generate critically-sampled, real-valued filterbanks for a CODEC (e.g. 394 of FIG. 35) as described below.

The WOLA filterbank 102 is microcodeable and includes "time-window" microcode to permit efficient multiplication of a waveform by a time-domain window, the WOLA filterbank 102, and data memory. The configurable WOLA coprocessor 104 efficiently splits the full band input signals into subbands, leaving the core free to perform other algorithm calculations. For example, the WOLA coprocessor 104 may be an 18-bit block floating point WOLA filterbank coprocessor, and the DSP core 106 may be a 16-bit fixed-point DSP core. The WOLA filterbank 102 may operate as the oversampled WOLA filterbank as described in U.S. Pat. Nos. 6,236,731 and 6,240,192.

The programmable DSP core 106 enables it to implement time-domain algorithms that are not directly implementable by the WOLA coprocessor 104. This adds a degree of reconfigurability.

The IOP 108 is responsible for transferring and buffering incoming and outgoing data. The IOP 108 may receive information from analog/digital (A/D) converter (not shown). The output of the IOP 108 may be supplied to a digital/analog (D/A) converter (not shown).

RAM 110 includes two data regions for storing data of the WOLA filterbank 102 and the DSP core 106, and a program memory area for the DSP core 106. Additional shared memory (not shown) for the WOLA filterbank 102 and the IOP 108 is also provided which obviates the necessity of transferring data among the WOLA filterbank 102, the DSP core 106 and the IOP 108.

Figure 4:
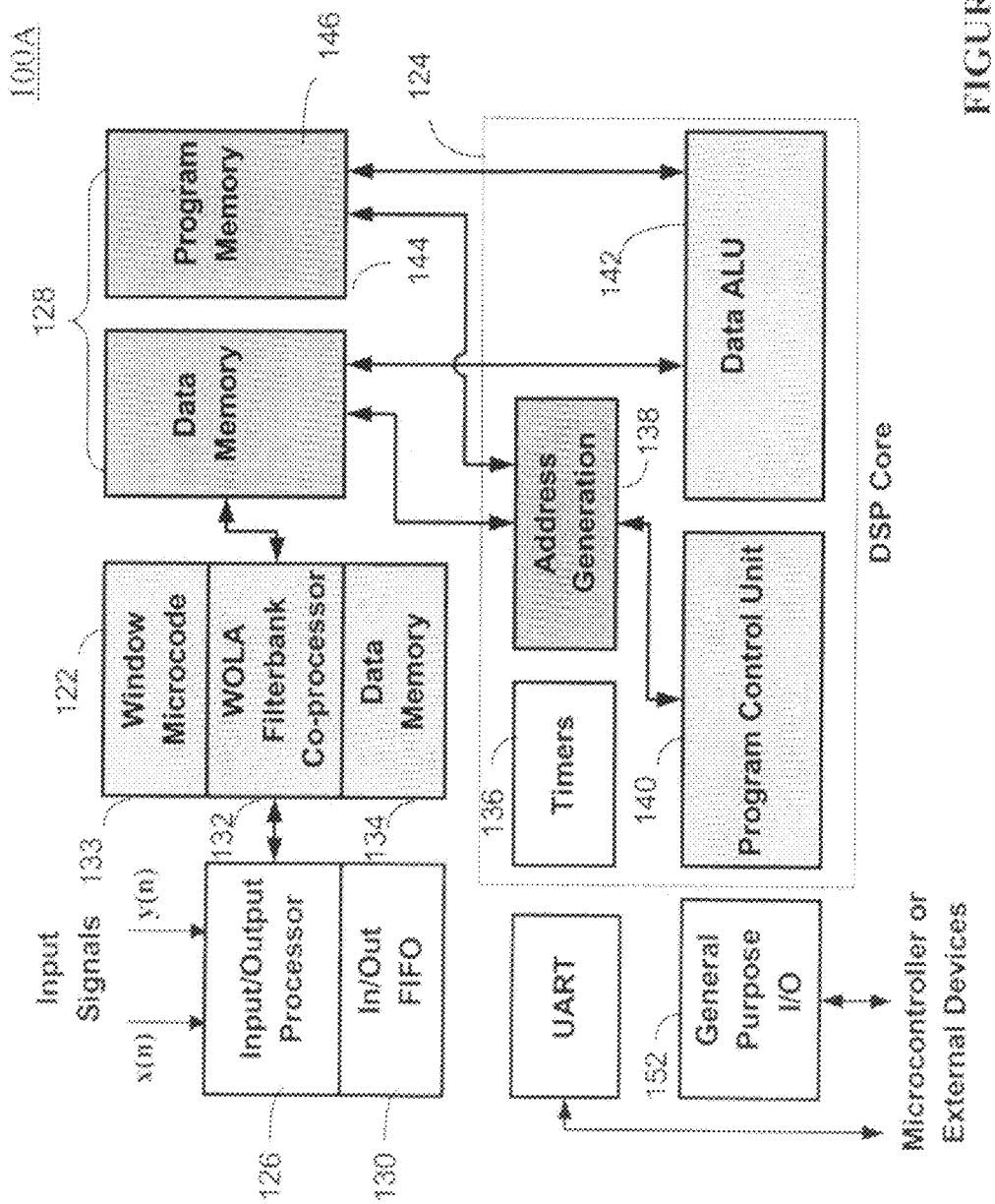
FIG. 4 illustrates an example of the platform of FIG. 3.

FIG. 4 illustrates one example of the DSP system 100 of FIG. 3. The DSP system 100A of FIG. 4 includes a microcodeable WOLA filterbank 122, a 16 bit fixed point DSP core 124. The input-output processor (IOP) 126 and Random Access Memory (RAM) 128. The WOLA filterbank 122, the DSP core 124 and the IOP 126 are operable in parallel.

The IOP 126 obtains digitalized input signals and processes them. The outputs from the IOP 126 are provided to a first-in-first-out buffer (FIFO) 130.

The WOLA filterbank 122 includes a WOLA filterbank co-processor 132, and data memory 134. The WOLA filterbank 122 may operate as an oversampled WOLA filterbank as described in U.S. Pat. Nos. 6,236,731 and 6,240,192. The WOLA filterbank 122 is microcoded 133, for example, for performing windowing operations, and Fast Fourier Transform (FFT) and vector multiplications, which are included in the oversampled WOLA process.

The DSP core 124 includes timers 136, an address generation module 138, a program control unit 140, and a data Arithmetic and Logical Unit (ALU) 142. The DSP core 124 enables the system the implementation of time-domain algorithms that are not directly accomplishable by the WOLA co-processor 132 thereby adding a degree of re-configurability.

The RAM 128 includes a data memory 144 for storing data for the DSP core 124 and the WOLA filterbank 122, and a program memory space 146 for storing the program for the DSP cores 124.

The DSP system 100A communicates with outside world, such as microcontroller or external devices, through a UART (serial port) 150, general-purpose input/output (I/O) pins 152 and an interface (not shown) dedicated to a signal, such as physiological signal.

The I/O pins 152 can be used for performing actions as a result of recognizing commands, and for receiving addition input signals, regardless of a whether the microcontroller is available or not. The microcontroller may further process the outputs from the DSP system 100A to control one or more systems (not shown).

For example, the I/O pins 152 may include an input pin(s) which is used to receive an input(s). The input pin may be connected to switches to allow commands, such as commands for starting/ending the physiological management, starting/ending feature extraction, starting/ending offline processing, etc. The I/O pins 152 may include a visual output pin(s) which is connected to devices, such as displays, LEDs, which provide visual output to a user. For example, the visual output pin is used to inform the user of the current state of the system (e.g. feature extraction, event detection, decision making etc). The I/O pins 152 may include an action output pin 156 which can be connected to various output devices. For example, when the DSP system 100A recognizes a physiological signal, it activates one or a combination of these pins to drive one or more external devices.

Referring to FIG. 1, an example of the WOLA-based PSM system 10 for the CRM application is described in detail. The input signals x(n) and y(n) are, for example, electrogram signals sensing activity from the atrial and ventricular chambers of a person's heart. After WOLA analysis by the analysis filterbanks 16a and 16b, subband signal sets are delivered to the subband processing block 20.

In the CRM application, typically event detection is robustly performed. The PSM system 10, which implements a WOLA-based detection method, can reliably perform the desired cardiac event detection. The PSM system 10 clearly and quickly detects and discriminates Sinus Rhythm, Tachychardia, Fibrillation, Flutter, lead failure and dislodgement. For simplicity, one possible WOLA-based processing is described. However, other potential WOLA processing methods and configurations are also applicable.

In this case, the time-domain signal x(n) in FIG. 1 is an EGM signal. Assume the time-domain EGM signal x(n) in FIG. 1 is analyzed to obtain K subband signals $x_k(m)$, k=0, 1, ..., K−1 that are then grouped into G subband groups (G less than or equal to K). Each subband group includes one or more subband signals. Next, to obtain subband energy signals $E_g(m)$, g=0, 1, ..., G−1, absolute values (or squared absolute values) of subband signals $x_k(m)$ in each group are calculated and added together.

Figure 5:
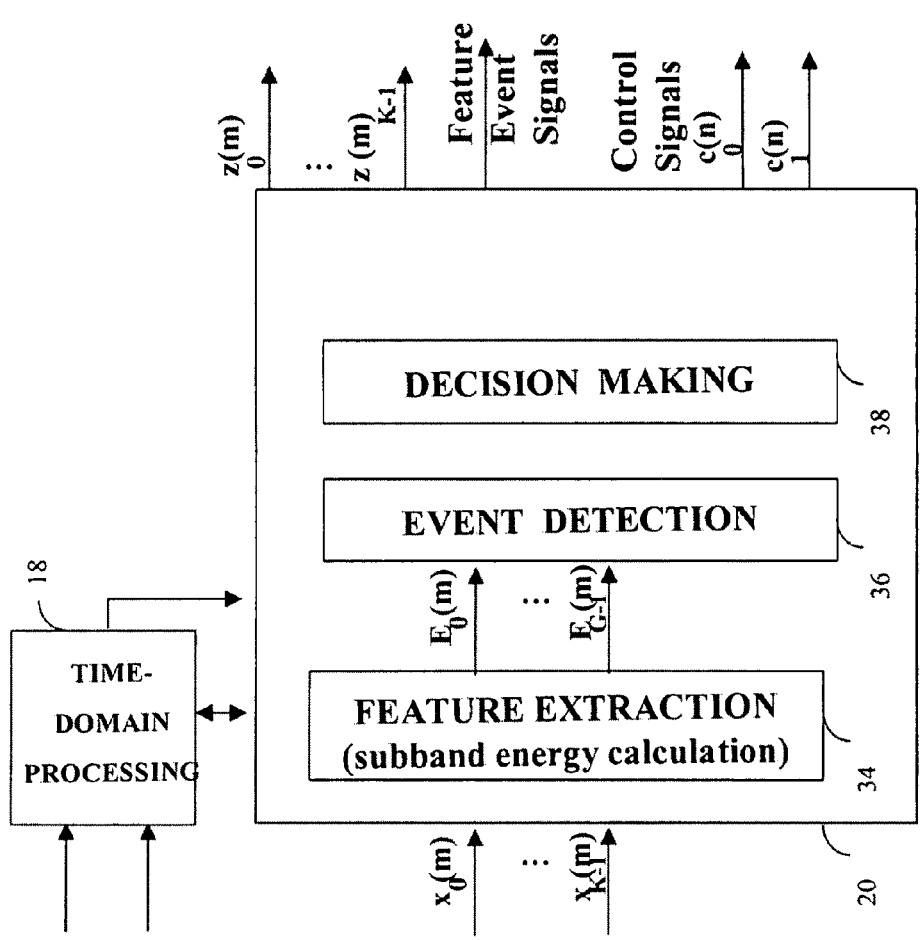
FIG. 5 illustrates a further example of the signal processing and the time-domain processing blocks of FIG. 1.

FIG. 5 illustrates an example of the subband processing block 20 of FIG. 1 which is suitably applied to the CRM application. In FIG. 5, one set of subband input signals $x_k(m)$, k=0, 1, ..., K−1 is shown for clarity.

The feature extraction block 34 of FIG. 5 implements subband energy calculation to output subband energy signals $E_g(m)$, g=0, 1, ..., G−1. The purpose of grouping subband signals is to reduce data and signal processing load to an optimum point, and at the same time, to reduce undesired variability and artifacts as much as possible. While various grouping strategies are possible, only one will be described here.

A prominent depolarization (in atrium or ventricle) will result in an abrupt change in the time-domain EGM signal. In the time-frequency domain of WOLA-subband energy signals $E_g(m)$, this will lead to a synchronous activity increase across various subband groups g=0, 1, ..., G−1. Exploiting this synchrony ensures reliable detection of CRM events.

Noise and artifacts may contaminate one ore more subband groups. However, their effects are primarily confined to only a few subband groups and do not induce sustained and prominent synchronous activity across subband.

As depolarization turns into a chaotic pseudo-periodic pattern (as in fibrillation), the synchrony across the subband groups will be greatly decreased.

Periodic signals (and pseudo-periodic signals, i.e. signals that are periodic only for short-term segments) without prominent depolarizations does not induce sustained synchronous activity across subband groups. For example, a perfectly sinusoidal signal will result in a slow-varying signal (or a DC signal) only in the subband group that covers the sinusoid frequency. Other subband groups will not exhibit any synchronous activity.

WOLA analysis includes an overlap-add to obtain the subband signal. As a result, there is a high degree of overlap between the time-domain data x(n) used to obtain the analysis vectors $x_k(m)$, k=0, 1, ..., K−1 at consecutive time instances (m−1, m, m+1). Typically L samples of x(n) are analyzed to obtain one vector of $x_k(m)$. Then data is advanced in time by R samples to obtain the next L sample of x(n). As a result, consecutive data frames share as much as L-R samples. Typical values of L and R (used in this embodiment) are L=128 and R=8. Due to this highly overlapping analysis, artifacts, glitches, and noise will be averaged out of WOLA analysis representation. At the same time, the overlap leads to superior representation of periodic signals, such as heartbeats.

WOLA-based analysis of EGM signals is described in detail using the results of experiments designed to demonstrate WOLA-based processing of EGM signals for the CRM event detection. The employed EGM data is the Ann Arbor Electrogram Libraries, Ann Arbor Mich., USA, referred to as AAEL here. Two EGM electrode data are used: Bipolar Ventricular Lead inserted at Right Ventricular Apes (RVAb signal in AAEL), and Bipolar Atrial Lead inserted in High Right Atrium (HRAb signal in AAEL). The EGM data is first downsampled to 250 Hz, and high-pass filtered to remove components below 1 Hz. Next, the absolute value of the difference function is employed as input to WOLA processing.

WOLA analysis setup was (1) Analysis window length: L=128 (Brennan window) (2) Number of subbands: 32, K=31 (17 unique subband due to Hermitian symmetry); (3) Odd-stacked FFT; (4) Number of subband groups: 7, G=6

Subband groups were designed to group the subband energies as summarized in Table 1. Group 1 was ignored to minimize the low-frequency noise and artifacts. Other grouping strategies are also possible.

TABLE 1

Subband grouping strategy

| Subband Group | Subband Range | Freq. Range |
|---|---|---|
| 1 | 1 | Very Low-Freq. |
| 2 | 2, 3, 4 | Low-Freq. |
| 3 | 5, 6 | Low Freq. |
| 4 | 7, 8, 9 | Mid-Freq. |
| 5 | 10, 11, 12 | Mid-Freq. |
| 6 | 13, 14 | High-Freq. |
| 7 | 15, 16, 17 | High-Freq. |

Figure 6:
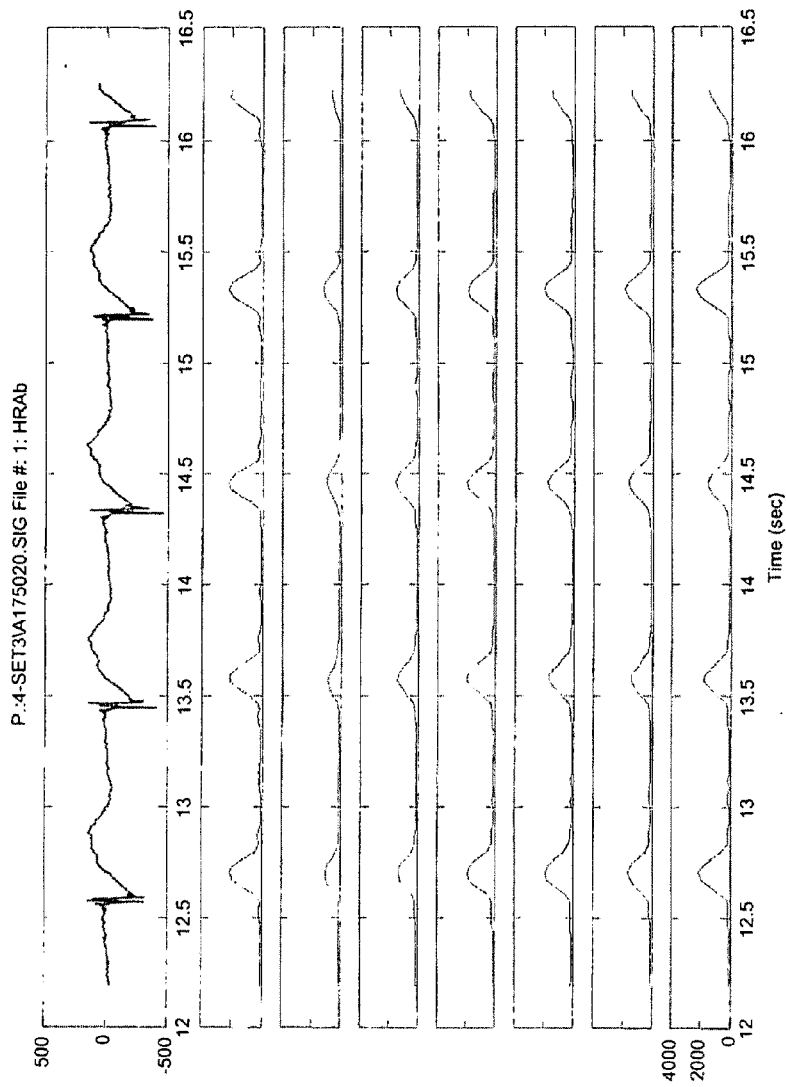
FIG. 6 illustrates HRAb signal (top), and subband energies (7 bottom rows) for a normal SR.

FIG. 6 shows a typical normal HRAb EGM signal (on top) with its associated WOLA subband energy signals in seven groups. As depicted, there is a synchronous rise in energy across subbands for every heartbeat. Beat-to-beat tracking is obviously simple to do based on the synchronous energy patterns. However, EGM patterns even for normal rhythm can be more complicated.

Figure 7:
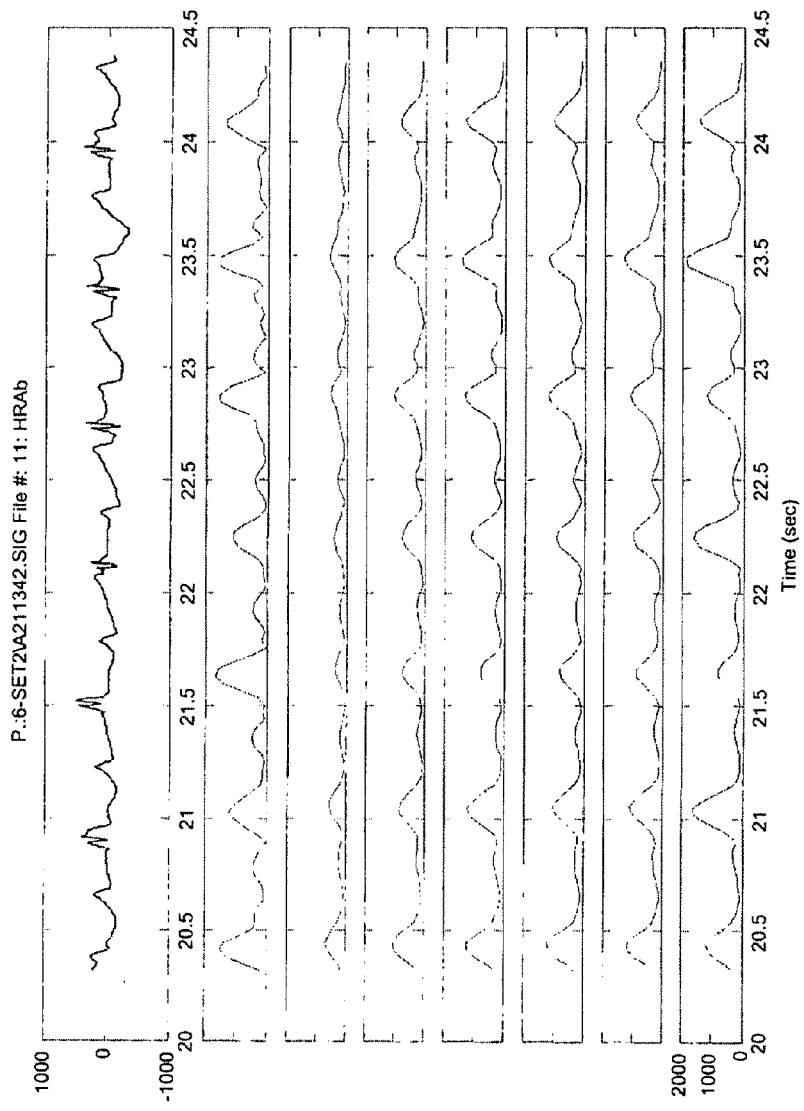
FIG. 7 illustrates HRAb signal (top), and subband energies (7 bottom rows) for a normal SR complicated time-domain pattern.

FIG. 7 depicts an example of SR with complicated time-domain pattern. As evident, in spite of beat-to-beat morphology variation, the subband energies clearly mark the beat locations.

Various periodicity and peak-tracking algorithms may be employed to extract the beat locations in subbands. In the experiments, a maximum-average tracking method was used to extract the beat locations in subbands. The method tracks the maximum value with a first-order Infinite Impulse Response (IIR) filter with two time-constants, TauMax1 and TauMax2. Similarly, an IIR filter tracks the average with two time constants TauAvg1 and TauAvg2.

The following MATLAB code shows how the method works. When the input (inp(t), the input subband energy signal) exceeds the average by a certain ratio (AvgRatio1), and exceeds a certain ratio (MaxRatio1) of the maximum value, a peak is detected. To avoid detection of spurious peaks when the average and the peak are very close to each other (for example when there is no activity for a long time), the average should be less than a certain ratio (MaxRatio2) of the maximum value for a peak to be declared.

```
          TauAvg1=.5;TauAvg2=.7;TauMax1=.2;TauMax2=.95;
          MaxRatio1=.5;
MaxRatio2=.9;AvgRatio=1.1;
for t=1:L,   % Do it for all time samples of subband energy
   if inp(t)>avg_old
      avg(t)=avg_old*TauAvg1+inp(t)*(1-TauAvg1);
         if    (inp(t)>AvgRatio*avg_old)    &
         (inp(t)>MaxRatio1*Max_old)    &
         (avg_old<MaxRatio2*Max_old),
            peak(t)=inp(t);
         end
   else
      avg(t)=avg_old*TauAvg2+inp(t)*(1-TauAvg2);
   end;
   avg_old=avg(t);
   if inp(t)>Max_old,
      Max(t)=Max_old*TauMax1+inp(t)*(1-TauMax1);
   else
      Max(t)=Max_old*TauMax2+inp(t)*(1-TauMax2);
   end;
   Max_old=Max(t);
end;
```

Figure 8:
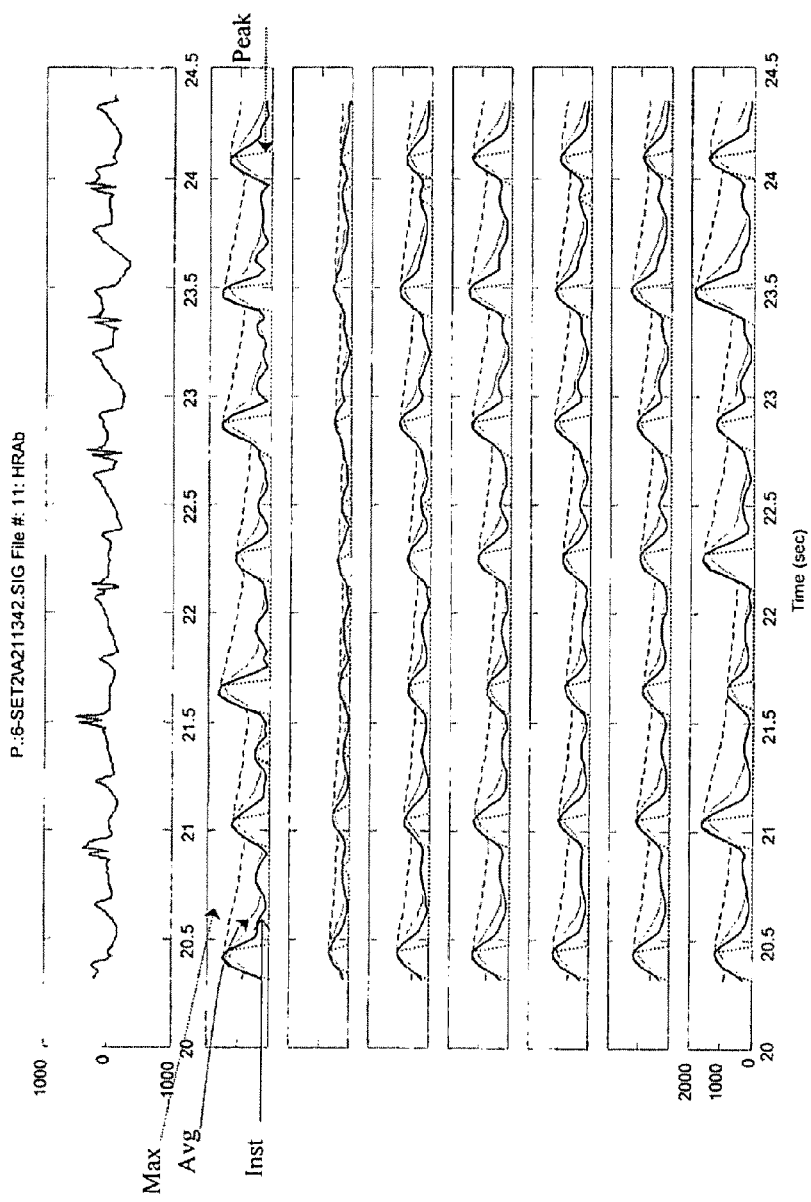
FIG. 8 illustrates the EGM signal (top row) together with 7 subband energies (rows 2-8)

FIG. 8 shows the peak-tracking performance of the algorithm for the energy signals of FIG. 7. For each subband energy group, the maximum, average, and the instantaneous values are shown along with the detected peak signal. In FIG. 8, "Max" (dashed line) represents the maximum value, "Avg" (solid-thin line) represents the average value, "Inst" (solid-thick line) represents the instantaneous value, and a dotted line denotes a detected peak.

In the next step in beat detection, the detected peak signal is converted to a binary signal (1 for peak and 0 otherwise). To robustly detect beats, a search is done for a binary pattern through the binary peak signal. A pattern of [1,1,1,0] was sought for a conservative detection (a peak that lasts at least for three subband time-samples) while a pattern of [1,0,0] was sought for a more aggressive detection. At the place of each detected peak, a binary signal of width two ([1,1] pattern) was then placed. The width of two (rather than one) helps to avoid artifacts when peaks are detected in various subbands with only one sample delay or advance between subbands.

Figure 9:
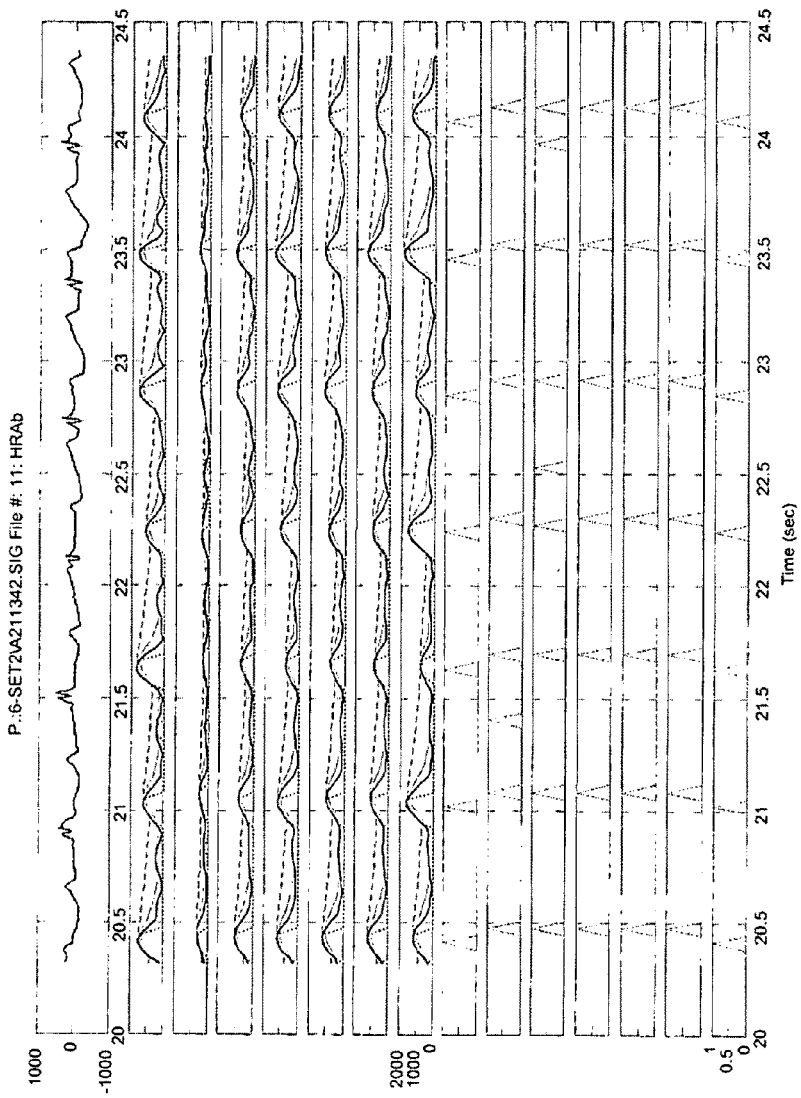
FIG. 9 illustrates Peak detection for EGM signal (top row) of FIG. 8, EGM peak signals (7 bottom rows): 1: 1-Con, 2: 1-Agg, 3:2&3-Agg, 4: 4&5-Agg, 5: 5&6-Agg, 6: Det-Agg, 7: Det-Con.

Next, the subband peaks are to be combined to exploit the synchrony of the subband energies. Since the peak signals are converted to 0/1 patterns, cross-correlation is simplified as a simple logical AND operation. We classified band groups into tree frequency ranges, low-frequency (LF), mid-frequency (MF), and high frequency (HF), as shown in Table 1. If a peak is initially detected in two (out of three) frequency ranges (for example in LF and MF bands, i.e. subband energy groups of 2, 3, 4, 5) a peak pulse is generated. This is implemented by simple logical AND/OR operation on detected subband binary peak signals. Finally, the falling edge of the peak pulse provides the beat location. FIG. 9 depicts the detected peaks pulses associated with EGM signal of FIGS. 7 and 8. There are seven detected peaks signals. It is noted that in the rows 2-8 of FIGS. 9-13, a dashed line denotes the maximum signal, a solid-thin line denotes the average signal, a solid-thick line denotes the instantaneous signal and a dotted line denotes the detected peak signal. The rows 2-8 in FIGS. 9-13 illustrate various EGM signals as described below. The top row shows the EGM signal itself.

In the description, the following notations are used for detected peaks.
1. 1-Con, first subband energy with conservative detection
2. 1-Agg, first subband energy with aggressive detection
3. 2&3-Agg, logical AND of binary peaks of band groups 2 and 3 with aggressive detection
4. 4&5-Agg, logical AND of binary peaks of band groups 4 and 5 with aggressive detection
5. 5&6-Agg, logical AND of binary peaks of band groups 5 and 6 with aggressive detection
6. Det-Agg, final detected peaks for aggressive detection
7. Det-Con, final detected peaks for conservative detection As shown, extra peaks have appeared on detected peak 2&3-Agg, however, are absent in the final results due to AND operation. The bottom two rows of the figure provide the final detected peaks. Peaks 1-Con and 1-Agg are ignored in final decisions as mentioned before.

Figure 10:
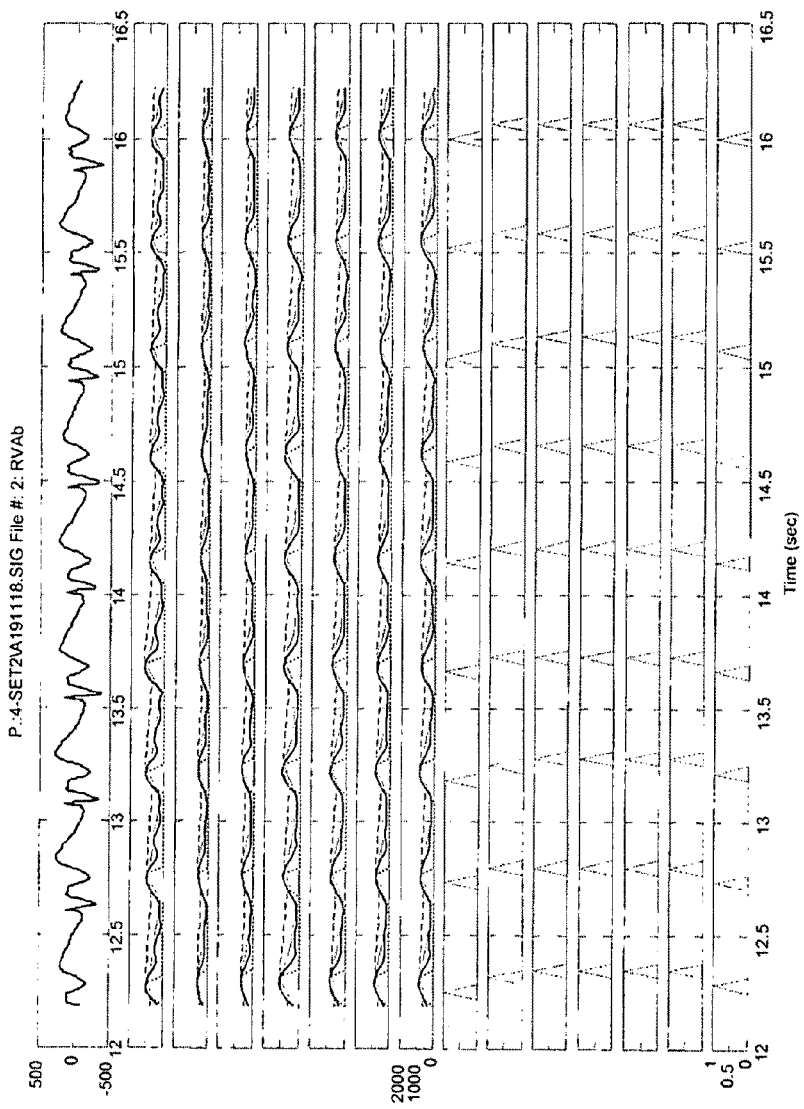
FIG. 10 illustrates Peak detection for EGM signal (top row) of a VT segment, EGM peak signals (7 bottom rows): 1: 1-Con, 2: 1-Agg, 3:2&3-Agg, 4: 4&5-Agg, 5: 5&6-Agg, 6: Det-Agg, 7: Det-Con.

To further demonstrate the detection performance, we provide more results. FIG. 10 shows the detected peaks for a VT segment with wide R-waves. As demonstrated both Det-Agg and Det-Con peaks are all correct in spite of waveform morphology complications.

Figure 11:
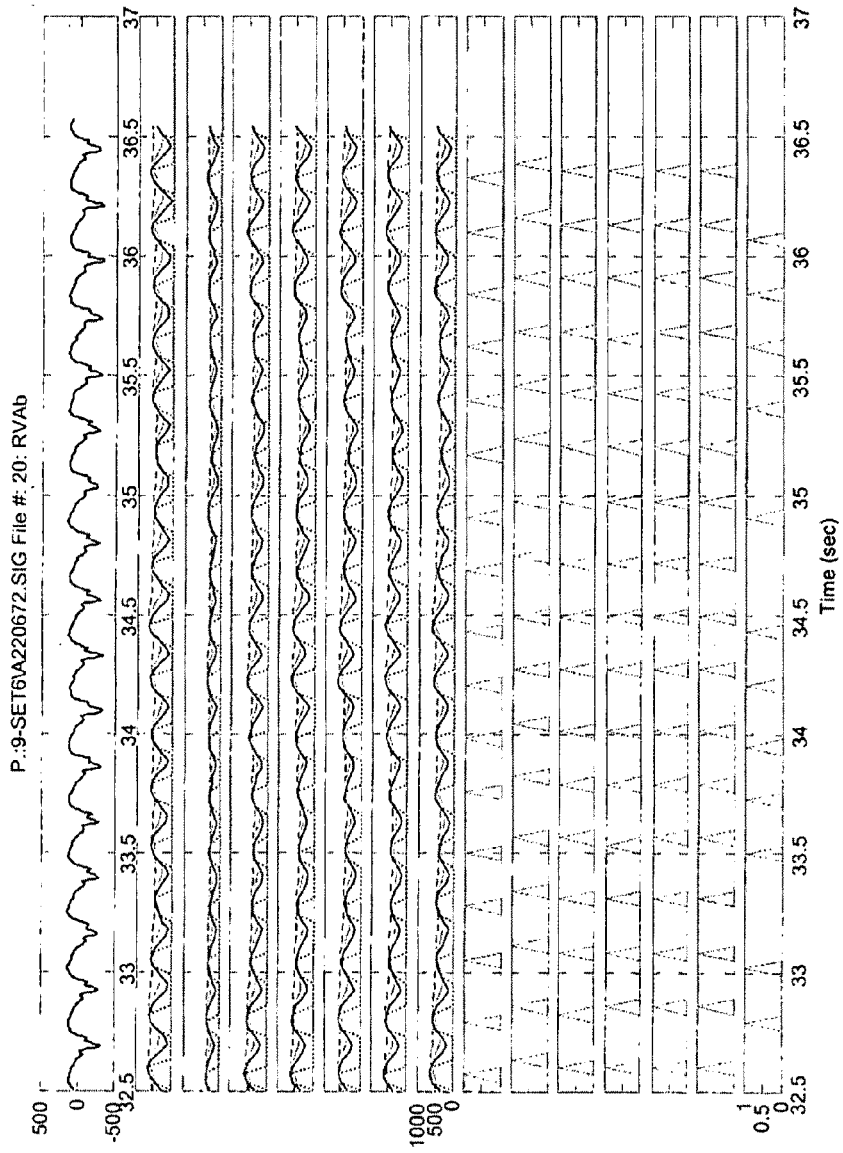
FIG. 11 illustrates Peak detection for EGM signal (top row) of a VFt segment, EGM peak signals (7 bottom rows): 1: 1-Con, 2: 1-Agg, 3:2&3-Agg, 4: 4&5-Agg, 5: 5&6-Agg, 6: Det-Agg, 7: Det-Con.

FIG. 11 depicts how Ventricular Flutter (VFt) is represented in peak patterns. It is evident that the synchrony between the bands is still strongly present. As a result, Det-Agg detects all the peaks (17), the peaks all periodically located. However, conservative detector detects less peaks (12). This is a consistent representation of VFt by the algorithm.

Figure 12:
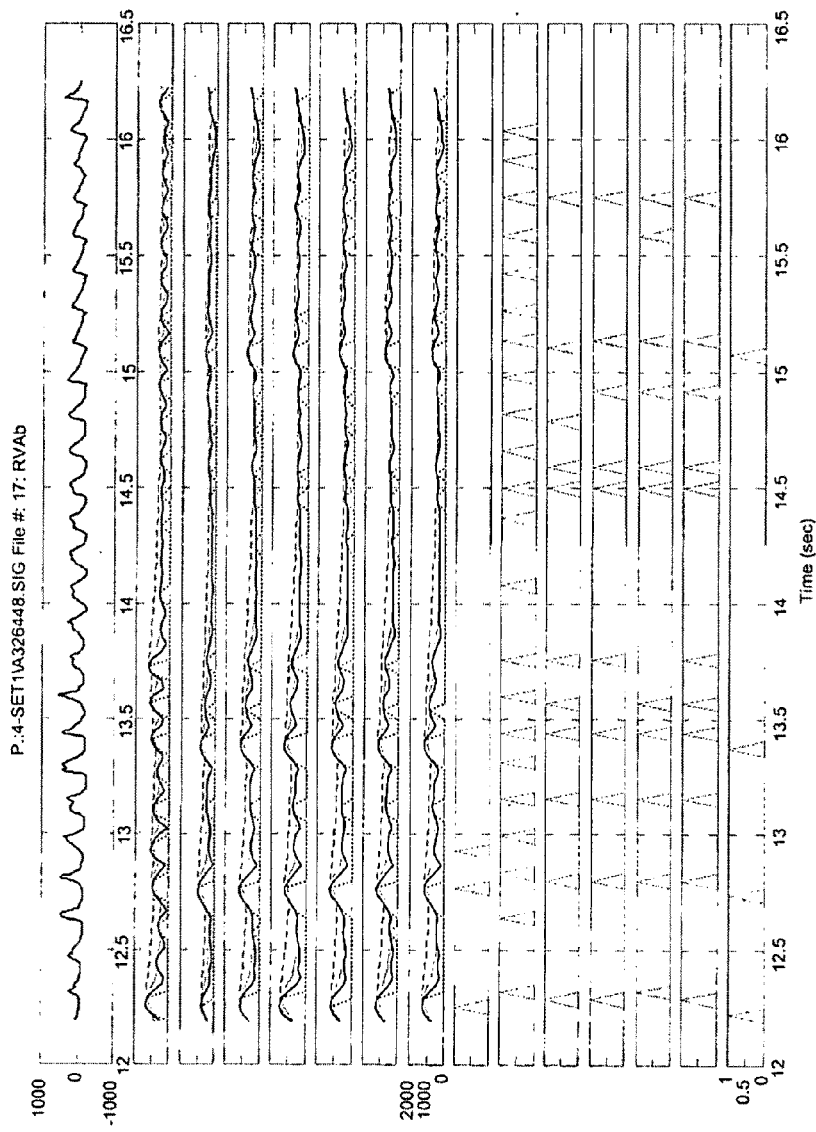
FIG. 12 illustrates Peak detection for EGM signal (top row) of a VF segment, EGM peak signals (7 bottom rows): 1: 1-Con, 2: 1-Agg, 3:2&3-Agg, 4: 4&5-Agg, 5: 5&6-Agg, 6: Det-Agg, 7: Det-Con.
Figure 13:
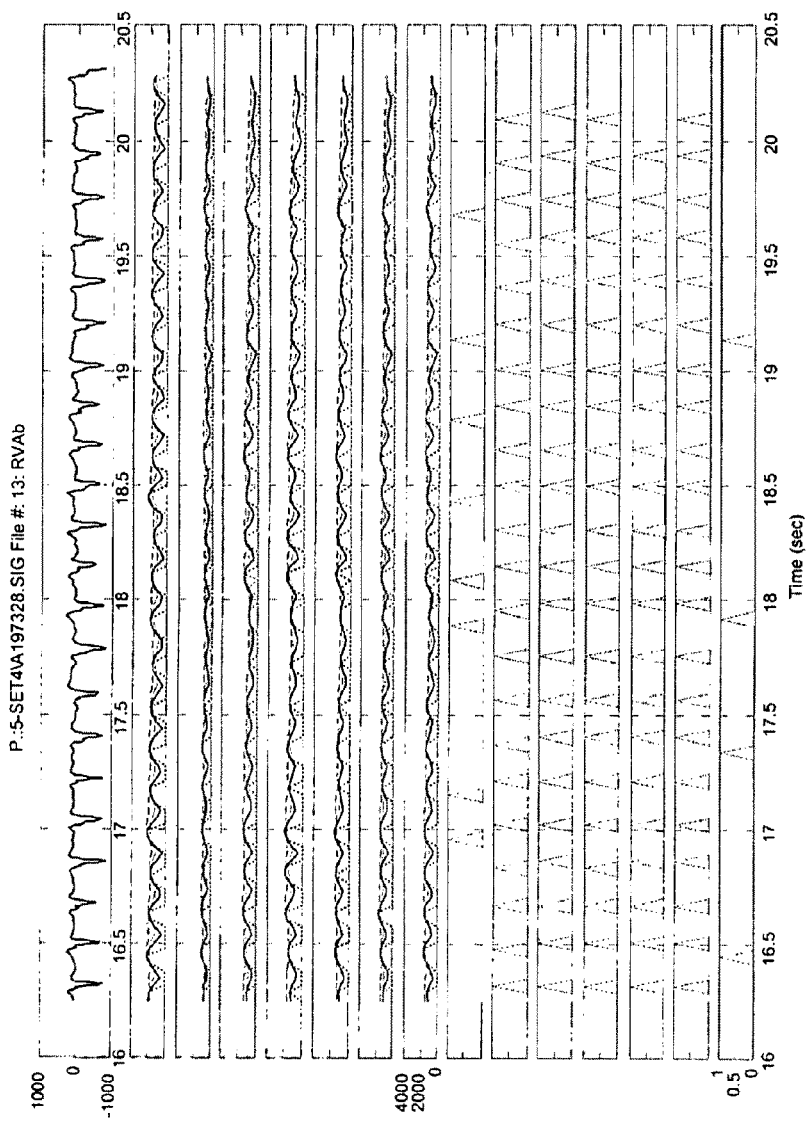
FIG. 13 illustrates Peak detection for EGM signal (top row) of a VF segment, EGM peak signals (7 bottom rows): 1: 1-Con, 2: 1-Agg, 3:2&3-Agg, 4: 4&5-Agg, 5: 5&6-Agg, 6: Det-Agg, 7: Det-Con.
Figure 14:
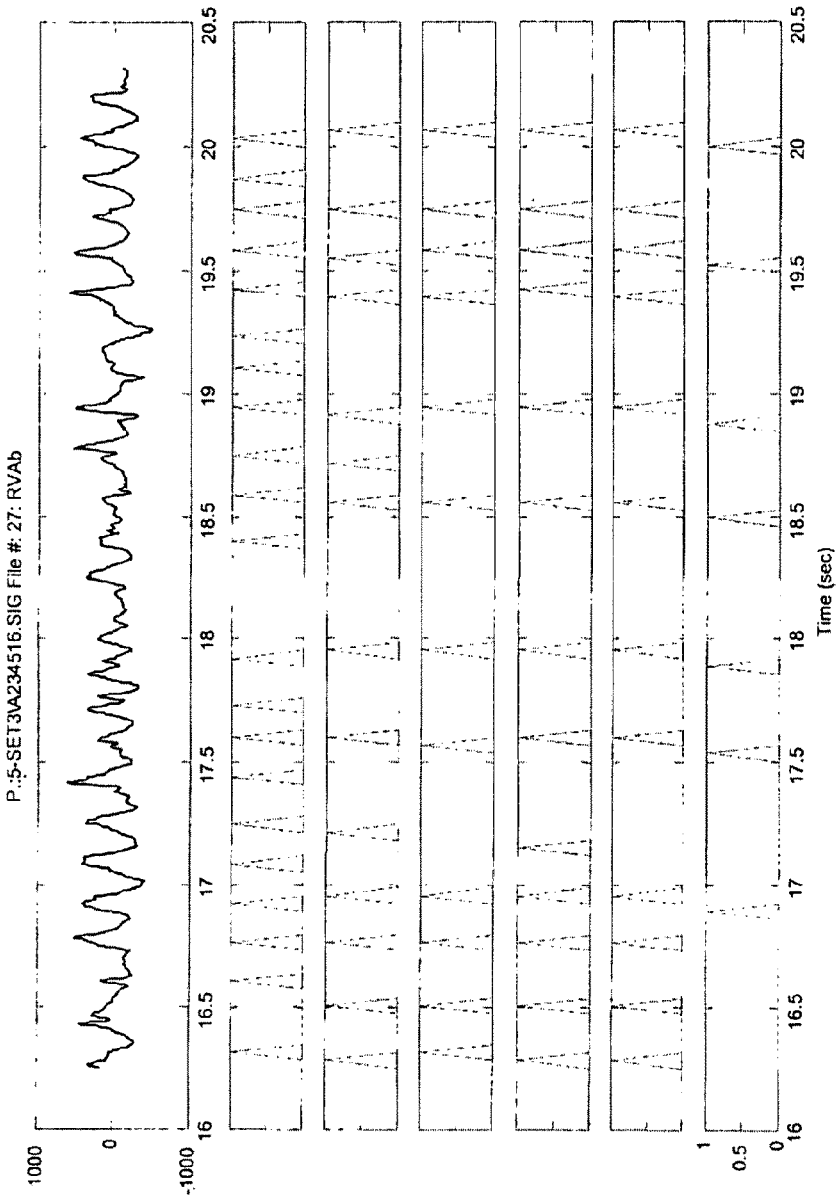
FIG. 14 illustrates Peak detection for EGM signal (top row) of a VF segment, EGM peak signals (6 bottom rows): 1: 1-Agg, 2:2&3-Agg, 3: 4&5-Agg, 4: 5&6 Agg, 5: Det-Agg, 6: Det-Con.
Figure 15:
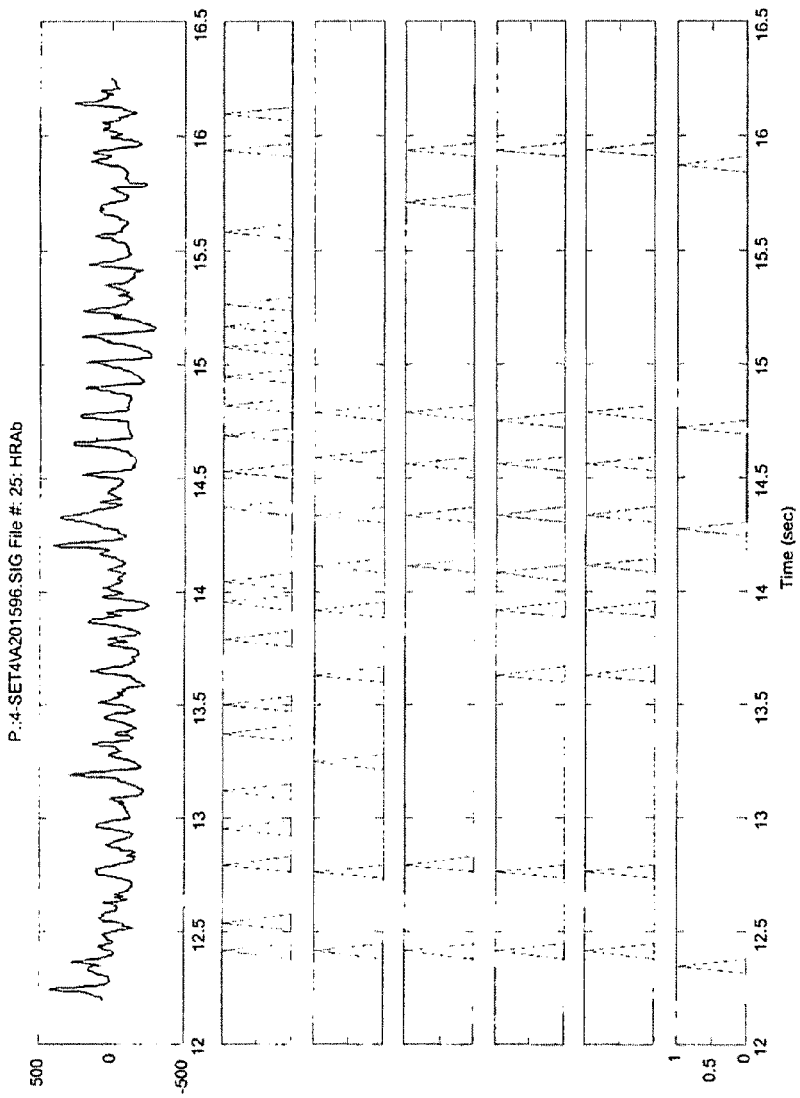
FIG. 15 illustrates Peak detection for EGM signal (top row) of an AF segment, EGM peak signals (6 bottom rows): 1: 1-Agg, 2:2&3-Agg, 3: 4&5-Agg, 4: 5&6 Agg, 5: Det-Agg, 6: Det-Con.
Figure 16:
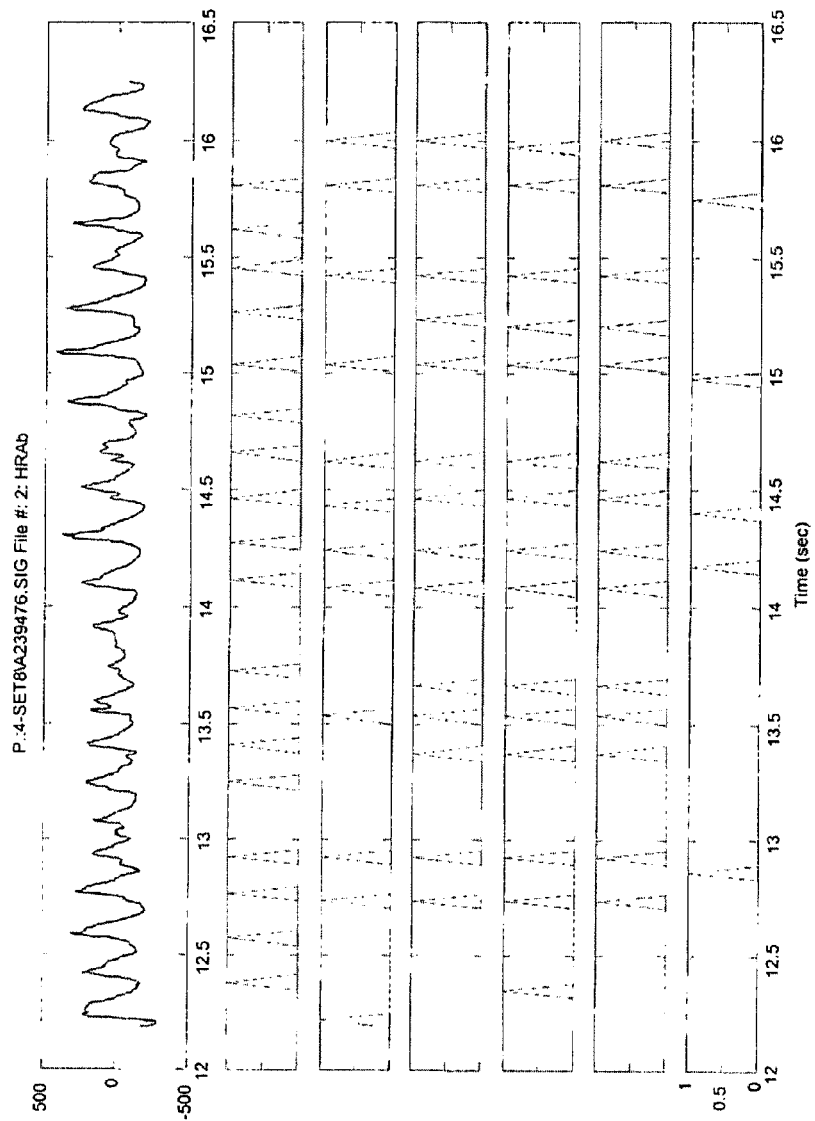
FIG. 16 illustrates Peak detection for EGM signal (top row) of an AF segment, EGM peak signals (6 bottom rows): 1: 1-Agg, 2:2&3-Agg, 3: 4&5-Agg, 4: 5&6 Agg, 5: Det-Agg, 6: Det-Con.

FIGS. 12-14 demonstrate how VF is represented in the WOLA subband group energies. As shown, the Det-Con signal shows very few peaks while the Det-Agg signal might show a lot of peaks. Generally it is observed that in a progression from VFt to VF, first there will be much less peaks detected by the Det-Con than Det-Agg and, second the periodicity of Det-Agg pulses may also become distorted if the EGM become random. AF representation by subband energies is very similar to VF. FIGS. 15 and 16 depict two typical representation of AF.

Figure 17:
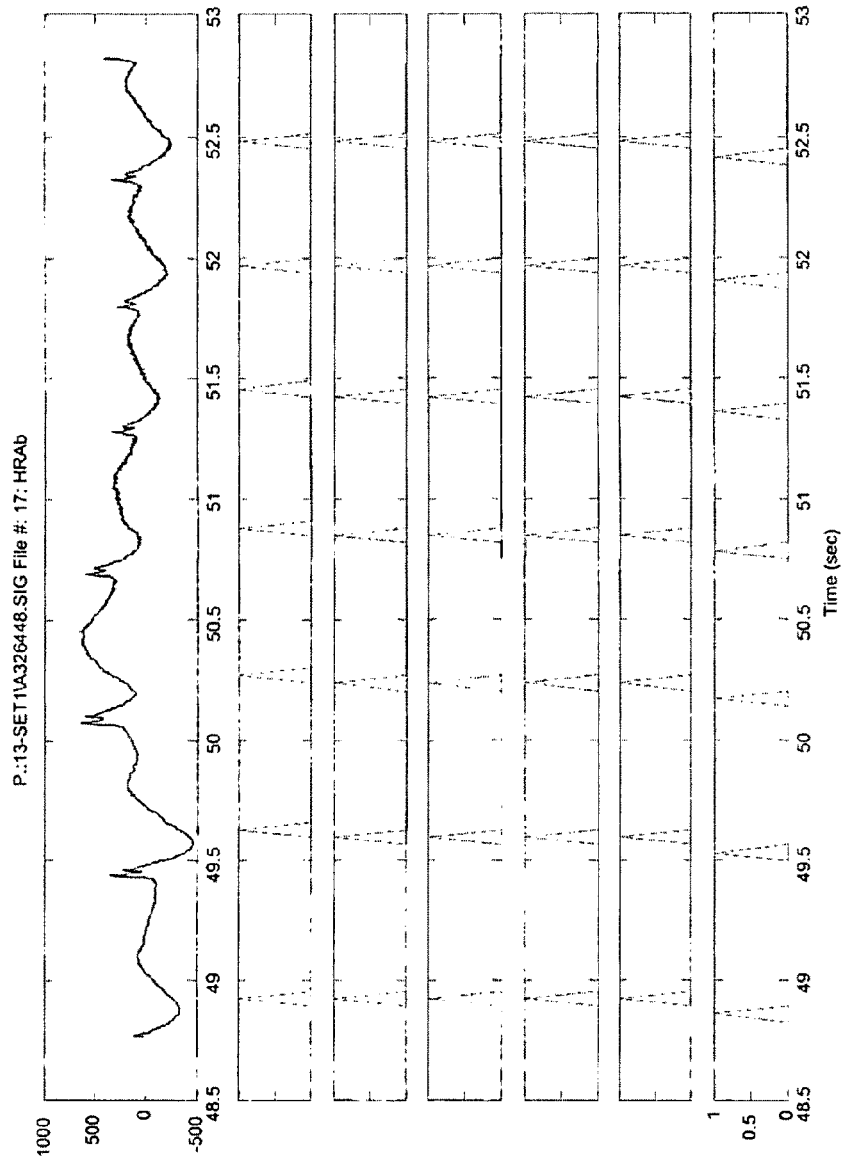
FIG. 17 illustrates Peak detection for EGM signal (top row) of normal rhythm, EGM peak signals (6 bottom rows): 1: 1-Agg, 2:2&3-Agg, 3: 4&5-Agg, 4: 5&6 Agg, 5: Det-Agg, 6: Det-Con.
Figure 18:
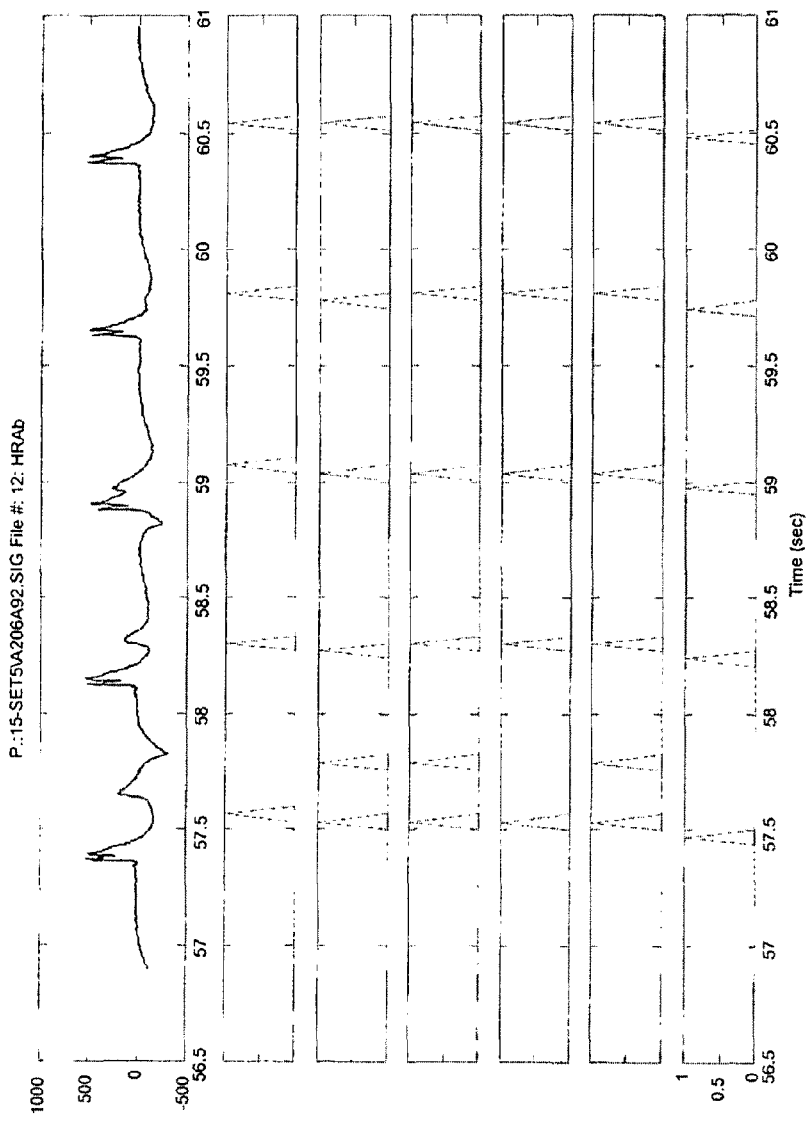
FIG. 18 illustrates Peak detection for EGM signal (top row) of normal rhythm, EGM peak signals (6 bottom rows): 1: 1-Agg, 2:2&3-Agg, 3: 4&5-Agg, 4: 5&6 Agg, 5: Det-Agg, 6: Det-Con.
Figure 19:
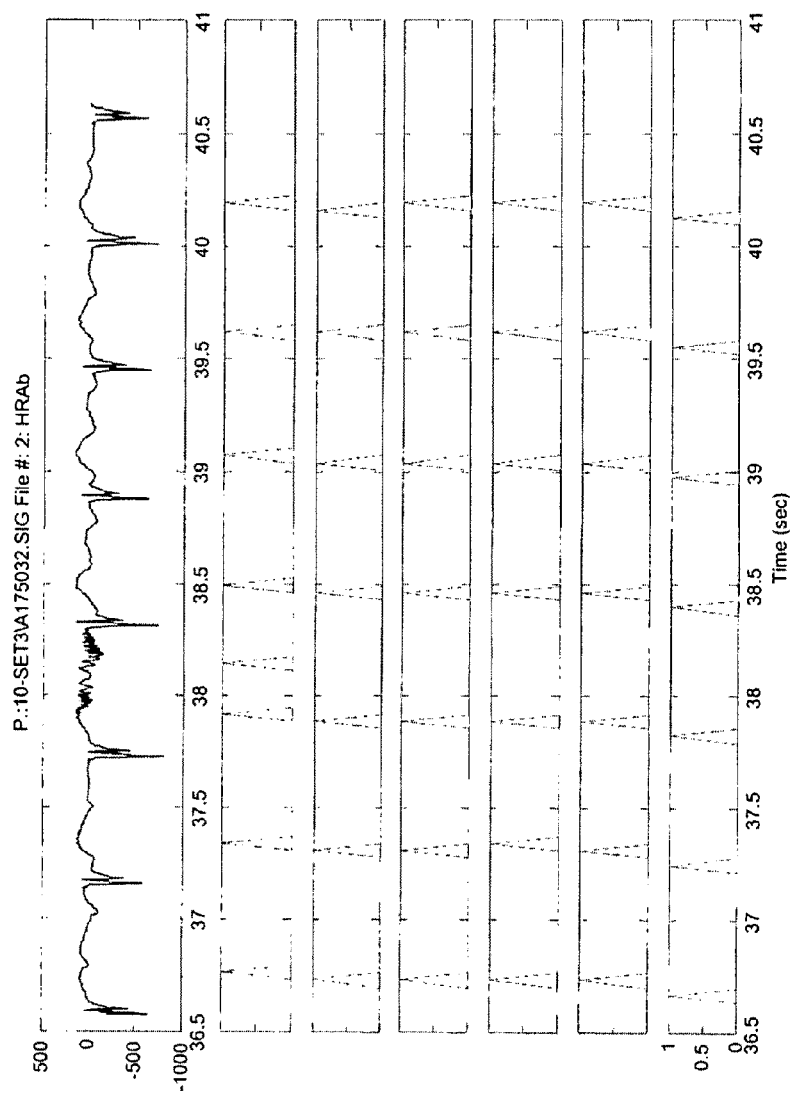
FIG. 19 illustrates Peak detection for EGM signal (top row) of normal rhythm, EGM peak signals (6 bottom rows): 1: 1-Agg, 2:2&3-Agg, 3: 4&5-Agg, 4: 5&6 Agg, 5: Det-Agg, 6: Det-Con.
Figure 20:
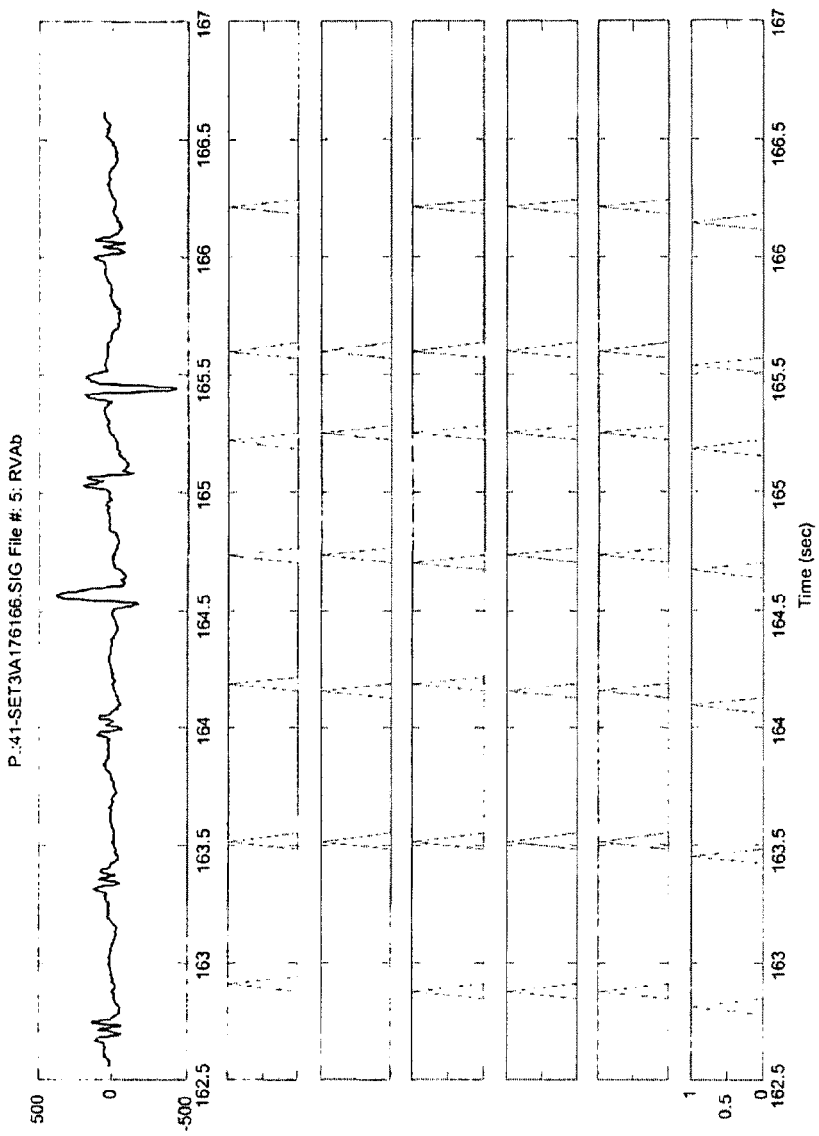
FIG. 20 illustrates Peak detection for EGM signal (top row) of normal rhythm, EGM peak signals (6 bottom rows): 1: 1-Agg, 2:2&3-Agg, 3: 4&5-Agg, 4: 5&6 Agg, 5: Det-Agg, 6: Det-Con.
Figure 21:
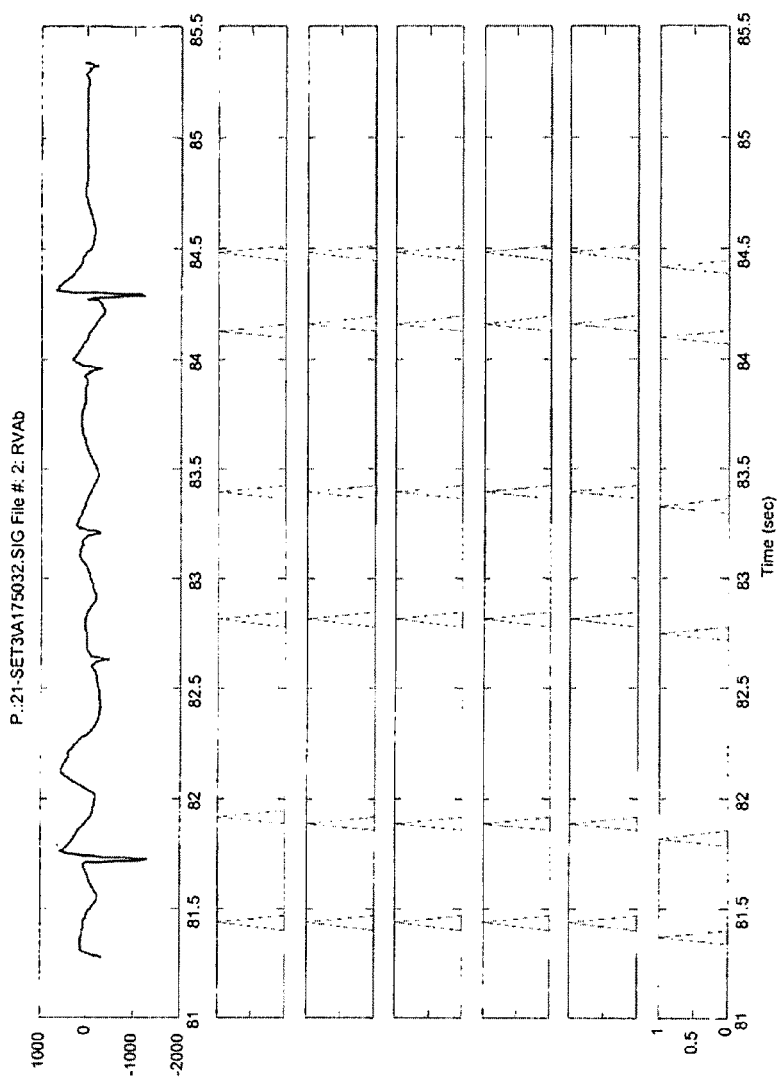
FIG. 21 illustrates Peak detection for EGM signal (top row) of normal rhythm, EGM peak signals (6 bottom rows): 1: 1-Agg, 2:2&3-Agg, 3: 4&5-Agg, 4: 5&6 Agg, 5: Det-Agg, 6: Det-Con.

Another difficulty in beat detection is the EGM morphology variations, artifacts, noise and interference. The WOLA-based method offers robust detection due to its use of multiple bands for detection. FIG. 17 shows a typical normal rhythm after low-energy shocks are delivered to the heart. As shown, the EGM signal baseline varies slowly and randomly. As the figure shows, the WOLA-based method correctly detects the beats (last row of pulses). The correct detection of the beats allows analysis of the effect of shocks. Also FIGS. 18-21 show EGM signal (SR) with morphology variations, artifacts, and noises. As evident, the WOLA-based method detects beats correctly.

The WOLA-based detection may be combined with time-domain processing as shown in FIGS. 1, 2 and 4 to improve the performance and the reliability of the overall CRM system.

The PSM system 10 is also usable for detection, prediction, and control of neurological disorders such as epilepsy and epileptic seizure. In a further embodiment, the WOLA-based PSM 10 is applied to implement control (analysis, detection, prediction, and therapy) of neurological disorders, such as epilepsy and epileptic seizure. Once WOLA analysis is applied to the EEG signal, such as noninvasive scalp EEG, and invasive Intracranial EEG (IEEG) also known as electrocorticogram (ECoG), various linear and nonlinear signal processing methods can be applied to the complex WOLA subband signal.

The PSM system 10 is applicable to any systems that observe, analyze and possibly control part of the human (or animal) body mechanism, which may, but not limited to CRM, epilepsy and epileptic seizure or implantable devices. The physiological signal processing and management implemented by the PSM system 10 may be applied to any control and monitoring system for autonomic systems, control and monitoring of physiological activities in an animal's body, etc.

When low-power and low-size constrains are imposed on devices which are supposed to posses signal processing capabilities intended for physiological signals and systems, the physiological signal processing and management in the PSM system 10 is helpful. The physiological signal processing on an ultra-low resource platform can extend the range of applications for medical technology due to its high performance, low-power consumption and small size. The physiological signal processing and management system described above is particularly useful in environments where low power consumption is desirable or where an embedded processor in a portable system does not have sufficient capabilities to process the signal. For example, it may be used in on-line heartbeat detection on electronic stethoscopes where a low-resource subband processor receives the heartbeat and lung signals directly from microphones, analyses the signals in subband to separate various signals, robustly detects their features (such as heartbeat rate), cancels undesired interferences and synthesizes the signals in an efficient manner without increasing the size or weight of the stethoscope.

Further embodiments of the physiological signal processing are described in detail with reference to FIGS. 22-44. The physiological signal processing associated with FIGS. 22-44 are applicable to the PSM system 10 of FIG. 1.

Figure 22:
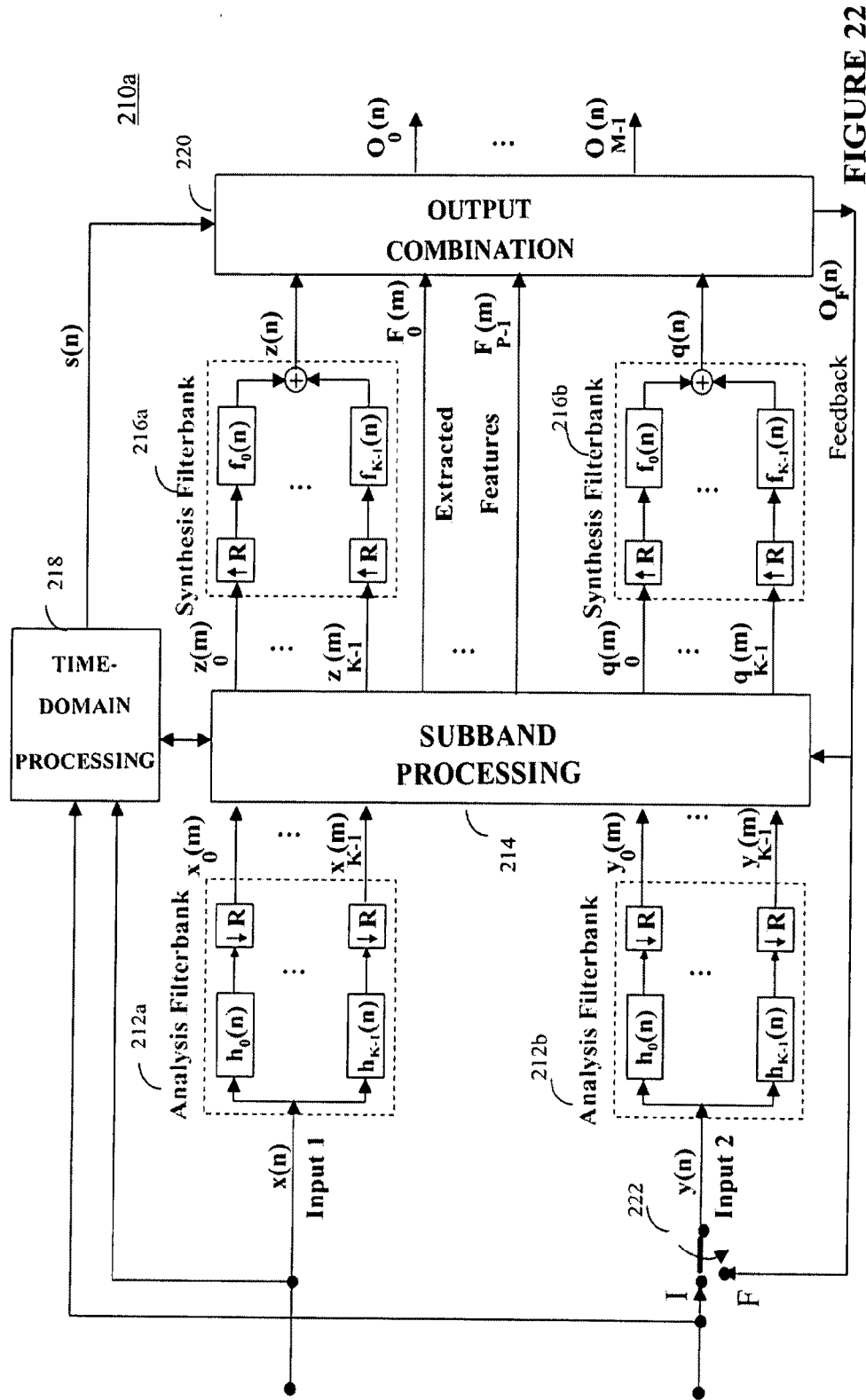
FIG. 22 illustrates a physiological signal processing system in accordance with an embodiment of the present invention.

FIG. 22 shows a physiological signal processing system 210a in accordance with an embodiment (a) of the present invention. One or more input (possibly physiological) signals are converted from the time-domain into the frequency-domain by an oversampled analysis filterbank (212a, 212b), generating subband information signal sets ($x_i(m)$, $y_i(m)$, i=0, 1, ..., K−1) that undergo subband processing at subband processing block 214. In FIG. 22, two input signals x(n), y(n) are shown as examples. However, more than two inputs may be provided to the system 210a. The processed signals ($z_i(m)$, $q_i(m)$, i=0, 1, ..., K−1) are then converted from the frequency-domain to the time-domain by an oversampled synthesis filterbank (216a, 216b). As a result, one or two time-domain output signals z(n), q(n) are obtained. In FIG. 22, two output signals z(n), q(n) are shown. However, more than two time-domain output signals may be obtained.

Each output signal (z(n), q(n)) represents the results of the subband processing 214 on one or more input signals. Thus joint or individual processing of the inputs are both possible. Examples are adaptive (joint) processing of two or more inputs, or single-input noise reduction of each input individually. Features ($F_l(m)$, l=0, 1, ..., P−1) may be extracted in the frequency domain from any of the input signals. An example of a feature is the heartbeat rate for heartbeat input signals. Parallel to the subband processing 214, time-domain processing 218 of the input signals may take place. The time-domain processing 218 may interact with the subband processing block 214 in different ways. The subband processing 214 may control or be controlled by the time-domain processing 218. For example, signal energy might be measured in time-domain with low-delay to control the subband processing 214. As another example, the subband processing 214 may find an optimal adaptive filter in frequency-domain, and convert the adaptive filter back into the time-domain for application to the signals in the time-domain processing block 218 with low latency. Finally correlation processing may be done in time-domain processing block 218 independent of the subband processing 214. Generally, any form of time-domain processing is possible.

The output (s(n)) of the time-domain processing 218 may be combined with other time-domain outputs (z(n), q(n)) in an output combiner 220 to obtain one or more final outputs ($O_i(n)$, i=0, 1, ..., M). The output combiner 220, for example, can obtain linear combinations of the outputs (z(n), q(n), s(n), $F_l(m)$, l=0, 1, ..., P−1) or perform more sophisticated signal processing on the outputs. The output combiner 220 can also provide one or more feedback signals (such as $O_F(n)$ of FIG. 22) for controlling the subband processing block 214 or as its input, or to be used as input signals. For example, at input y(n) in FIG. 22, a switch 222 is on "F" position for the feedback signal to play the role of an input signal, and on "I" position to route input signal y(n) to the system 210a.

Figure 23:
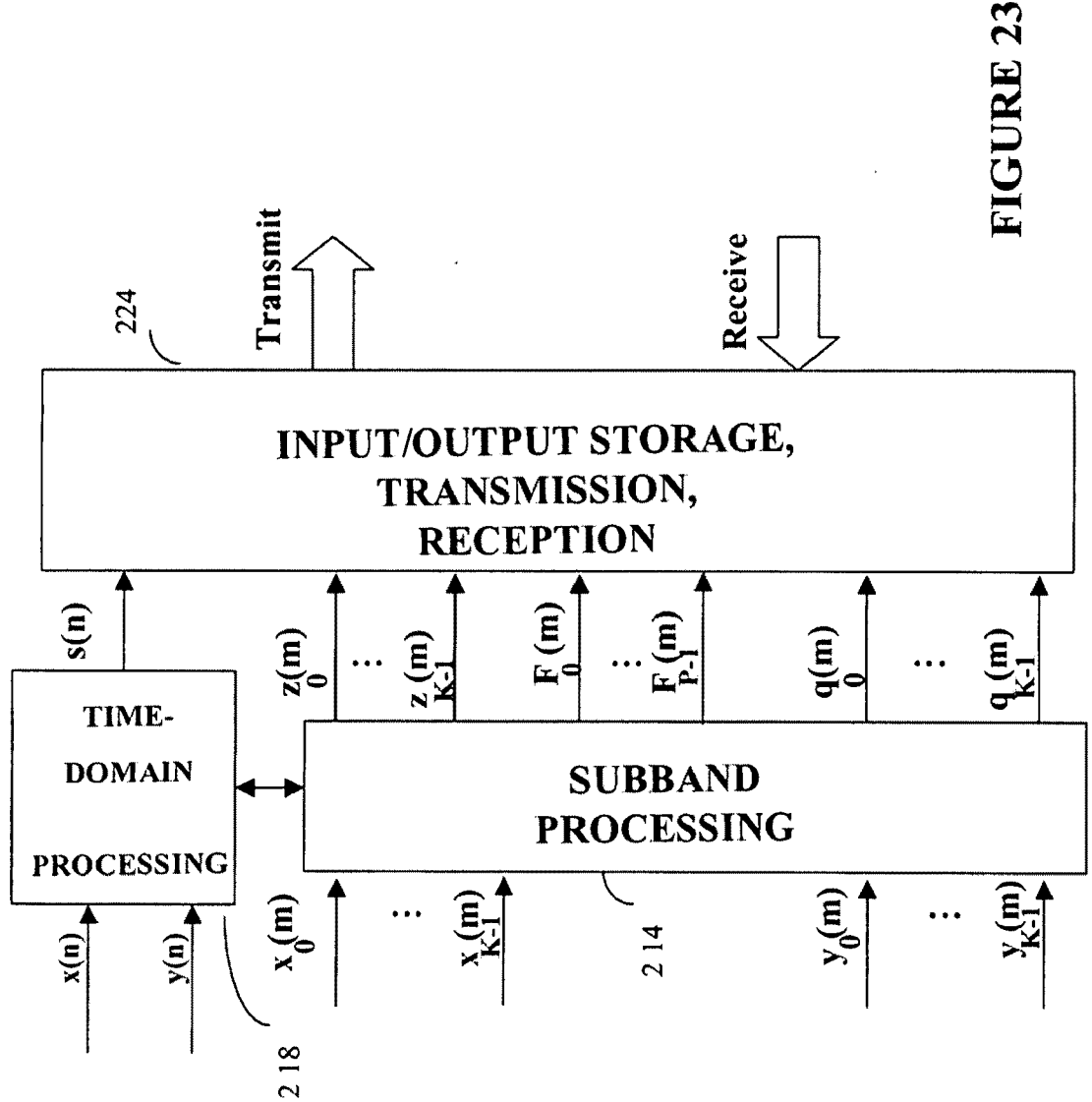
FIG. 23 illustrates an example of a input/output storage, transmission and reception block applied to the system of FIG. 22.

In the processing stage (214, 218) of FIG. 22, all or some of the input/output signals (x(n), y(n), $x_i(m)$, $y_i(m)$, $z_i(m)$, $q_i(m)$, i=0, 1, ..., K−1, $F_l(m)$, l=0, 1, ..., P−1, s(n)) may be stored for future use, or transmitted to other systems, possibly after proper compression or encoding. The processing block (214, 218) can also retrieve the previously stored signals mentioned above or may receive them from other systems. If the signals are already compressed or encoded in any way, the system will decompress or decode them prior to usage. For clarity, this feature is not shown in FIG. 22 and is rather shown separately in FIG. 23. FIG. 23 shows an input/output storage, transmission, and reception block 224. The block 224 is capable of storing all or some of the input/output signals of the subband processing, the time-domain processing or a combination thereof, transmitting them to other systems, and receiving them from other systems. The feature of FIG. 23 is applicable to the physiological signal processing systems 210b-210i of FIGS. 24-31.

It is noted that the analysis filterbank 16a (16b) of FIG. 1 may be similar to the analysis filterbank 212a (212b). It is noted that the synthesis filterbank 22 of FIG. 1 may be similar to the synthesis filterbank 216a or 216b. It is noted that the subband processing block 20 of FIG. 1 may be similar to the subband processing block 214 and may utilize whole or part of the processing scheme of the subband processing block 214. It is noted that the time-domain processing block 18 of FIG. 1 may be similar to the time-domain processing block 218.

Figure 24:
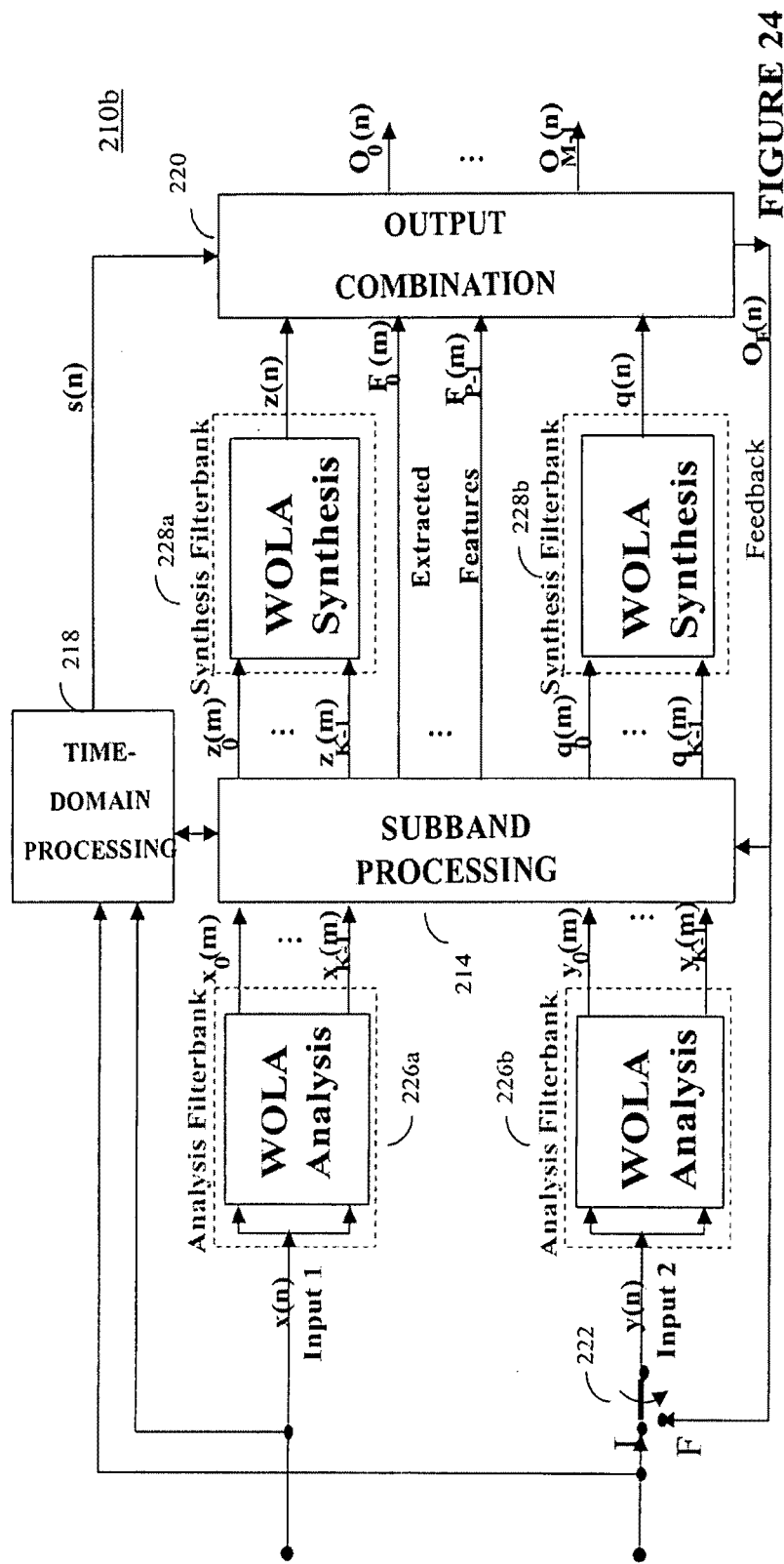
FIG. 24 illustrates a physiological signal processing system in accordance with a further embodiment of the present invention.
Figure 25:
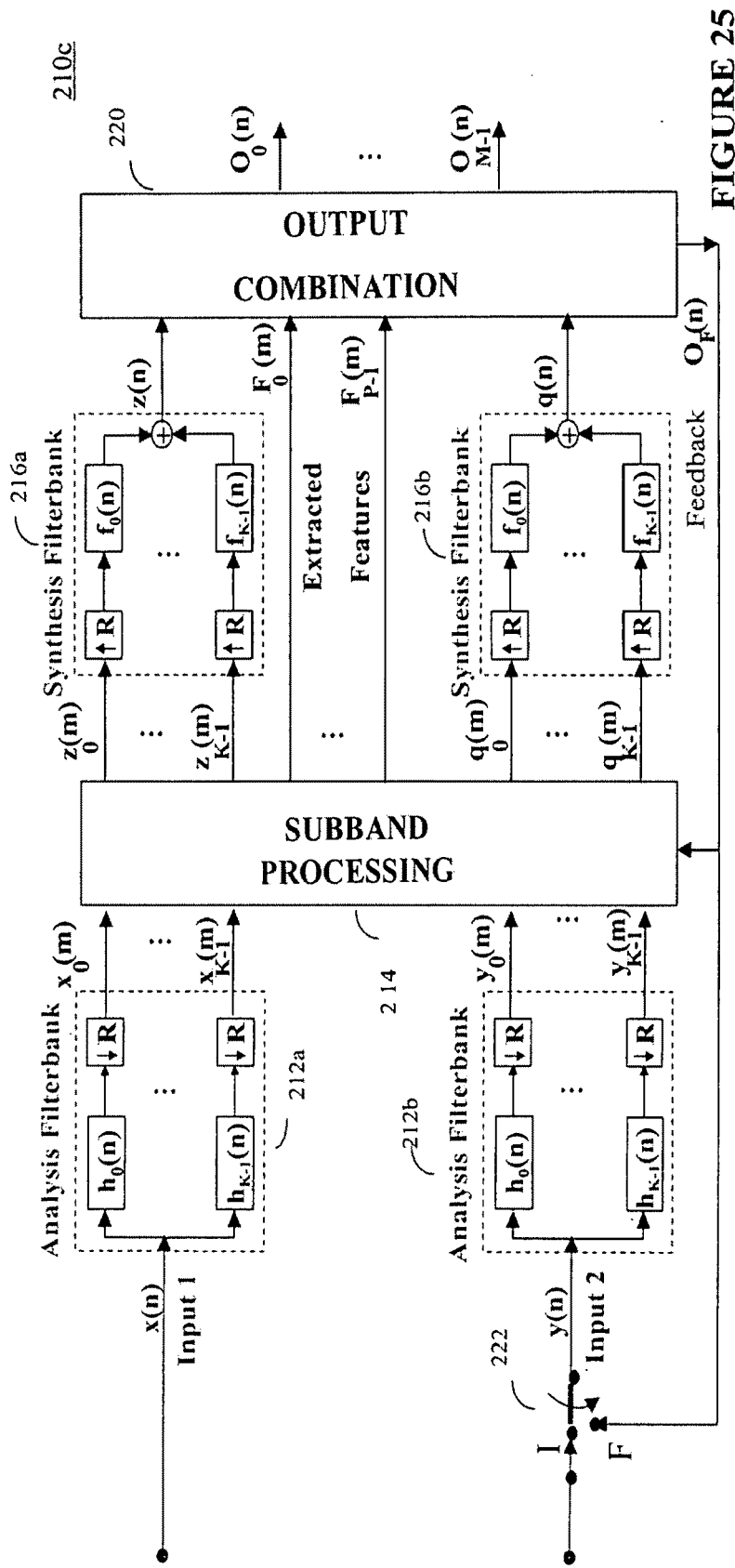
FIG. 25 illustrates a physiological signal processing system in accordance with a further embodiment of the present invention.
Figure 26:
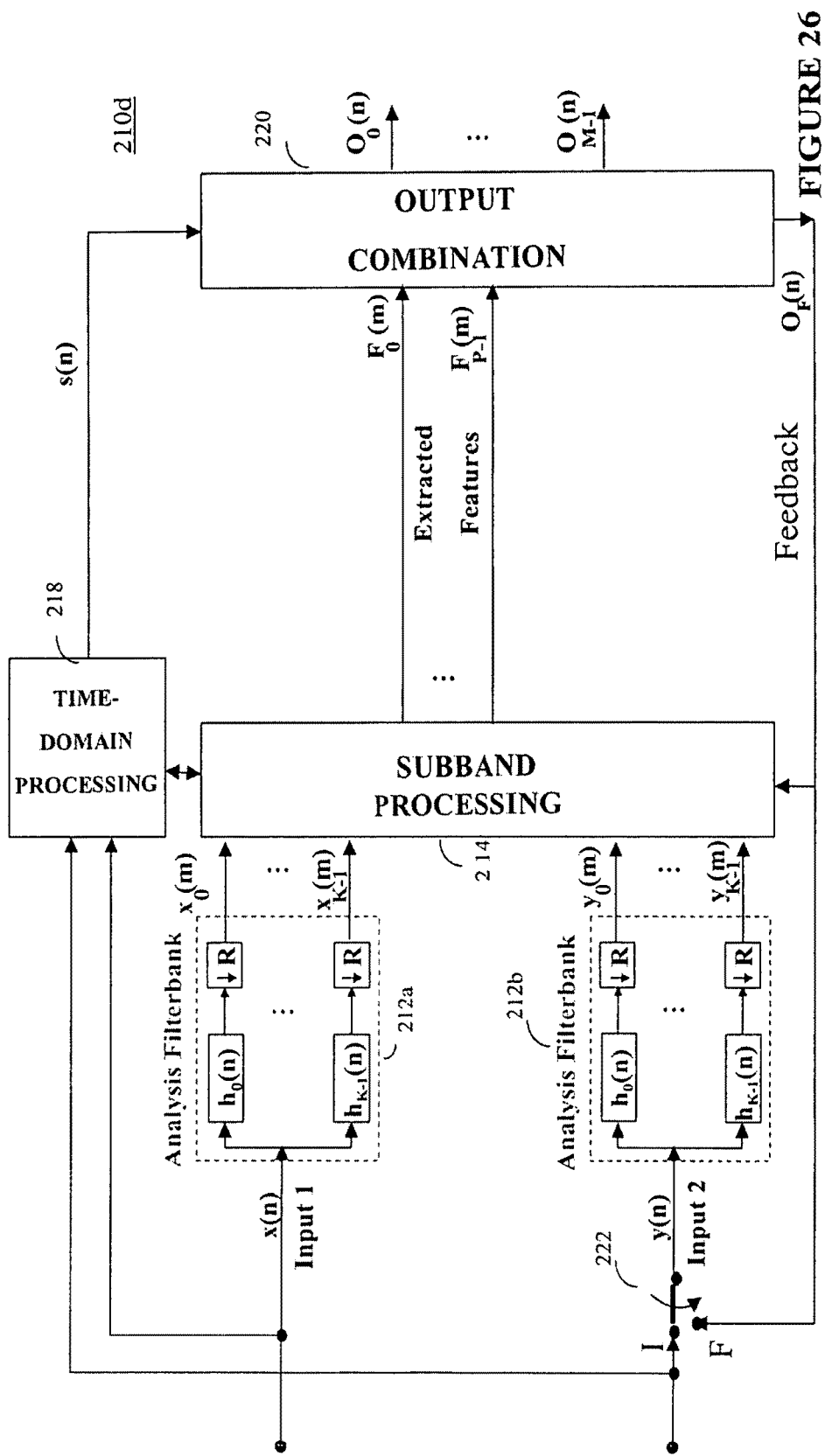
FIG. 26 illustrates a physiological signal processing system in accordance with a further embodiment of the present invention.
Figure 27:
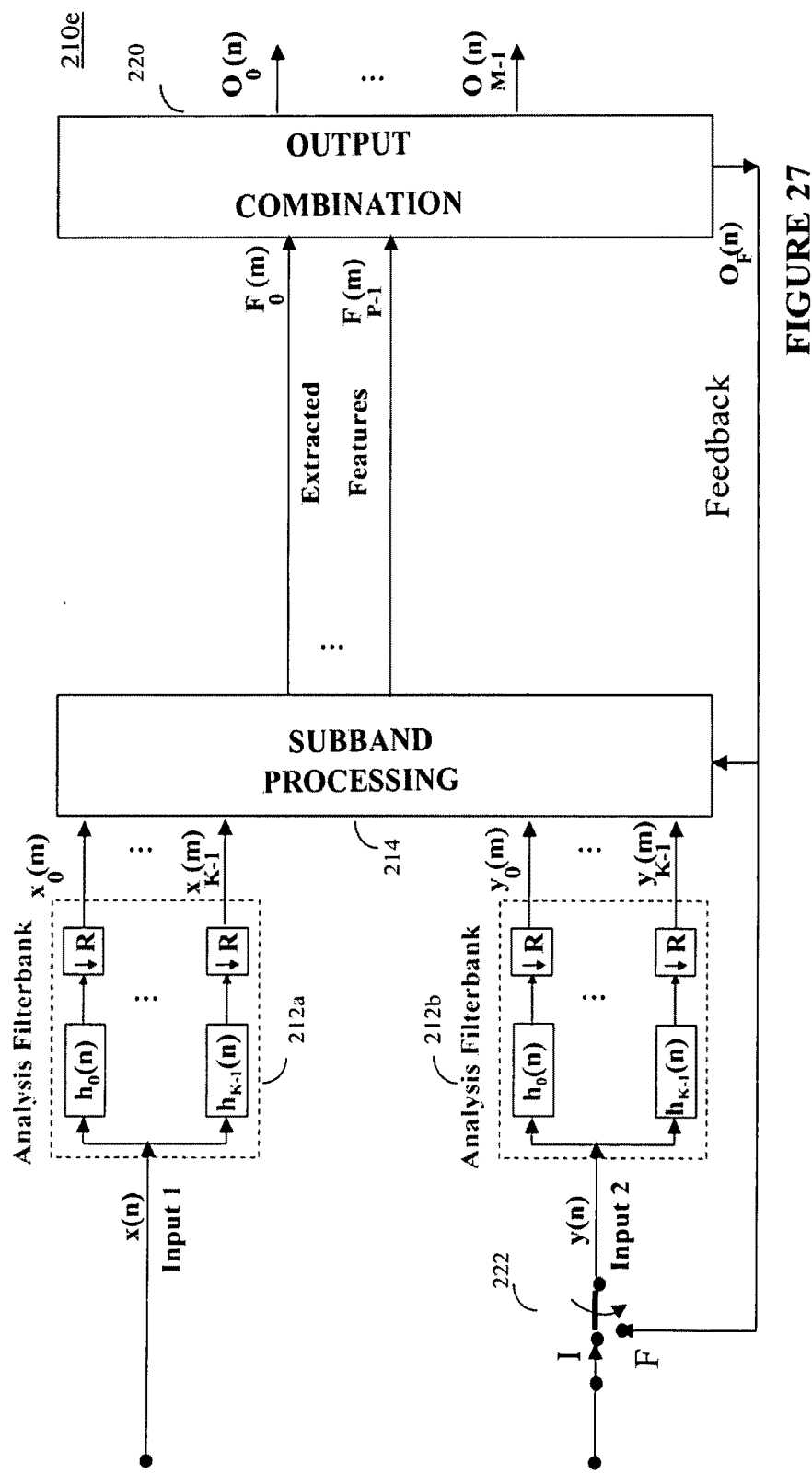
FIG. 27 illustrates a physiological signal processing system in accordance with a further embodiment of the present invention.

FIG. 24 shows a physiological signal processing system 210b in accordance with a second embodiment (b) of the present invention. The system 210b is similar to the system 210*a* of FIG. 22 except for the oversampled filterbanks. In system 10*b*, the oversampled analysis filterbanks 212*a*, 212*b* and the oversampled synthesis filterbanks 216*a*, 216*b* are replaced by WOLA analysis filterbanks 226*a*, 226*b* and WOLA synthesis filterbanks 228*a*, 228*b*, respectively.

WOLA analysis filterbank 226*a* (226*b*) may be similar to WOLA analysis filterbank 16*a* (16*b*). WOLA synthesis filterbanks 228*a* (228*b*) may be similar to WOLA synthesis filterbank 22. Thus, the WOLA based physiological signal processing systems described herein can be efficiently implemented on a low-resource hardware platform, such as 100 of FIG. 3, 100A of FIG. 4.

Figure 28:
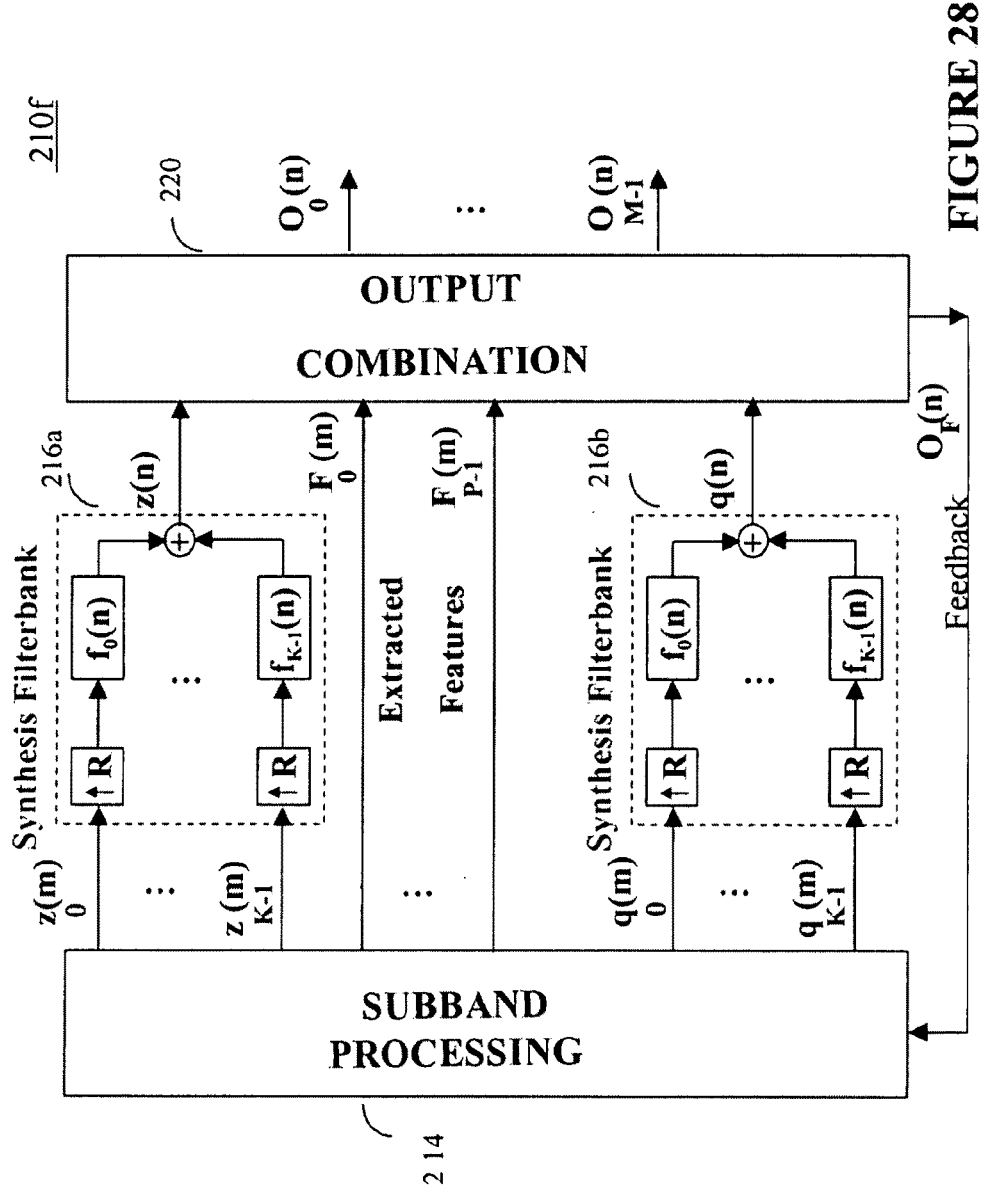
FIG. 28 illustrates a physiological signal processing system in accordance with a further embodiment of the present invention.

The systems 210*a* and 210*b* may be further optimised or simplified for specific applications as long as one or more oversampled filterbanks or WOLA analysis and/or synthesis are present in the system. FIGS. 25-28 show systems 210*c*-210*f* in accordance with further embodiments (c)-(f) of the present invention. For example, in the system 210*c* of FIG. 25, the time-domain processing block does not exist as it is not needed for certain applications. Similarly, synthesis filterbanks and their outputs may not be needed in some architectures, such as system 210*d* of FIG. 26, and system 210*e* of FIG. 27. An example could be heartbeat rate detection through joint time-domain and subband processing, without a need to play the heartbeat sound at the output. In the system 210*e* of FIG. 27, only features are extracted through the subband processing 214. An example could be heartbeat rate detection through subband processing. Finally, as shown in FIG. 28, the system 210*f* does not include the analysis filterbanks. The subband processing block 214 may receive, at its input, a feedback signal from the output combiner 220, a signal from the input/output storage, transmission, reception block 224 of FIG. 23, or a combination thereof. In some applications, the input signals may have been analysed and stored prior to subband processing 214. Thus, the analysis stage is not needed on-line.

The oversampled analysis and synthesis filterbanks of the systems 210*c*-210*f* of FIGS. 25-28 may be replaced by WOLA analysis and WOLA synthesis filterbanks, respectively.

Figure 29:
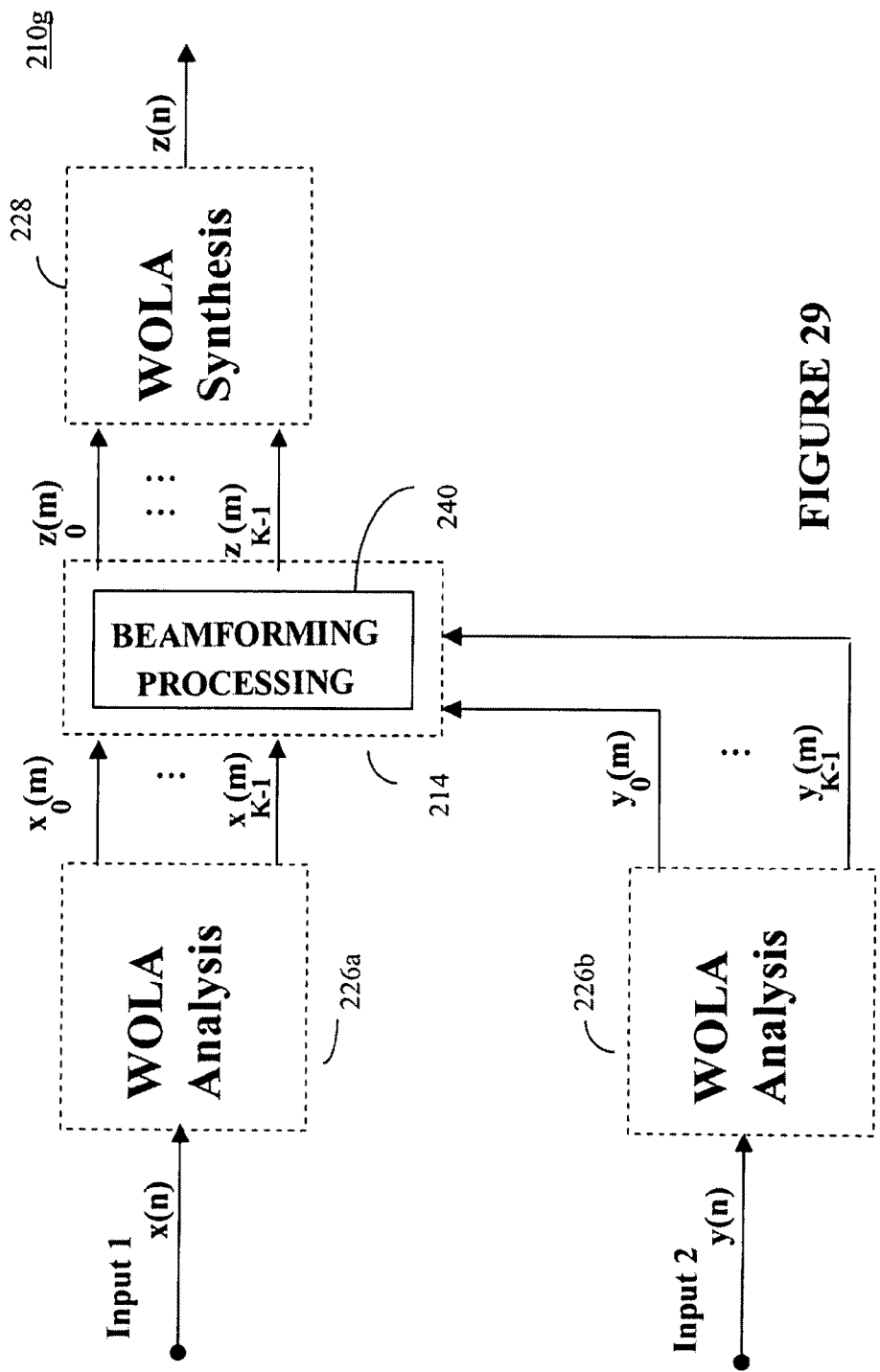
FIG. 29 illustrates a physiological signal processing system with beamforming algorithm in accordance with a further embodiment of the present invention.

A beamforming algorithm may be used as part of a physiological signal processing system, such as the systems 210*a*-210*f* of FIGS. 22 and 24-28. For example, when multiple sensors are employed to process various signals coming from distinctly located sources (such as mother's heartbeat and fetal heartbeat) beamforming will enable the user to aim at a particular sound source with less interference from other sources. This algorithm takes two or more input signals in the time-domain signal and converts them to the frequency-domain using either an oversampled analysis filterbank, or a WOLA analysis filterbank. The beamforming algorithm processes the data before the signal is converted back to the time-domain by an oversampled synthesis filterbank or a WOLA synthesis filterbank. FIG. 29 shows a physiological signal processing system 210*g* in accordance with a further embodiment (g) of the present invention. The system 210*g* contains a beamforming block 240 which performs a beamforming algorithm. The beamforming block 240 receives the outputs of the WOLA analysis filterbanks 226*a*, 226*b* and provides its output to the WOLA synthesis filterbanks 228. In FIG. 29, two inputs are provided to the system 210*g*. However, one or more than two inputs may be provided to the system 210*g*. Various beamforming algorithms have been disclosed in U.S. patent application Ser. No. 10/214,350, Publication No. 20030063759, which is incorporated herein by reference.

The WOLA analysis and synthesis filterbanks in FIG. 29 may be replaced by oversampled analysis and synthesis filterbanks, respectively. The subband processing 214 of the physiological processing systems 210*a*-210*g* may include the beamforming processing block 240.

Figure 30:
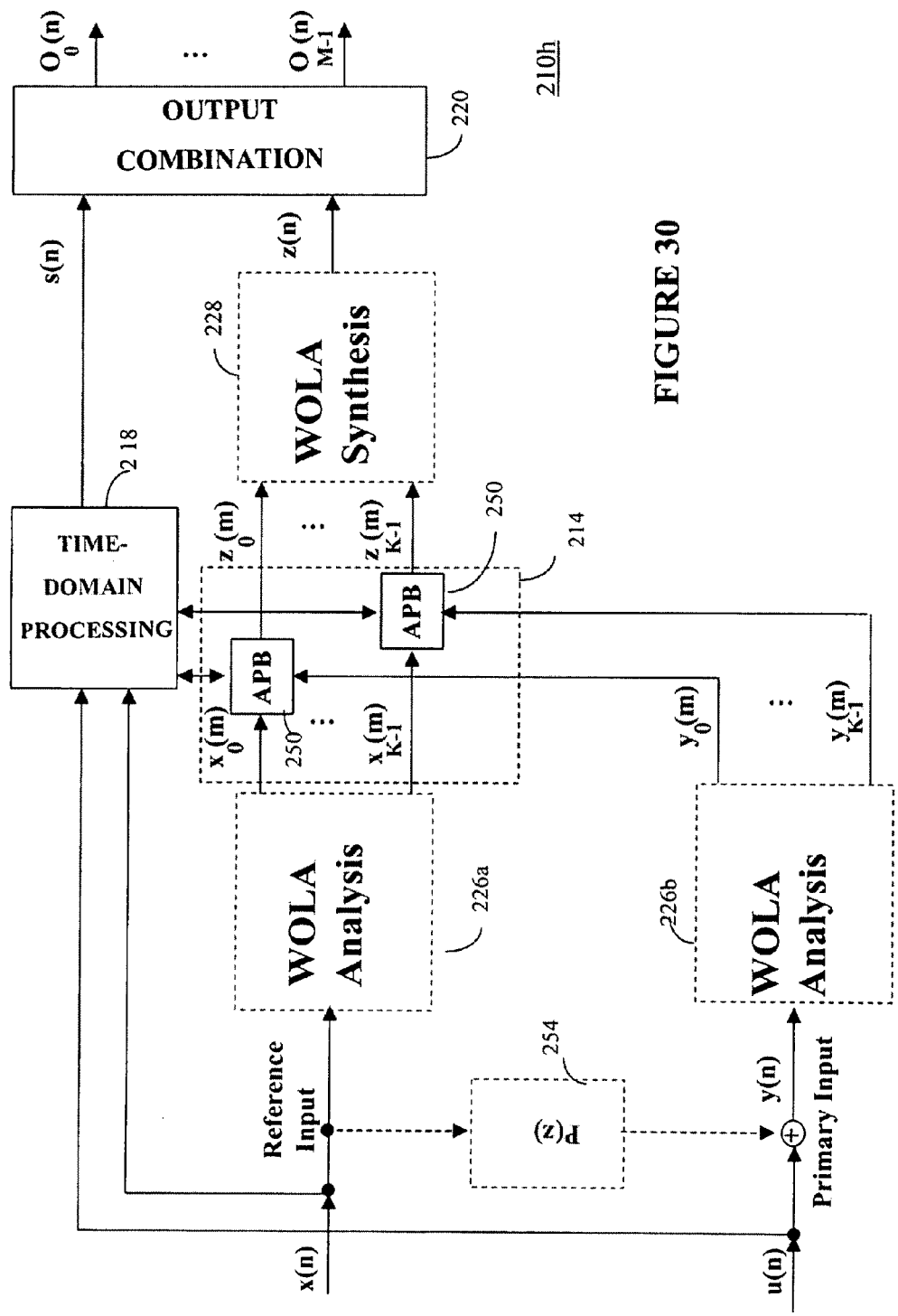
FIG. 30 illustrates a physiological signal processing system with a subband adaptive filter in accordance with a further embodiment of the present invention.

Subband adaptive filtering may be implemented in a physiological signal processing system. FIG. 30 shows a physiological processing system 210*h* with a subband adaptive filter (SAF) in accordance with a further embodiment (h) of the present invention. In many applications, a signal (reference signal x(n) in FIG. 30) may leak into anther signal u(n) after passing through a system 254 (P(z)). The second input to the WOLA analysis 226*b* is the primary signal y(n) that includes u(n) plus a component correlated to x(n). SAFs can efficiently cancel the interference (X(z)·P(z) in the Z-domain) by exploiting the correlation of the primary signal with the reference signal. An example is isolating lung sounds in signals containing both heart and lung sounds. This will enable the listener to hear the lung sound without the interference of other sounds. A second example would involve isolating a fetal heartbeat from a signal containing both the maternal and fetal heartbeats. This will enable the fainter fetal heartbeat to be processed separately and heard more clearly.

These examples, as well as others can be implemented in the same way using the structure shown in FIG. 30. At least two input (possibly physiological) signals (x(n) and y(n)) are converted from the time-domain to the frequency-domain using the WOLA analysis filterbank (212*a*, 212*b*). The system 210*h* contains Adaptive Processing Blocks (APBs) 250. Each subband is processed by the corresponding APB 250 before being synthesized by the WOLA synthesis 228. The results s(n) of the time-domain processing 218 may then be combined with the subband processing result z(n) to generate one or more output signals that are free from interference. As described above in the embodiment (a), the time-domain processing 218 may interact with the subband processing in different ways. In particular, the SAFs may be converted back to the time-domain to reconstruct a time-domain adaptive filter to be used in the time-domain processing 218. This will reduce the processing delay through the system.

The WOLA analysis and synthesis filterbanks in FIG. 30 may be replaced by oversampled analysis and synthesis filterbanks, respectively. The physiological processing systems 210*a*-210*g* of FIGS. 22 and 24-29 may include the APBs 250. For example, APBs disclosed by U.S. patent application Ser. No. 10/642,847, Publication No. 20040071284 may be used as APB 250. The APBs (for example) employ whitening by spectral emphasis, whitening by decimation and a combination of the two, step-size adaptation techniques, as well a hybrid of subband adaptive filtering and Wiener filtering to achieve improved performances.

Figure 31:
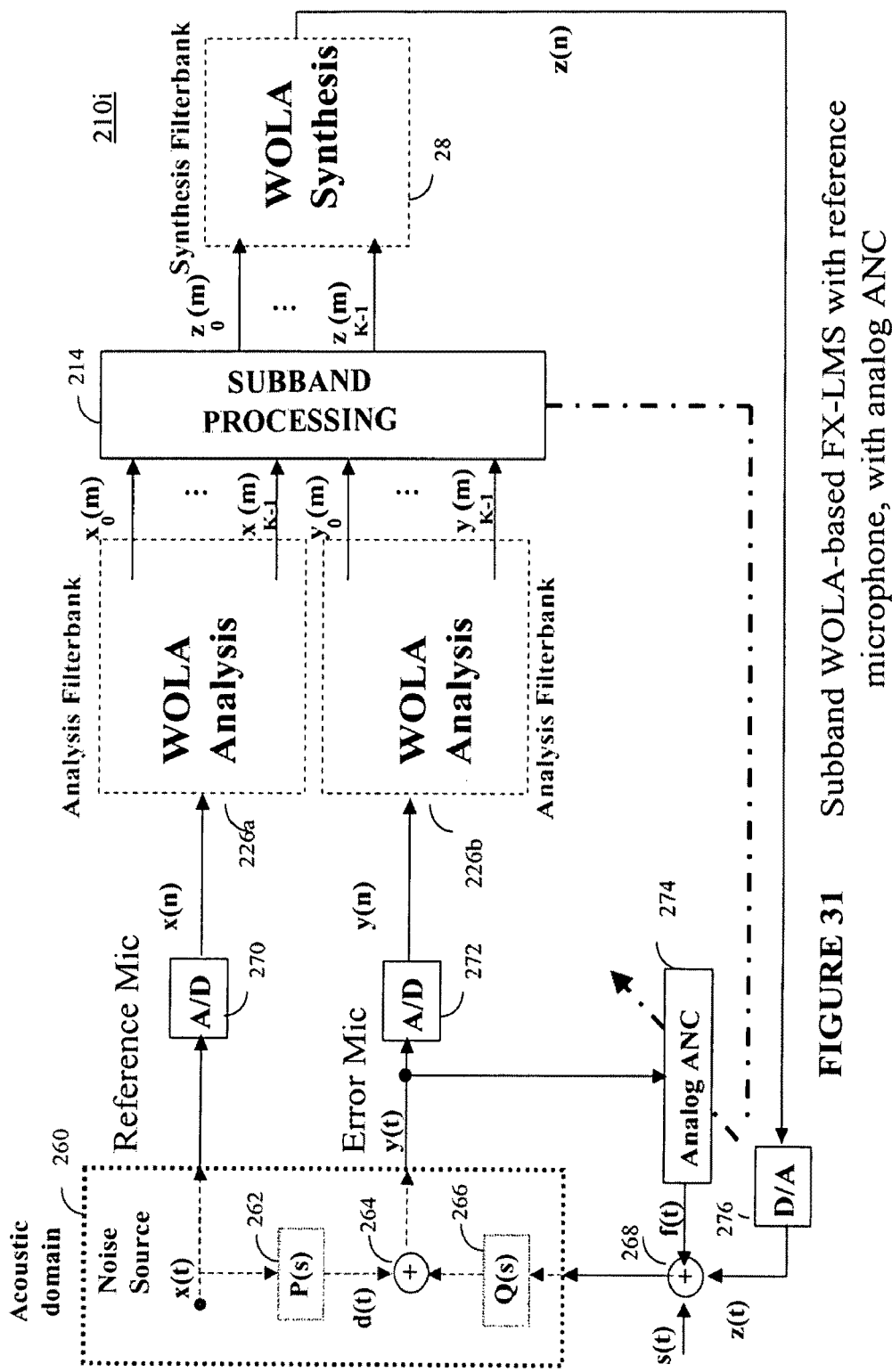
FIG. 31 illustrates a physiological signal processing system with an active noise cancellation in accordance with a further embodiment of the present invention.

Active noise cancellation using oversampled filterbank may be employed for input (possibly physiological) signals. FIG. 31 shows a physiological signal processing system 210*i* in accordance with a further embodiment (i) of the present invention. In FIG. 31, a noise source x(t) passes through the acoustic medium (modelled by acoustic transfer function P(s), s denoting the Laplace transform variable), added to a desired signal s(t) (that has to pass through an acoustic transfer function Q(s)) and converted to an electric signal y(t) by the microphone 264 (denoted by an adder in FIG. 31). After analog to digital conversion (A/D) 270, 272, the two signals x(n) and y(n) are processed by a subband adaptive system to estimate a noise signal estimate z(n).

The system 210*i* includes subband processing 214 that might include adaptive processing employing one of many adaptive algorithms, such as filtered-X LMS (FXLMS), Affine Projection Algorithm (APA), or Recursive Least Squares (RLS). The noise signal is then converted back to an acoustic signal, played through a noise speaker 268 to reach the microphone 264 and added acoustically to the microphone signal to cancel the additive noise. The noise speaker to microphone acoustic transfer function Q(s) 266 can be estimated offline or online to be employed in the system 210i. The system 210i may have processing delay between the inputs (x(t) and y(t)) and the output z(t). Canadian Patent application No. 2,481,629, filed on Sep. 15, 2004, entitled "Method and system for active noise cancellation", discloses methods of reducing the delay with more efficient designs. One possible solution is to combine the subband-based Active Noise Cancellation (ANC) with an analog ANC 274 with its parameters such as loop-filter and loop-gain adjusted through subband processing as shown in FIG. 31. An example of an application of this system is a stethoscope with more than one sensor, capable of reducing interference from lungs and other noise sources into the heartbeat sound through active noise cancellation. The system 210i might operate without the reference microphone 270 as described in the Canadian Patent application No. 2,481,629, filed on Sep. 15, 2004, entitled "Method and system for active noise cancellation". When a reference signal is not available, it is possible to reconstruct it in the FX-LMS or similar adaptive systems based on estimation of microphone acoustic transfer function Q(s).

It is noted that each of the systems 210a-210e and 210g-210i of FIGS. 22, 24, 27, and 29-31 receives two inputs. However, more than two inputs may be provided to each system.

As an embodiment of the present invention patent, a stethoscope for listening to physiological sounds is described in detail. A stethoscope in accordance with an embodiment of the present invention includes oversampled filterbank which is implementable into the platform of FIG. 3 or FIG. 4.

Figure 32:
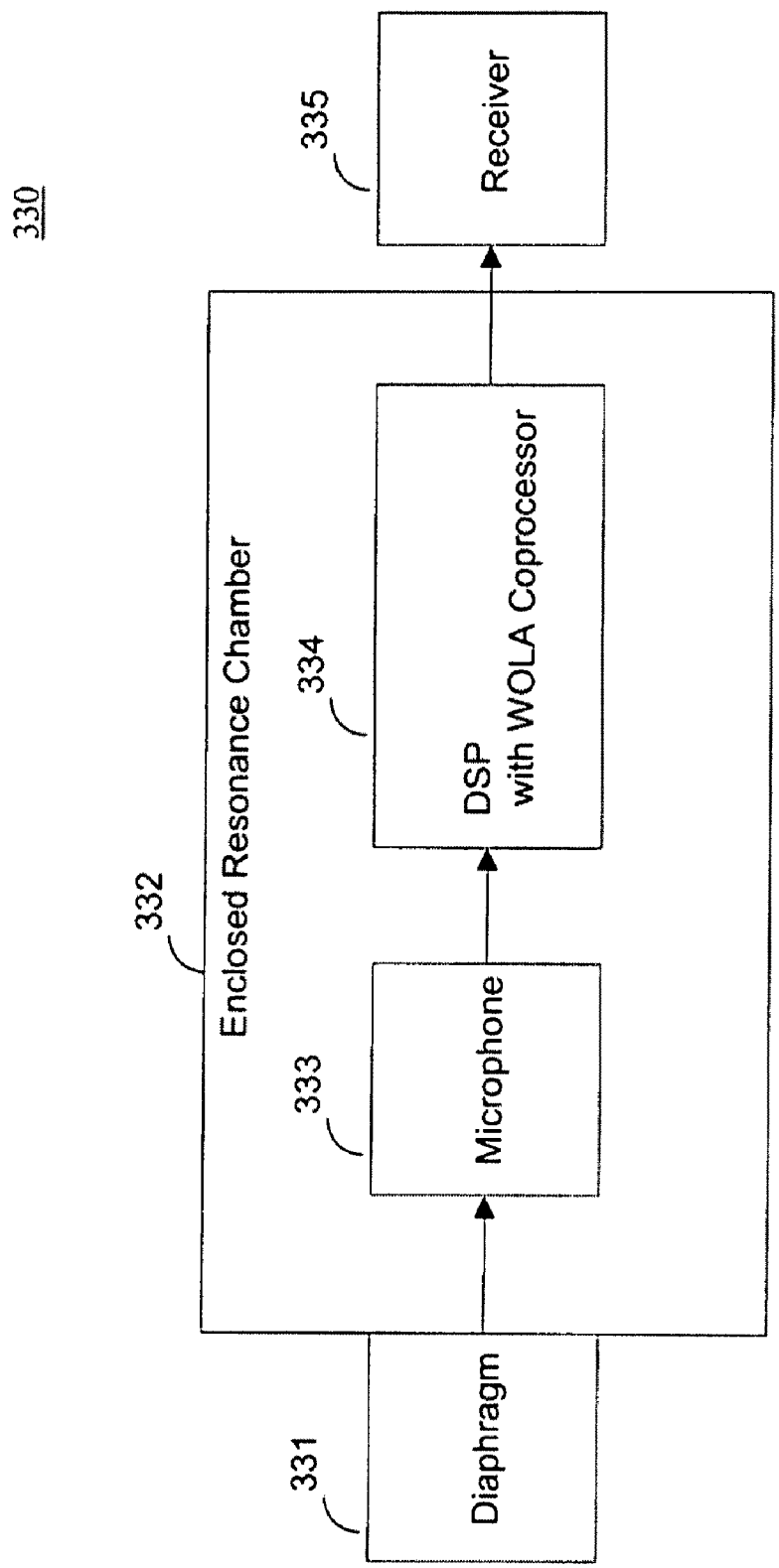
FIG. 32 illustrates a stethoscope in accordance with an embodiment of the present invention.

FIG. 32 shows a stethoscope 330 in accordance with an embodiment of the present invention. The stethoscope 330 is an electronic instrument to listen to physiological sounds including heartbeats, lung sounds and bowel/gastrointestinal sounds, among others. The stethoscope 330 includes a diaphragm 331, an enclosed resonance chamber 332, and a microphone 333. The diaphragm 331 is a disk used for amplifying the sound. The microphone 333 transforms the sound in the chamber 332 from an acoustic to an electrical signal. The stethoscope 330 further includes at least one programmable digital signal processor 334 on which the WOLA coprocessor (e.g. 104 of FIG. 3) resides. The DSP system 334 corresponds to the DSP system 100 of FIG. 3. The stethoscope 330 further includes one or more receivers 335 or speakers which make the sound audible for the stethoscope wearer, and/or one or more algorithms to process one or more live input signals and/or one or more recorded signals.

The stethoscope 330 has the functionality of one or more filtering modes to emphasize different portions of the signal, and volume control. The stethoscope 330 has record functionality whereby one or more live input signals are stored in non-volatile memory such as an EEPROM. The signal may or may not be compressed prior to storage. The stethoscope 330 has playback functionality whereby one or more signals stored in non-volatile memory such as an EEPROM are played back either at the recording speed or some other speed, such as half speed. The stethoscope 330 has the functionality of a human-machine interface for controlling the functionality. For example, the interface unit has a plurality of buttons including: one to control volume up, one to control volume down, one to change the filtering mode used by the gain adjustment algorithm, one to record, one to initiate playback and one to initiate half speed playback. The interface unit has an LCD display that indicates the current filtering mode, volume changes, whether recording/playback is occurring and whether the battery is low. The interface unit commutates with the DSP system 334.

It is assumed that the DSP system (334) includes an 18-bit block floating point weighted overlap-add (WOLA) filterbank coprocessor, a 16-bit fixed-point DSP core, and an input-output processor (IOP). The parallel operation of these components enables the implementation of complex signal processing algorithms with low system clock rates and low resource usage and is particularly adept at subband signal processing. The configurable WOLA coprocessor (104 of FIG. 3) efficiently splits the full-band input signals into subbands, leaving the core free to perform other algorithm calculations.

The WOLA coprocessor (104 of FIG. 3) implements a flexible oversampled Generalized DFT (GDFT) filterbank. It may be adapted to generate critically-sampled, real-valued filterbanks as required for a codec in this application It is assumed that the algorithms are implemented on the DSP system 134 using a 16-band, 4-times oversampled WOLA filterbank configuration with odd-stacking. The selected configuration generates a group delay of 17 milliseconds, has a system clock frequency of 5.12 MHz and a sampling frequency of 8 kHz. This is one configuration, and others are also possible.

Figure 33:
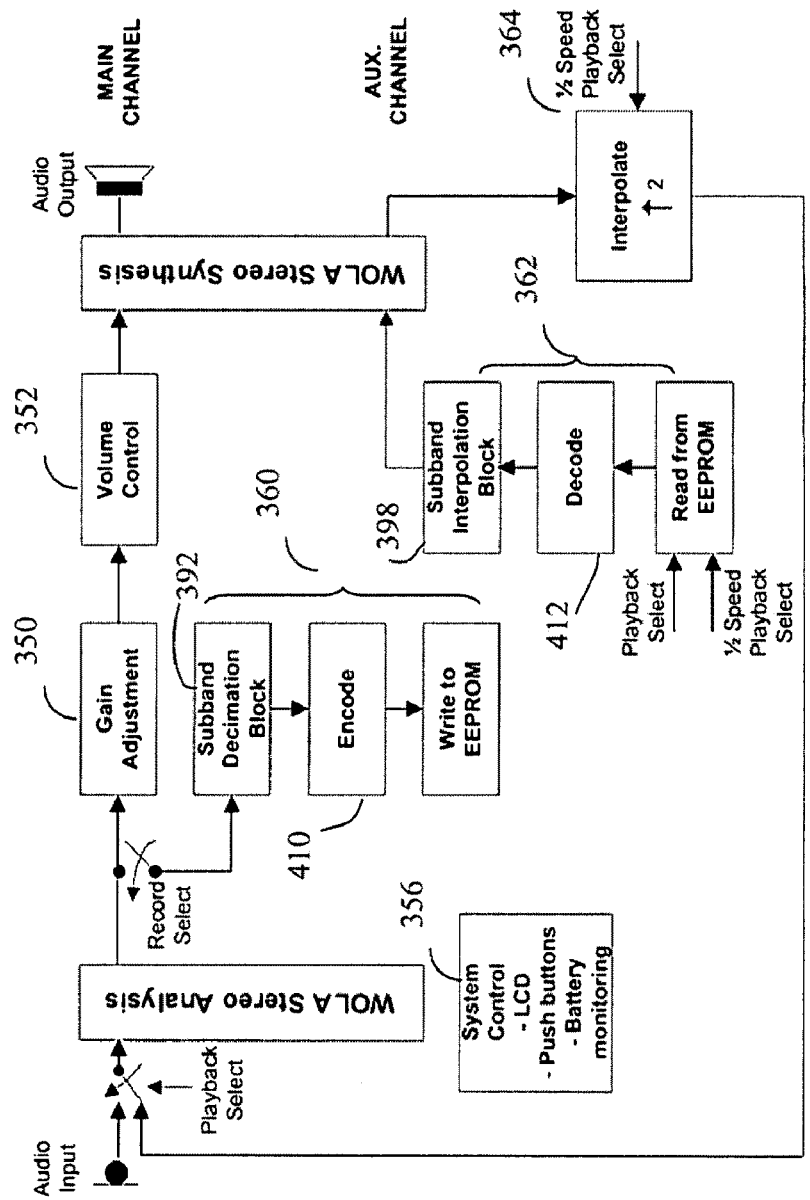
FIG. 33 illustrates an example of the stethoscope of FIG. 32.

FIG. 33 illustrates examples of the stethoscope 330 of FIG. 32. Referring to FIG. 33, the stethoscope includes a plurality of modules including module 350 for subband gain adjustment, module 360 for record functionality, modules 362 and 364 for playback functionality and playback at half speed functionality, and system-level features including volume control module 352 and control module 356 for battery monitoring, push buttons control and a LCD display. Blocks 350, 352, 360, and 362 are examples of possible subband processing 214 in FIG. 22. Block 364 is an example of possible output combination in FIG. 22.

The subband gain adjustment algorithm 350 provides frequency shaping as required by the various listening modes. Generally, the components of heartbeat and lung sounds useful for diagnostic purposes are in the range of 20-1000 Hz. The first through fourth heart sounds fall in the range of 20-115 Hz. Disorders such as pulmonary and aortic diastolic heart murmurs occur in the range of 140-600 Hz. Thus, a suitable listening range for heart sounds is approximately 20-600 Hz. For breathing sounds, the strongest part of the signal is typically under 100 Hz, although the signal can have useful components up to 1.2 kHz.

As described below, the subband codec (e.g. 394 of FIG. 35) is used as part of the record and playback functionality. During recording, the signal is captured, encoded, packed and written to non-volatile memory (e.g. EEPROM 396 of FIG. 35). During playback, the packed signal is read from the EEPROM, unpacked, decoded and re-synthesized in real-time (362). Interpolation module 364 is provided for half speed playback mode.

The filterbank requirements of the subband gain adjustment algorithm and the subband coding algorithm are different. Subband gain adjustment requires low delay and yet optimal filter responses to reduce the level of uncancelled aliasing that is generated when gains are varied in different subbands. The WOLA filterbank uses over-sampling to achieve high levels of aliasing reduction without increasing the filter length and consequently the group delay as described in U.S. Pat. No. 6,236,731. To keep the group delay as low as possible, as an example, a sampling frequency of 8 kHz is selected. A sampling frequency of 4 kHz is more appropriate given the bandwidth of heart and lung sounds, but has higher group delay. The gain adjustments required by the different listening modes are large Thus, an over-sampling factor of at least 4 may be selected to minimize group delay and minimize aliasing artifacts.

In contrast, the subband coding algorithm requires a critically-sampled, real-valued filterbank to achieve minimal data rates. Low group delay is not a requirement. As described in D. Hermann et al. ("Low-Power Implementation of the Bluetooth Subband Audio Codec", Proc. ICASSP 2004), critically-sampled, real-valued subband signals can be obtained by postprocessing and decimating the oversampled complex WOLA subband signals.

In order to design the WOLA filterbank having relatively low group delay and an over-sampling factor of 4, an analysis window length (La) of 128 samples, a synthesis window length (Ls) of 128 samples, an input block size of R=8 samples and an FFT size of N=32 may be selected. This is an exemplary configuration. Other configurations are also possible.

For subband gain adjustment algorithm, the system 330 may implement three different filter modes which have been designed based upon the characteristics of heart and lung sounds: a bell mode, which amplifies low frequency heart sounds in the range 0-500 Hz, a diaphragm mode, which amplifies lung sounds in the range 0-1000 Hz and an extended range mode which amplifies sounds between 0-1500 Hz.

The use of an oversampled subband filterbank permits the application of efficient gain adjustments. The gain application is a vector process in which each subband is multiplied by a real-valued gain. In this system, the gain application process occurs on dedicated, efficient hardware, namely, the WOLA coprocessor (104 of FIG. 3).

The number of subbands used in the stethoscope design is, for example, 16. This number directly determines the resolution of the frequency shaping. Since the sampling frequency is 8 kHz, the bandwidth of each band is 250 Hz. The system utilizes odd-stacking which means that the first band encompasses the frequencies from 0 to 250 Hz. A real-valued gain is provided for each band. To implement the bell mode, for example, gains greater than zero are provided for the first two subbands while gains of zero are provided for the remaining subbands.

One possible codec (e.g. 394 of FIG. 35) uses adaptive PCM quantization in each subband. This quantization scheme was used because it provides good performance for slowly varying signals such as heart sounds, while having a low complexity implementation. Other quantization schemes may be used. This subband codec requires critically-sampled, real-valued subband signals as input. Since the filterbank required by the gain adjustment algorithm has an over-sampling factor of 4, for example, the analysis results are downsampled by a factor of 2 and then converted to cosine modulated filterbank results in order to be usable by the codec. The analysis filterbank applicable to the subband codec has the form described by Equation (1), where hm(n) is the subband analysis filter, m is the subband index, M=16 is the number of subbands and hp(n) is the prototype low-pass filter. The filter length, L was set to La=Ls. Note that this filterbank, referred to as a cosine-modulated filterbank, uses odd-stacking and that the WOLA filterbank is also configured for odd-stacking. Other filterbank configurations are possible.

$$h_m(n) = h_p(n)\cos\left[\frac{\pi}{M}\left(m + \frac{1}{2}\right)\left(n - \frac{M}{2}\right)\right] \quad n = 0 \cdots L - 1 \quad (1)$$

To achieve this filterbank of (1), the following two steps are implemented. First, to reduce the data by a factor of 2, every other input block is skipped. This effectively doubles the block size (R) of the resulting analysis. The resulting subband signals do not contain additional aliased images because the original oversampled subband signal is band-limited to $\pi/4$. Secondly, to obtain critically-sampled, real-valued data, the subband signals are further decimated and modulated to obtain a cosine-modulated filterbank similar to the one described in the D. Hermann reference.

The decimation of the signal before coding may cause the aliasing that is amplified by the gain adjustment 350 to appear as audible distortion during playback. To eliminate this distortion, the reconstructed signals are filtered prior to gain adjustment removing the unwanted aliasing. A filter may be implemented on the DSP core (106 of FIG. 3). However, the data may be synthesized and re-analyzed using another oversampled filterbank prior to gain adjustment. This approach can be achieved by using a second channel that is available on the DSP, as shown in FIG. 33.

In FIG. 33, analysis results in the main channel are decimated, encoded, packed and stored 360 during the record operation. During playback, these signals are unpacked, decoded and interpolated 362 into an auxiliary channel. The reconstructed signals are synthesized in this auxiliary channel and then copied from the output of this channel to the input of the main channel. The auxiliary channel is used only for reconstruction of the encoded signal.

This two-channel approach is selected because the two separate analysis and synthesis chains are more efficiently implemented on two channels than two completely separate filterbanks are on a single channel. In order to implement two separate filterbanks on one channel, the extra synthesis and analysis steps may be implemented manually on the DSP core (106 of FIG. 3). In contrast, the chosen method takes advantage of available capabilities on the WOLA coprocessor (104 of FIG. 3) while minimally increasing resource usage.

Half speed playback functionality is described in detail. This mode requires data to be decoded at one rate and played back at another, in an architecture that has a fixed sampling rate. Halving the speed of a signal doubles the amount of the data to be processed. It is preferable to solve the problem in real-time by changing the effective sampling rate of the recorded data while playing it back at the normal fixed sampling rate.

The playback speed is halved by interpolating the decoded signal by a factor of 2 in the time domain while keeping the system's sampling rate constant. Although this interpolation method does not preserve the pitch of the signal (it is halved), the details in the sounds are more clearly heard by the medical professional in this mode. Interpolation of the time domain signal will create an image of the entire spectrum. The gain adjustment algorithm, which is performed immediately before synthesis, removes the top half of the spectrum. Thus, the gain adjustment algorithm that is already in place can be used to eliminate this imaging.

Figure 34:
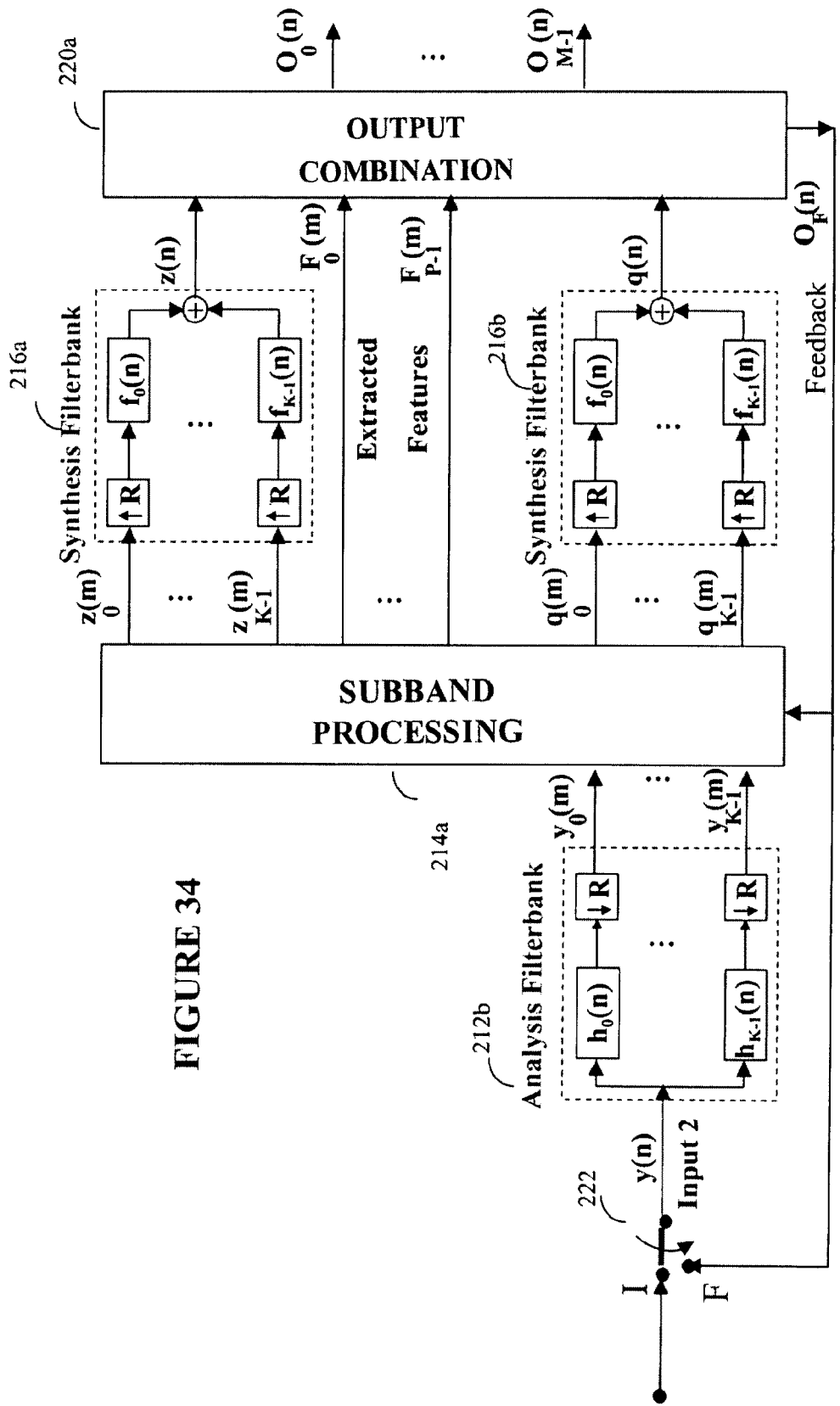
FIG. 34 illustrates a possible implementation of a signal processing scheme on the DSP of FIG. 32.
Figure 35:
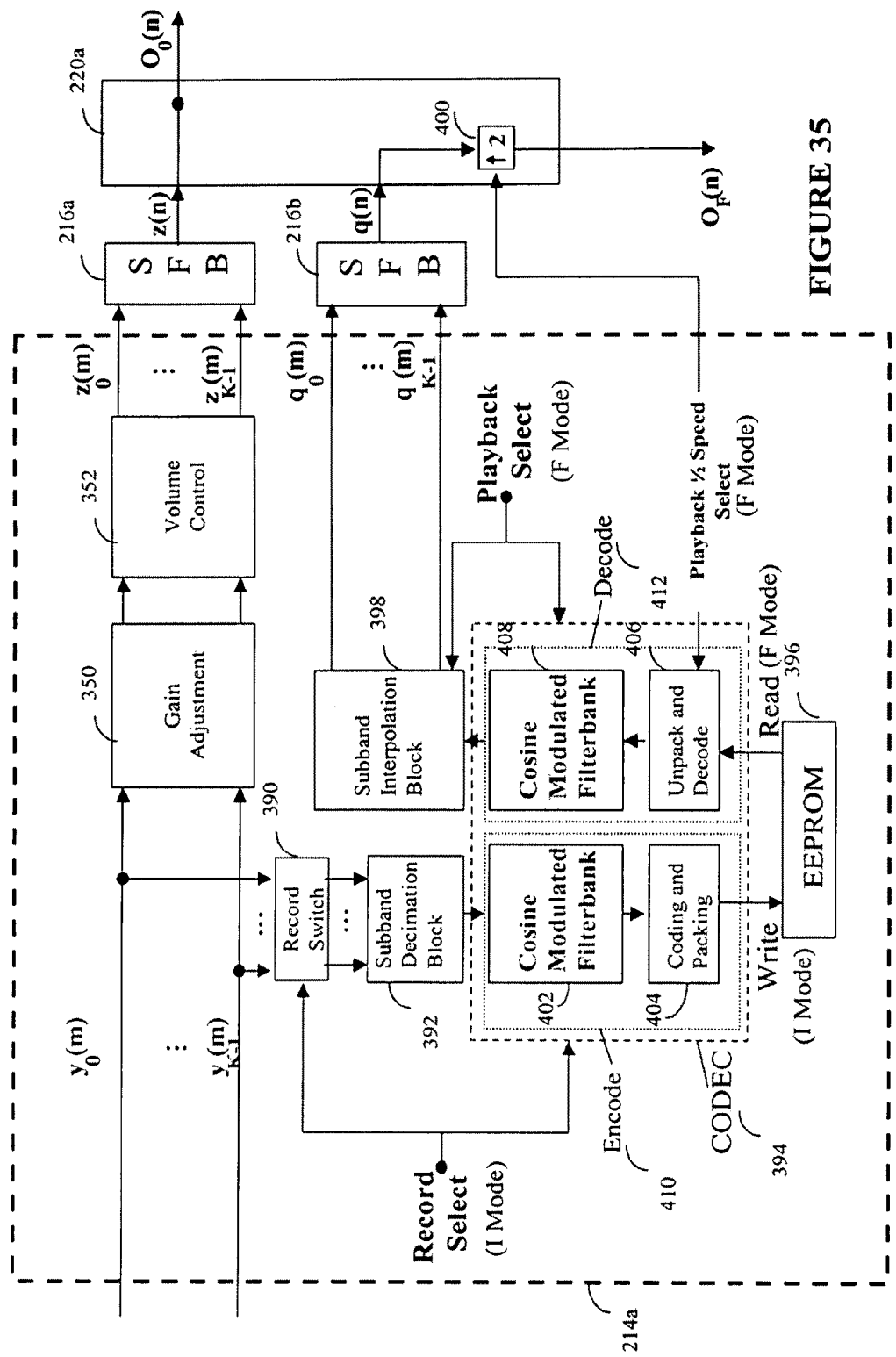
FIG. 35 illustrates an example of a subband processing block and an output combination block of FIG. 34.

FIG. 34 illustrates an exemplary implementation of a signal processing scheme on the DSP with WOLA coprocessor 334 of FIG. 32. FIG. 35 illustrates the subband processing 214*a* and the output combiner 220*a* of FIG. 34. FIG. 34 employs methods of FIG. 33 for stethoscope applications.

Referring to FIGS. 34-35, the analysis filter bank 212b, a subband processing block 214a, the oversampled synthesis filterbanks 216a-216b and an output combiner 220a are implemented on the DSP with WOLA coprocessor. The system of FIG. 34 accepts only one input signal y(n). It is noted that the subband processing block 214a and the output combiner 220a are similar to the subband processing block 214 and the output combiner 220 of FIG. 22, respectively.

The record, playback and playback at half speed module includes a record switch 390, a subband decimation block 392, CODEC 394, an EEPROM 396, and a subband interpolation block 398. The combiner 220a includes the interpolation module 400.

The CODEC 394 includes a cosine modulated filterbank module 402, coding and packing module 404, unpacking and decoding module 406 and a cosine modulated filterbank module 408. The cosine modulated filterbank module 402 applies cosine modulated filterbank as described above. The cosine modulated filterbank module 408 implements the inverse operation (as described in the D. Hermann reference).

The coding and packing module 404 codes data as described above, and then packs the data into frames. The unpacking and decoding module 406 unpacks the data frame and decodes the data. The decoding reconstructs the samples based on the process described above.

When the switch 222 is in the "I" position, the stethoscope (330) is in input mode and can possibly record a signal if the record switch 390 is closed by a record select input. When the switch 222 is on the "F" position, the system is in playback mode. The subband CODEC 394 is used as part of record and playback functionality. Regardless of the I/F switch position, the input signal y(n) is captured and analyzed by the oversampled filterbank 212b. The subband analysis results $y_i(m)$, i=0, 12, . . . , K−1 are fed into the subband processing block 214a, processed by the gain adjustment module 350 and the volume control module 352. The processed signals output from the volume control module 352 are synthesized in real-time at SFB 216a to obtain the time-domain signal z(n) that is routed to the output signal $O_O(n)$. At the same time, if the record select input is active, the subband analysis results $y_i(m)$, i=0, 12, . . . , K−1 are decimated by the subband decimation module 292, converted to cosine modulated filterbank results, encoded and packed by the CODEC 394, and stored in the EEPROM 396.

During playback, compressed signals are read from the EEPROM 396, decoded and converted to oversampled, complex modulated filterbank results by the CODEC 394, and interpolated by 2 in the subband interpolation module 398 to obtain the subband signal set of $q_i(m)$, i=0, 12, . . . , K−1. This set is synthesized in real-time through the synthesis filterbank 16b to obtain the time-domain signal q(n). The signal q(n) is routed to the feedback signal $O_F(n)$ through the module 400. With the I/F switch 222 in the "F" mode, the feedback signal is analyzed by the analysis filterbank 212b prior to gain adjustment and volume control at 350 and 352. This feedback scheme is designed to eliminate distortions due to subband decimation/interpolation combined with the gain adjustment 350. After synthesis by block 216a, the signal z(n) is routed to the output signal $O_O(n)$ through the block 400. As a result, every block of data read from the EEPROM 396 is synthesized with one block (i.e. one subband sample) of delay. While a block of data is read from the EEPROM 396, the previous block of data has already gone through the feedback loop, and is in the process of being sent to the output.

FIG. 36-38 illustrates the prototype of the stethoscope 330 of FIG. 32.

The systems 210a-210f described above are applicable to heart beat detection. The heart beat detection may be implemented using autocorrelation on the WOLA. This method uses a subband autocorrelation technique to detect the heartbeats.

Estimating the autocorrelation by FIR method is described in detail. First, a signal is windowed to obtain a large enough record. For example, it is windowed to have 2-4 periods of the signal included. As the minimum heart rate is around 40 beats per minute (BPM), a window of 4 seconds may be chosen. Then, the autocorrelation estimate is found directly by time-domain (autocorrelation or covariance methods) implementation using one or more complex subband signals resulting from a WOLA analysis. Finally, the peak autocorrelation value in the region of interest is found.

Assuming a window of B samples with no overlap between the windows, and A autocorrelation lags, this needs A·B complex Complex Multiply-and-Adds (CM&A's) per window, or A CM&As per sample. Typical numbers for WOLA subband implementation with a sampling frequency (Fs) of Fs=8 kHz, and R=8 are: B=4000 samples (4 seconds); Minimum and Maximum heartbeats of 40 and 250 BPMs; Autocorrelation lag range: 240-1500, thus A=1500−240=1260; Computation cost: O=A CM&A's per sample, O=1260 CM&As every ms (sample rate in subband is Fs/R=1 kHz) or 4A (5040) real M&As per ms. Additionally, to find the squared magnitude of the autocorrelation estimate, 2*A/B extra (real) M&As: 0.002*A M&As per sample is used. This load is negligible compared to the O=A cost.

Estimating the autocorrelation by IIR method is described in detail. In IIR method, estimating the autocorrelation using sample estimation and averaging it over time is implemented by an IIR filter:

$$R(m,n)=\text{Alpha}\cdot R(m,n-\text{Delta})+(1-\text{Alpha})\cdot X(n)\cdot X^*(n-\text{Delta}) \quad (2)$$

where * represent complex conjugation, m represents the autocorrelation lag, n is the time index, Alpha is a constant close to one, R(m,n) is the estimated autocorrelation vector at time n, X(n) is a complex subband signal after a WOLA analysis (typically the first subband is used for heartbeat detection) and Delta>1 is a constant that controls the recursion update.

Computation cost is: O=2·A/Delta CM&As (8·A/Delta M&As) per subband sample. Delta can be chosen large enough to decrease the computations. Trade offs in choosing Delta will be described below. Typical numbers for the same WOLA parameters as the FIR method are as follows:

Delta=8 (⅛ ms), thus O=A/4=315 CM&As per sample or 1260 M&As per sample. As described above, the IIR method may be more efficient by a factor of Delta/2.

Equation (2) can be modified to:

$$|R(m,n)|=\text{Alpha}\cdot|R(m,n-\text{Delta})|+(1-\text{Alpha})\cdot|X(n)\cdot X^*(n-\text{Delta})| \quad (3)$$

The computation cost may be the same: O=8·A/Delta M&As per sample. However, this method needs to store only real values of the autocorrelation estimates in the range of R(m,n) to R(m,n−Delta). The autocorrelation storage needed for Equation (3) is: A·Delta as compared to 2A·Delta for Equation (2). Moreover, averaging the magnitudes estimates in Equation (3) is more efficient since it ignores the unnecessary phase.

Both IIR and FIR methods need storage for the past values of subband samples X(m,n−Delta). While the FIR methods needs to store B (4000) complex past values, the IIR method needs A (1260) complex values to be stored.

In both methods it is possible to use only the real part of the subband signal to reduce computation and storage in half. Equation (3) may be then modified as:

$$R(m,n)=\text{Alpha}\cdot R(m,n-\text{Delta})+(1-\text{Alpha})\cdot|\text{real}(X(n))\cdot \text{real}(X(n-\text{Delta}))| \quad (4)$$

FIGS. 39-44 illustrate simulation results of the FIR method and the IIR method of Equation (3) for various abnormal heart sounds. In FIGS. 20-25, symbols "o" and "*" specify the IIR and FIR methods, respectively.

Figure 39:
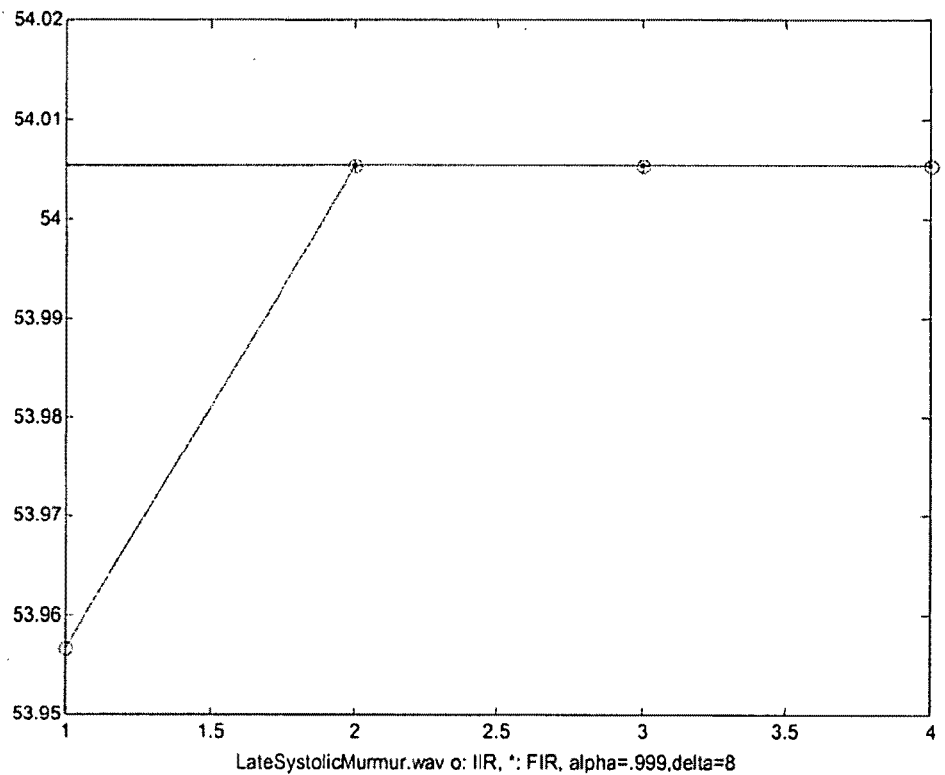
FIG. 39-44 illustrate graphs showing simulation results associated with autocorrelation for detecting physiological signals.

FIG. 39 illustrates detected heartbeat versus time using the FIR method and the IIR method of Equation (3), for Late Systolic Murmur case.

Figure 40:
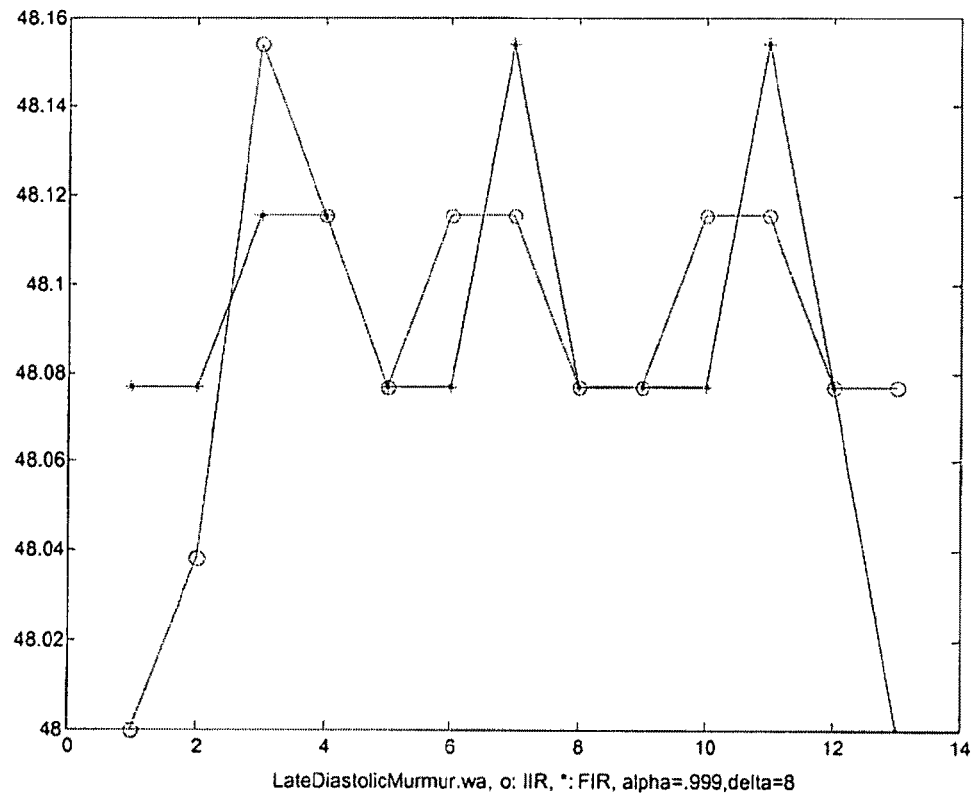

FIG. 40 illustrates detected heartbeat versus time using the FIR method and the IIR method of Equation (3), for Late Diasystolic Murmur case.

Figure 41:
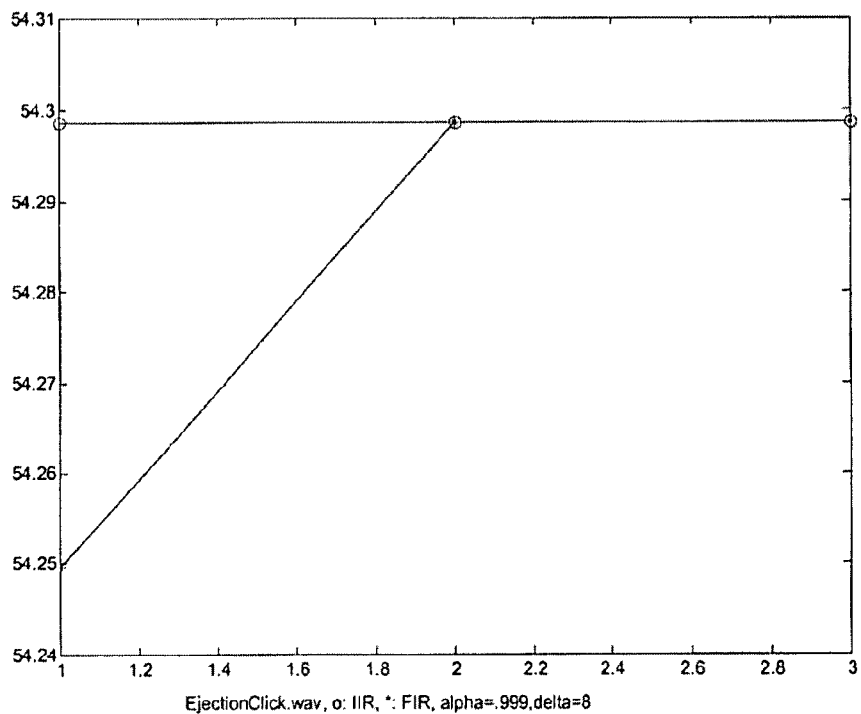

FIG. 41 illustrates detected heartbeat versus time using the FIR method and the IIR method of Equation (3), for Ejection Click case.

Figure 42:
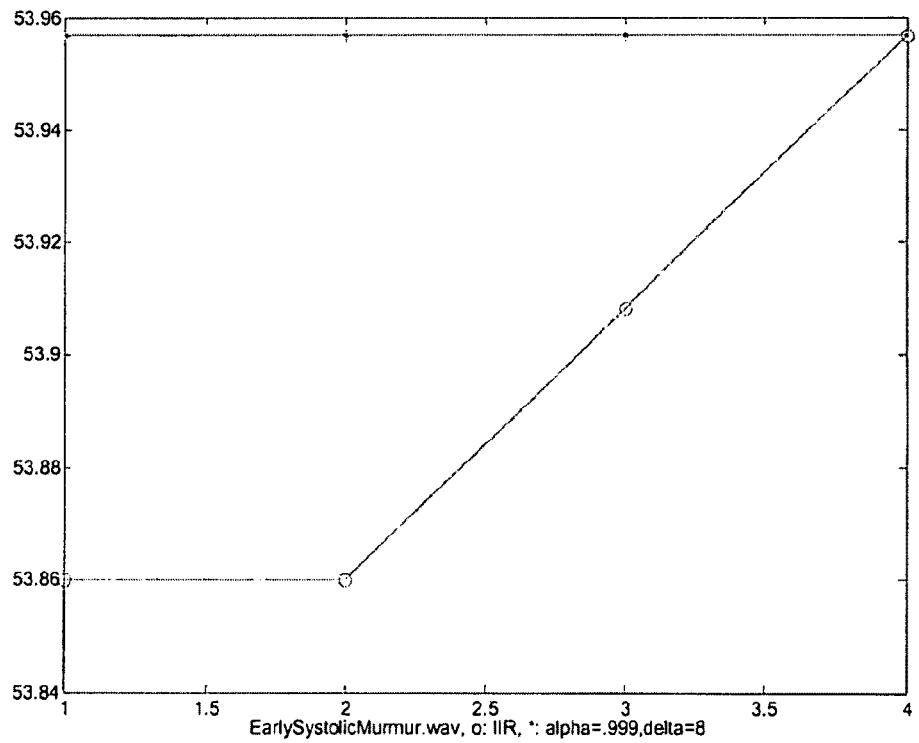

FIG. 42 illustrates detected heartbeat versus time using the FIR method and the IIR method of Equation (3), for Early Systolic case.

Figure 43:
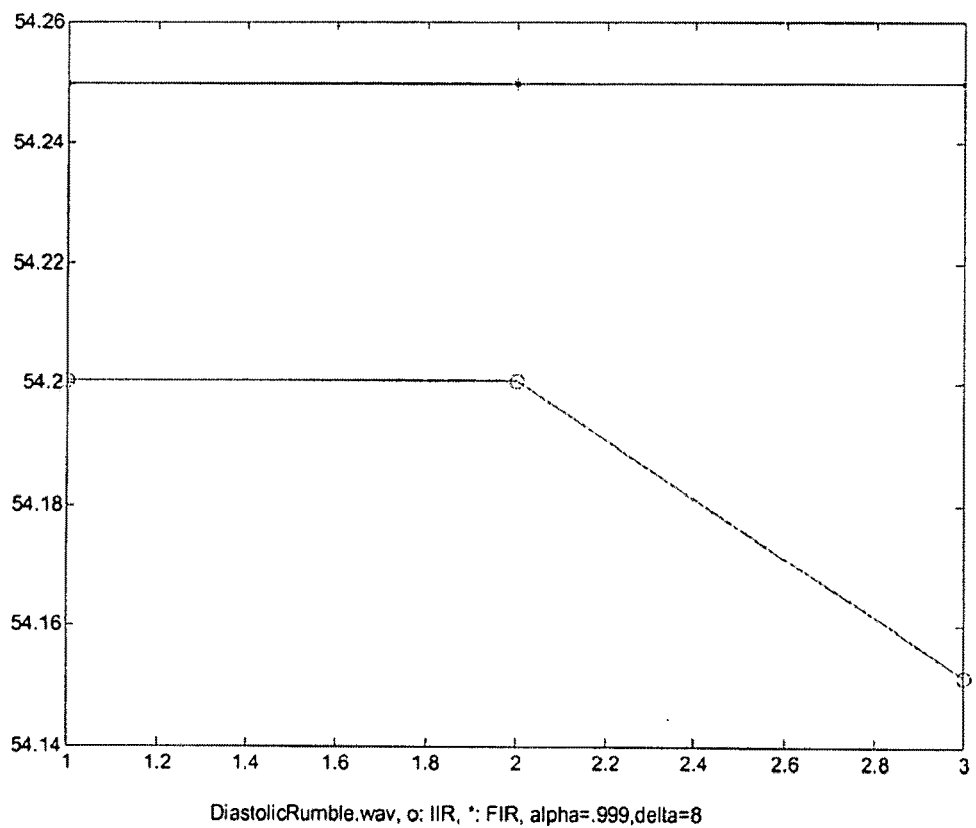

FIG. 43 illustrates detected heartbeat versus time using the FIR method and the IIR method of Equation (3), for Diastolic Rumble case.

Figure 44:
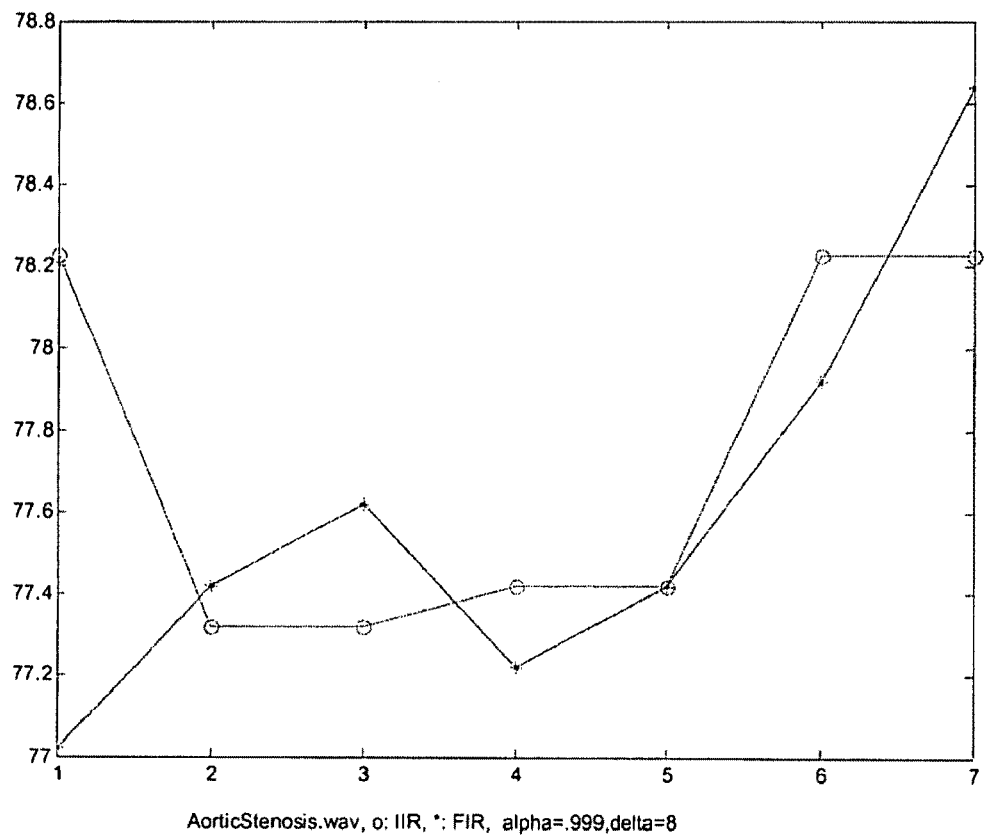

FIG. 44 illustrates detected heartbeat versus time using the FIR method and the IIR method of Equation (3), for Aortic Stenosis case.

In the simulations, the heartbeat was detected from the pre-recorded data, for various hear diseases. The FIR method and the IIR method of Equation (3) were employed with more than 30 records of heartbeats. WOLA subband signal in the first subband was employed with Fs=8 kHz, and R=8. A Power-Complementary analysis/synthesis window with L=128, N=32, and odd-stacking was used. Time window length was B=4000 samples (4 seconds), Minimum and Maximum heartbeats where 40 and 250 BPMs (Autocorrelation lag range: 240-1500). Delta=8 was used.

The heartbeat results for the FIR and IIR methods are almost identical for all test cases. The difference in heartbeat estimates is always less than one BPM.

As Delta increases, more variability of the heart beat estimate is observed. Values of Delta>8, lead to more than 1 BPM difference between the FIR and IIR estimates due to sluggish update of the recursion in Equation (3). However, up to Delta=16, the differences are still negligible.

In the simulations, Alpha was set to $$\text{Alpha}=1-1/(B/\text{Delta}) \quad (5)$$

To obtain (5), the time-constant of the exponential window, implied by the IIR method, is set to be equal to B:

$$\text{Tau}=1/(1-\text{Alpha})=B \rightarrow \text{Alpha}=1-1/B.$$

The term Delta was included to compensate for less frequent updates when Delta>1 to maintain the same implied window length for both methods.

For heartbeat detection, Adaptive Line Enhancement (ALE) may be implemented. The ALE method uses an adaptive filter with one input. The primary input is delayed by a fixed delay in the adaptive system. This is known to enhance the estimation of periodic signals. A low order (order 1 to 3) ALE may be used in just one subband with a delay of 100-200 samples in subband. To implement the ALE method, "Subband Adaptive Filtering (SAF) by Normalized Least Mean Square (NLMS)" (SAF-NLMS) method is utilized. The SAF-NLMS method is an effective adaptive filtering method designed to be implemented in subbands, for example, after WOLA analysis. For example, the SAF-NLMS may be implemented at the DSP core 106 of FIG. 31.

The signal processing/management methods and systems in accordance with the embodiments of the present invention have the following characteristics:

Low memory usage and low computation load and complexity.

Low processing time for signal synthesis.

Low communication bandwidth between the system and external systems (which results in low power).

Allow parallel processing, and thereby faster implementations, facilitated by decomposing the signal into subbands.

Permit proper task partitioning of necessary processing that can be implemented in an embedded system.

Allow near-orthogonal processing in each subband (for example, to tune parameters and to do processing in each subband independently or to process only relevant bands). Near-orthogonal subband signals do not materially interact with each other allowing the subband signals to be treated independently.

Employ the efficient WOLA implementation of oversampled filterbanks.

Rather than using floating-point, it allows less expensive alternatives including block floating-point processing (fixed-point hardware in combination with data-growth exponent control) for demanding applications and pure fixed-point processing for less demanding applications (combinations of block floating-point and fixed-point are of course included).

Allow better algorithm development framework through the exploitation of efficient subband processing enabling more complex algorithms to be deployed, leading to higher quality processing, better audio output and better feature extraction.

The signal processing/management methods and systems in accordance with the embodiments of the present invention is capable of achieving ultra-low power and small size leading to increased portability and battery life and low delay, and is capable of executing complex processing in real-time providing higher quality outputs (audio and otherwise). The signal processing/management methods and systems in accordance with the embodiments of the present invention provide more robust feature extraction and fit to the user/wearer properly.

The physiological system management and physiological signal processing of the present invention may be implemented by any hardware, software or a combination of hardware and software having the above described functions. The software code, instructions and/or statements, either in its entirety or a part thereof, may be stored in a computer readable memory. Further, a computer data signal representing the software code, instructions and/or statements, which may be embedded in a carrier wave may be transmitted via a communication network. Such a computer readable memory and a computer data signal and/or its carrier are also within the scope of the present invention, as well as the hardware, software and the combination thereof.

All citations are herein incorporated by reference.

The present invention has been described with regard to one or more embodiments. However, it will be apparent to persons skilled in the art that a number of variations and modifications can be made without departing from the scope of the invention as defined in the claims.

What is claimed is:

1. A system for implementing physiological system management (PSM) comprising:

a sensor for acquiring a physiological signal in a time domain from one or more physiological systems;

a Weighted Overlap-Add (WOLA) analysis filterbank for decomposing an input in the time domain, into subband signals;

a subband processor for detecting a predetermined physiological event occurring in the physiological system based on the subband signals, and determining a control for the physiological system based on the detected predetermined physiological event or a combination of the detected predetermined physiological event and the physiological signal, the subband processor extracting a feature of the physiological system;

a WOLA synthesis filterbank for synthesizing one or more of the subband signals output from the subband processor to provide a time domain output signal;

an output combiner for combining the extracted feature with the time domain output signal;

a controller for controlling the physiological system based on the determination; and a switch for selectively providing, to the input of the WOLA analysis filterbank, the output of the output combiner or the physiological signal in the time domain.

2. The system according to claim 1, further comprising:
a time-domain processor for processing the physiological signal to detect a predetermined time-domain physiological event, wherein the detected predetermined time-domain physiological event and the detected predetermined physiological event are used to determine the control.

3. The system according to claim 1, wherein the subband processor extracts a feature of the physiological signal from the subband signals, the processor comprising an event detection block for detecting the predetermined physiological event based on the extracted feature.

4. The system according to claim 3, further comprising:
means having a memory, for compressing and transmitting the physiological signals, the output signals from the system, the detected feature and the predetermined physiological event, and a telemetry for monitoring the system performance.

5. The system according to claim 1, further comprising a receiver for receiving data and command from outside of the system.

6. The system according to claim 3, wherein the subband processor implements a signal enhancement for removing noise or interference and enhancing the feature.

7. The system according to claim 3, wherein the PSM is cardiac rhythm management (CRM) where the feature is extracted by calculating absolute values or squared absolute values of each subband signal, and combining calculated values for subbands in each designated subband group, each group including one or more subbands, to obtain subband energy.

8. The system according to claim 7, wherein the subband energies are further processed for detecting one or more peaks by tracking average and maximum values of the corresponding subband energy through time-averaging.

9. The system according to claim 8, wherein the detected peaks are represented in a binary format containing "0", "1" or a combination thereof for each subband group, the "0" representing one of peak and no-peak, and the "1" representing the other, the binary decisions being combined by a combiner.

10. The system according to claim 9, wherein the combiner includes logical AND, logical OR operations, or combinations thereof.

11. The system according to claim 7, further comprising means for processing the subband energies and detecting one or more peaks by periodicity tracking using autocorrelation of one or more subband groups, an estimation of the autocorrelation, cross-correlation of multiple subband groups, an estimation of the cross-correlation, or combinations thereof.

12. The system according to claim 6, where the physiological system includes an autonomous nervous system where the acquisition module senses heart rate variability or other physiological information in the an autonomous nervous system.

13. The system according to claim 6, where the PSM includes an automatic drug delivery (ADD).

14. The system according to claim 6, where the PSM includes a cardiac rhythm management (CDM) and ADD applications.

15. The system according to claim 6, where the physiological system includes a brain and nervous system for controlling one or more neurological diseases.

16. The system according to claim 15, wherein the neurological disease includes epilepsy, seizure, or a combination thereof.

17. The system according to claim 6, where the PSM is applied to control a neuromuscular system.

18. The system according to claim 6, where the PSM is applied to a heart system, a brain system, an autonomous system, or combinations thereof.

19. The system according to claim 1, wherein the controller operates in a closed-loop, the controller monitoring the one or more physiological systems and adapting the control measure accordingly.

20. A method of implementing physiological system management (PSM), comprising:
acquiring, by a sensor, a physiological signal in a time domain from one or more physiological systems;
decomposing, by a Weighted Overlap-Add (WOLA) analysis filterbank, an input of the WOLA analysis filterbank in the time domain, into subband signals;
in a subband processor, extracting a feature of the physiological system, detecting a predetermined physiological event occurring in the physiological system based on the subband signals, and determining a control for the physiological system based on the detected predetermined physiological event or a combination of the detected predetermined physiological event and the physiological signal;
synthesizing, by a WOLA synthesis filterbank, one or more of the subband signals output from the subband processor to provide a time domain output signal;
combining, by an output combiner, the extracted feature with the time domain output signal;
controlling, by a controller, the physiological system based on the determination; and
selectively providing, to the input of the WOLA analysis filterbank, the output of the output combiner or the physiological signal in the time domain.

21. A method according to claim 20, further comprising the step of:
monitoring the physiological information and repeating the decomposing, detecting, decision-making and applying steps.

22. A method according to claim 21, wherein the decision-making step includes the step of:
adapting a control strategy based on evaluation of the applied control measure.

23. A method according to claim 20, wherein the step of extracting comprises:

extracting a feature of the physiological signal from the subband signals, the event detection step detecting the predetermined physiological event based on the extracted feature.

24. A method according to claim 23, further comprising: removing noise or interference and enhancing the feature in the subband domain.

25. A method according to claim 20, further comprising: receiving one or more data to control the collecting step, the decomposing step, the detecting step, the determining step, the controlling step, or combinations thereof.

26. A computer readable medium having recorded thereof statements and instructions for executing by a computer to carry out the method of claim 20.

27. The system according to claim 1, wherein the subband signals are complex-valued signals.

28. A method according to claim 20, wherein the subband signals are complex-valued signals.

* * * * *